United States Patent [19]

Murray et al.

[11] Patent Number: 5,968,815
[45] Date of Patent: Oct. 19, 1999

[54] PROMOTER OF M. PARATUBERCULOSIS AND ITS USE FOR THE EXPRESSION OF IMMUNOGENIC SEQUENCES

[75] Inventors: Alan Murray, Palmerston North, New Zealand; Marina Gheorghiu, Neuilly-Sur-Seine; Brigitte Gicquel, Paris, both of France

[73] Assignees: Institut Pasteur, Paris Cedex, France; Massey University, Palmerston North, New Zealand

[21] Appl. No.: 08/211,718

[22] PCT Filed: Oct. 23, 1992

[86] PCT No.: PCT/EP92/02431

§ 371 Date: Oct. 6, 1994

§ 102(e) Date: Oct. 6, 1994

[87] PCT Pub. No.: WO93/08284

PCT Pub. Date: Apr. 29, 1993

[30] Foreign Application Priority Data

Oct. 25, 1991 [FR] France .................................. 91 13227

[51] Int. Cl.$^6$ .............................. C12N 15/63; C12N 1/21; C07H 21/04; C12P 21/02
[52] U.S. Cl. ..................... 435/320.1; 435/69.1; 435/70.1; 435/71.1; 435/252.3; 435/252.31; 435/252.33; 435/252.5; 536/23.1; 536/24.1
[58] Field of Search ................................ 435/320.1, 69.1, 435/70.1, 71.1, 172.1, 169, 170, 171, 252.1, 252.3, 252.31, 252.33, 253.5; 935/22, 33, 47, 66; 536/24.1, 23.1

[56] References Cited

U.S. PATENT DOCUMENTS 5,330,754  7/1994  Kapoor et al. ........................ 424/190.1

FOREIGN PATENT DOCUMENTS 0288306  10/1988  European Pat. Off. .
0400973  12/1990  European Pat. Off. .

OTHER PUBLICATIONS

Fox "No Winners Against AIDS" Biotechnology vol. 12 Feb. 1994 p. 128.
Kunze etal. "IS901, A New Member of a Widespread Class of Stypleal Insertion Seqences . . . " Mol. Microbiol. 5(9)2265–2272 1991.

*Primary Examiner*—David Guzo
*Assistant Examiner*—Nancy J. Degen
*Attorney, Agent, or Firm*—Oblon, Spivak, McClelland, Maier & Neustadt, P.C.

[57] ABSTRACT

The invention relates to a nucleotide sequence which is present at a position adjacent to the 5' end of the reverse sequence complementary to the open reading frame coding for a potential transposase contained in the insertion element IS900 in *Mycobacterium paratuberculosis*. The nucleotide sequence has promoter functions and contains important signals for the regulation of transcription and translation. The invention also relates to methods for cloning and expressing heterologous proteins using such regulatory sequences, to vectors and transformed host cells containing these sequences, and to immunogenic compositions prepared by expression of nucleotide sequences placed under control of these regulatory sequences.

45 Claims, 50 Drawing Sheets

1
GAT CCC GTG ACA AGG CCG AAG AGC CCG CGA CCG TGC GGT CGT CGA CGA (-35)
CCG AGT GTG AGC AGA CCC CCT GGT GAA GGG TGA ATC GAC AGG TAC ACA 101     (-10)      +1
CAG CCG CCA TAC ACT TCG CTT CAT GCC CTT ACG GGG GGC GGC CAA CCC

AGA AGG AGA TTC TCA ATG ACG TTG TCA AGC CGC CGC GGT AGT GGT TGC
    SD           Met Thr Leu Ser Ser Arg Arg Gly Ser Gly Cys
        201
GGG GTG GTA GAC AGC GTG GTC GCG CAG CAT GGC CCA CAG GAC GTT GAG
Gly Val Val Asp Ser Val Val Ala Gln His Gly Pro Gln Asp Val Glu

GCG GCG GCG GGC CAG GGC GAG GAC GGC TTG GGT GTG GCG TTT TCC TTC
Ala Ala Ala Gly Gln Gly Glu Asp Gly Leu Gly Val Ala Phe Ser Phe
        301
GGT GCG TTT TCG GTC GTA GTA GGT GCG CGA GGA GGG GTC GGT GCG GAT
Gly Ala Phe Ser Val Val Val Gly Ala Arg Gly Gly Val Gly Ala Asp

GCT GAC CAA GGC CGA CAG GTA GCA GGC GCG CAG CAG GCG CCG GTC GTA
Ala Asp Gln Gly Arg Gln Val Ala Gly Ala Gln Gln Ala Pro Val Val
        401
GCG TCG GGG GCG TTT GAG GTT TCC GCT GAT GCG GCC GGA ATC TCG TGG
Ala Ser Gly Ala Pha Glu Val Ser Ala Asp Ala Ala Gly Ile Ser Trp

TAC CGG CGC CAG GCC GGC GAC GCC GGC GAG GCG GTC GGC GGA GGC GAA
Tyr Arg Arg Gln Ala Gly Asp Ala Gly Glu Ala Val Gly Gly Gly Glu
        501
TGC GGC CAT GTC CCC GCC GGT GGC GGC GAG GAA CTC AGC GCC CAG GAT
Cys Gly His Val Pro Ala Gly Gly Gly Glu Glu Leu Ser Ala Gln Asp

GAC GCC GAA TCC GGG CAT GCT CAG GAT GAT TTC GGC GTG GCG GTG GCG
Asp Ala Glu Ser Gly His Ala Gln Asp Asp Phe Gly Val Ala Val Ala
        601
GCG AAA TCG CTC CTC GAT CAT CGC GTC GGT GTC GCC GAT TTC GGT GTC
Ala Lys Ser Leu Leu Asp His Arg Val Gly Val Ala Asp Phe Gly Val

GAG GGC CAT CAC CTC CTT GGC CAG GCG GGC CAC CAC AGT GGC CGC CAG
Glu Gly His His Leu Leu Gly Gln Ala Gly His His Ser Gly Arg Gln
                                      701           716
TTG TTG GCC GGG CAC GAT GCT GTG TTG GGC GTT AGC GGC CTG CA
Leu Leu Ala Gly His Asp Ala Val Leu Gly Val Ser Gly Leu

FIG.2

SEQUENCE ID NO.1
5' CCCTCTAGAATTCCGTGACAAGGCCGAAGAGCCCGCGA 3'

SEQUENCE ID NO.2
5' AACATATGAGATCTTCTCCTTCTGGGTTGGCCGCCCC 3'

POSITION OF SEQUENCE FROM THE FRAGMENT AT AMPLIFIER:
CCCTCTAGAATTCCGTGACAAGGCCGAAGAGCCCGCGA 3'

```
  1          11         21         31         41         51
  GATCCCGTGACAAGGCCGAAGAGCCCGCGACCGTGCGGTCGTCGAGGACCGAGTGTG
  61         71         81         91        101        111
  AGCAGACCCCCTGGTGAAGGGTGAATCGACAGGTACACACAGCCGCCATACACTTCG
 121        131        141        151        161
  CTTCATGCCCCTTACGGGGGCGGCCAACCCAGAAGGAGATTCTCA ATG ACG TTG
                                              SD  Met Thr Leu
                                            3' CCCCGGCCGGTTGGGTCTTCCTCTTCTAGA GTA TAC AA
 171
 Ser Ser Arg Arg
 TCA AGC CGC CGC
```

FIG.7

```
                10                                    30
GAT CCC GTG ACA AGG CCG AAG AGC CCG CGA CCG TGC GGT CGT CGA 50                              70                      90
CGA CCG AGT GTG AGC AGA CCC CCT GGT GAA GGG TGA ATC GAC AGG 110                         130
TAC ACA CAG CCG CCA TAC ACT TCG CTT CAT GCC CTT ACG GGG GGC 150                         170
GGC CAA CCC AGA AGG AGA TTC TCA ATG ACG TTG TCA AGC CGC CGC
                                Met Thr Leu Ser Ser Arg Arg 190                             210
GGT AGT GGT TGC GGG GTG GTA GAC AGC GTG GTC GCG CAG CAT GGC
Gly Ser Gly Cys Gly Val Val Asp Ser Val Val Ala Gln His Gly 230                           250                       270
CCA CAG GAC GTT GAG GCG GCG GCG GGC CAG GGC GAG GAC GGC TTG
Pro Gln Asp Val Glu Ala Ala Ala Gly Gln Gly Glu Asp Gly Leu 290                         310
GGT GTG GCG TTT TCC TTC GGT GCG TTT TCG GTC GTA GTA GGT GCG
Gly Val Ala Phe Ser Phe Gly Ala Phe Ser Val Val Val Gly Ala 330                             350
CGA GGA GGG GTC GGT GCG GAT GCT GAC CAA GGC CGA CAG GTA GCA
Arg Gly Gly Val Gly Ala Asp Ala Asp Gln Gly Arg Gln Val Ala 370                           390
GGC GCG CAG CAG GCG CCG GTC GTA GCG TCG GGG GCG TTT GAG GTT
Gly Ala Gln Gln Ala Pro Val Val Ala Ser Gly Ala Phe Glu Val 410                             430                    450
TCC GCT GAT GCG GCC GGA ATC TCG TGG TAC CGG CGC CAG GCC GGC
Ser Ala Asp Ala Ala Gly Ile Ser Trp Tyr Arg Arg Gln Ala Gly 470                         490
GAC GCC GGC GAG GCG GTC GGC GGA GGC GAA TGC GGC CAT GTC CCC
Asp Ala Gly Glu Ala Val Gly Gly Gly Glu Cys Gly His Val Pro 510                             530
GCC GGT GGC GGC GAG GAA CTC AGC GCC CAG GAT GAC GCC GAA TCC
Ala Gly Gly Gly Glu Glu Leu Ser Ala Gln Asp Asp Ala Glu Ser 550                             570
GGG CAT GCT CAG GAT GAT TTC GGC GTG GCG GTG GCG GCG AAA TCG
Gly His Ala Gln Asp Asp Phe Gly Val Ala Val Ala Ala Lys Ser
```

FIG.10A

```
      590                            610                            630
CTC CTC GAT CAT CGC GTC GGT GTC GCC GAT TTC GGT GTC GAG GGC
Leu Leu Asp His Arg Val Gly Val Ala Asp Phe Gly Val Glu Gly 650                            670
CAT CAC CTC CTT GGC CAG GCG GGC CAC CAC AGT GGC CGC CAG TTG
His His Leu Leu Gly Gln Ala Gly His His Ser Gly Arg Gln Leu 690                            710
TTG GCC GGG CAC GAT GCT GTG TTG GGC GTT AGC GGC CTG CAG CGC
Leu Ala Gly His Asp Ala Val Leu Gly Val Ser Gly Leu Gln Arg 730                            750
GGT GGC TGC GAC GGT ATC GGC GTT GCG GGC CTT GCG TTT ACG CAA
Gly Gly Cys Asp Gly Ile Gly Val Ala Gly Leu Ala Phe Thr Gln 770                            790                            810
GAA CGC GGC TAC TCG AGC GCC ACC GGC GCT GCG CAG CGC GTC GGG
Glu Arg Gly Tyr Ser Ser Ala Thr Gly Ala Ala Gln Arg Val Gly 830                            850
AGT TTG GTA GCC AGT AAG CAG GAT CAG CGC GGC ACG GCT CTT GTT
Ser Leu Val Ala Ser Lys Gln Asp Gln Arg Gly Thr Ala Leu Val 870                            890
GTA GTC GAA GGC GCG TTC CAG CGC CGG AAA GTA TTC CAG CAG CTG
Val Val Glu Gly Ala Phe Gln Arg Arg Lys Val Phe Gln Gln Leu 910                            930
GGC GCG CAT TCG GTT GAT CGC CCG GGT CCG ATC AGC CAC CAG ATC
Gly Ala His Ser Val Asp Arg Pro Gly Pro Ile Ser His Gln Ile 950                            970                            990
GGA ACG TCG GCT GGT CAG GAT GCG CAG CTC GAC TGC GAT GTC ATC
Gly Thr Ser Ala Gly Gln Asp Ala Gln Leu Asp Cys Asp Val Ile 1010                           1030
GCC GGC GCG CAG AGG CTG CAA GTC GTG GCG CAT CCG GGC CTG ATC
Ala Gly Ala Gln Arg Leu Gln Val Val Ala His Pro Gly Leu Ile 1050                           1070
GGC GAT GAT CGC AGC GTC TTT GGC GTC GGT CTT GCC TTC GCC GCG
Gly Asp Asp Arg Ser Val Phe Gly Val Gly Leu Ala Phe Ala Ala
```

FIG.10B

```
              1090                         1110
GTA ACT ACC CGC GGC GTG ATG GAC CGT GCG CCC GGG AAT ATA AAG
Val Thr Thr Arg Gly Val Met Asp Arg Ala Pro Gly Asn Ile Lys 1130                         1150                   1170
CAG CCG CTG CCC GGC AGC GAT GAG CAA GGC GAT CAG CAA CGC GGC
Gln Pro Leu Pro Gly Ser Asp Glu Gln Gly Asp Gln Gln Arg Gly 1190                  1210
GCC GCC GGC GTT GAG GTC GAT CGC CCA CGT GAC CTC GCC TCC ATC
Ala Ala Gly Val Glu Val Asp Arg Pro Arg Asp Leu Ala Ser Ile 1230                         1250
GGC CAA CGT CGT CAC CGC CGC AAA TCA ACT CCA GCA GCG CGG CCT
Gly Gln Arg Arg His Arg Arg Lys Ser Thr Pro Ala Ala Arg Pro 1270                         1290
CGT CGT TGG CCA CCC GCT GCG AGA GCA ATC GCT GCG CGT CGT CGT
Arg Arg Trp Pro Pro Ala Ala Arg Ala Ile Ala Ala Arg Arg Arg 1310                         1330                   1350
TAA TAA CCA TGC AGT AAT GGT CGG CCT TAC CGG CGT CCA CGC CCG
TER 1370                  1390
CCC AGA CAG GTT GTG CCA CAA CCA CCT CCG TAA CCG TCA TTG TCC 1410                  1430
AGA TCA ACC CAG CAG ACG ACC ACG CCG ACG TGT CCT TAC ACA GCG 1450                  1470
ATC CAA TCG CAT CTC TCA ATT AGC GGT CGA GTC GTC GCG GGA CGC 1490                         1510                   1530
CGG GCG GCC AAT CTC CTT CGG CCA TCC AAC ACA GCA ACC ACA TGA 1550                  1570
AAG CCA TAC CCG ACG TCC CTG GGC AAT TCG AAG CCT AAG CCG ACG

1590
GCC CCG AAC ACC CTT CAA GAA AGG TAA GGA ATT
```

FIG.10C

PROMOTER OF M. PARATUBERCULOSIS AND ITS USE FOR THE EXPRESSION OF IMMUNOGENIC SEQUENCES

BACKGROUND OF THE INVENTION

1. Field of the Invention

The object of the invention is a nucleotide sequence which makes it possible to done or express nucleotide sequences in a specific cell host.

A nucleotide sequence of the invention may be obtained from *Mycobacterium paratuberculosis*.

2. Description of the Related Art

Certain strains of mycobacteria are particularly well known, for example the bacillus of Calmette and Guerin (BCG) which is an avirulent strain of *Mycobacterium bovis* widely used throughout the world in the context of vaccination against tuberculosis. Its biological properties make it a useful candidate for the development of recombinant vaccines. The cell wall functions as a very effective adjuvant and a single inoculation can trigger long-lasting immunity. Serious side effects due to this bacillus are rare even on repeated immunizations.

The induction of specific immunity, following vaccination by BCG is initiated when T cells interact with macrophages presenting mycobacterial antigens in combination with products of the major histocompatibility complex (abbreviated to MHC). Clones of sensitized T cells proliferate and produce lymphokines which in turn activate macrophages in order to eliminate the bacilli non-specifically. In addition, helper T cells induce the proliferation of B cell clones which lead to the production of antibodies.

Attempts have already been made to carry out the cloning and expression of heterologous genes in BCG, in particular by using available know-how relating to replicative or integrative vectors. Thus an epitope of the gag protein of HIV-1 has been cloned in the form of a fusion polypeptide with the alpha antigen, this antigen being one of the major proteins exported by mycobacteria, in particular the BCG or *Mycobacterium kansasii* and resistance genes for antibiotics have been expressed under the control of their own regulatory region. In order to optimize the expression of heterologous antigens in BCG recombinants, the inventors have directed their researches towards the characterization of the gene regulatory units which are functional in the mycobacteria The inventors have thus described the isolation and characterization from *Mycobacterium paratuberculosis* of nucleotide sequences which make possible the expression of given nucleic acids in mycobacteria or in other cell hosts.

By nucleic acid is meant any nucleotide sequence capable of being cloned and/or expressed whatever its composition, length or origin (synthetic or obtained by extraction).

Various experiments have been performed on *M. paratuberculosis* (also designated hereafter by Mptb) and Green et al. (Nucleic Acids Research Vol. 17 (22) 1989, pages 9063–9072) in particular have characterized and sequenced an insertion element of this mycobacteria, an element which has been called IS900. According to Green et al., this insertion element contains an open reading frame called ORF1197 which codes for a protein of 399 amino acids.

SUMMARY OF THE INVENTION

The inventors have investigated specific sequences of the species *Mycobacterium paratuberculosis* by screening a lambda gt11 genomic library by performing hybridization assays with the DNA of strains of other mycobacteria, in particular *M. phlei* described in Murray A. et al. New Zealand Veterinary Journal 37: 47–50. On this occasion they were interested in a specific DNA sequence which contained a fragment adjacent to the element IS900 described by Green et al.

They determined the presence of a sequence adjacent to the 5' part of the reverse sequence complementary to the open reading frame which codes for a potential transposase contained in the insertion element IS900; this novel sequence is capable of having promoter functions and of containing important signals for the regulation of transcription and translation.

A nucleotide sequence according to the invention which can be used for the cloning and/or expression of a nucleic acid is characterized in that it comprises a sequence (I) selected from:

a) the sequence represented in FIG. 2 (SEQ ID NO:1) or any part of this sequence likely to be implicated in the expression of a nucleic acid which is placed under its control, b) a sequence hybridizing with the sequence complementary to this sequence a) under conditions given below.

The DNA of Mptb is shown as a grey segment bounded by two curved lines and the lacZ gene as a segment bounded by two curved lines.

pAM3 was digested with BamHI/PstI to give rise to a 716 bp fragment which was recovered from a 1% agarose gel by using the Geneclean system. The fragment was ligated to the plasmid pNM482 digested by BamHI/PstI to produce pAM310. Competent *E. coli* MC1061 strains were transformed with the ligation product and the cells were spread on a Luria broth (LB) medium containing 100 µg/ml of ampicillin. The clones carrying the recombinant plasmid pAM310 were recovered by checking the restriction map of the plasmid pAM310 were recovered by checking the restriction map of the plasmid. The 3.8 kb fragment obtained from pAM310 by digestion with the enzymes SmaI/DraI were eluted from a 0.8% agarose gel and ligated by its blunt ends to the ScaI site of pRR3 to produce pAM320. In this construction the $Ap^R$ gene for resistance to penicillin was interrupted. The *E. coli* MC1061 cells were transformed and the colonies were selected by the phenotype $Km^R Ap^S$. The DNA of these recombinants was prepared by alkaline lysis and used to transform *M. smegmatis* $mc^2$ 155 (Snapper et al., 1990, Molec. Midrobiol. 4: 1911–1919) by electroporation.

FIG. 2: Nucleotide sequence of BamHI/PstI fragment of 716bp obrained from pAM3 and the 185 N-terminal amino acids of ORF2 (SEQ ID NO:1)

SD=Shine-Dalgarno; +1=transcription initiation site

Figure 1A:
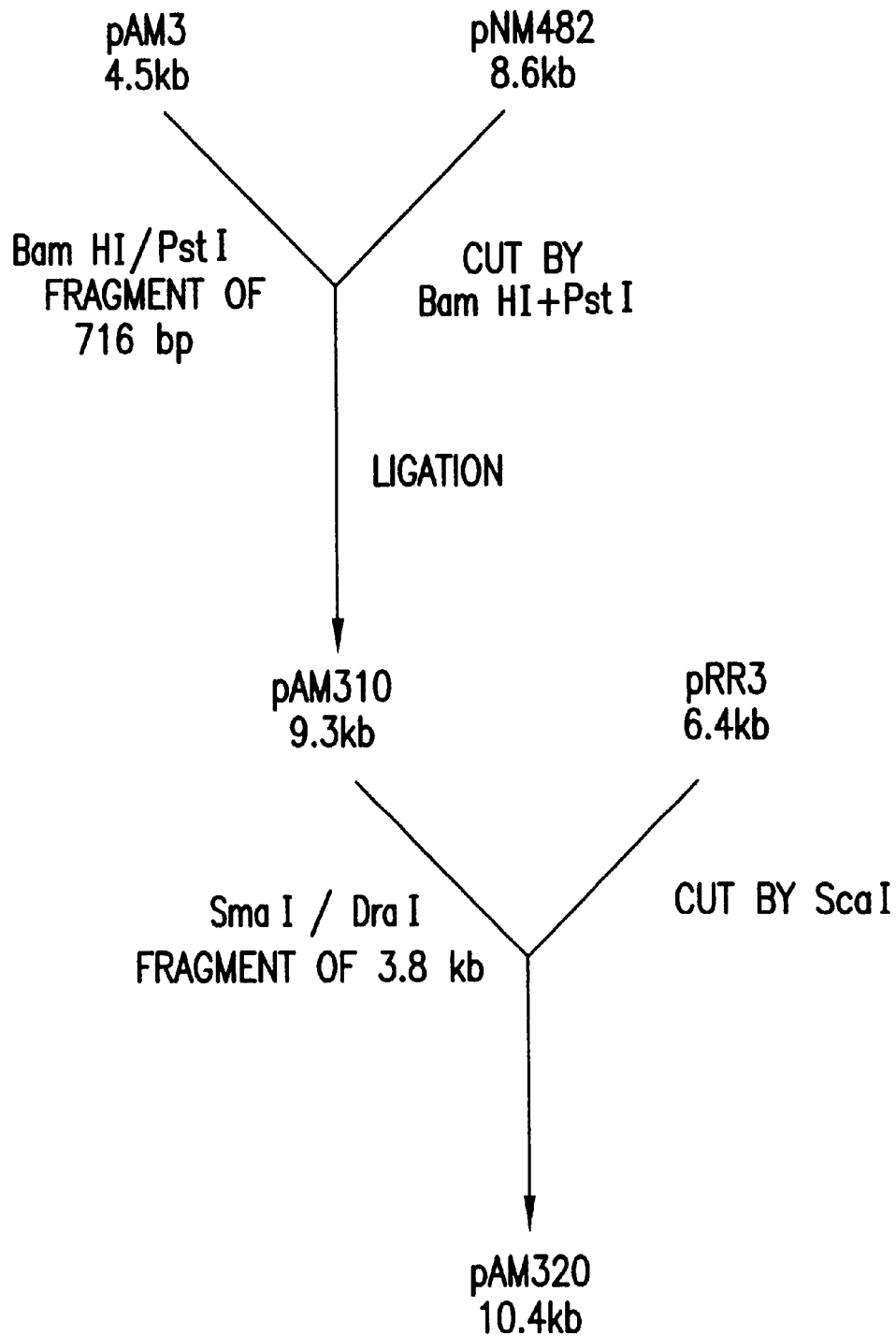
FIG. 1: Schematic description of the construction of pAM320
Figure 1B:
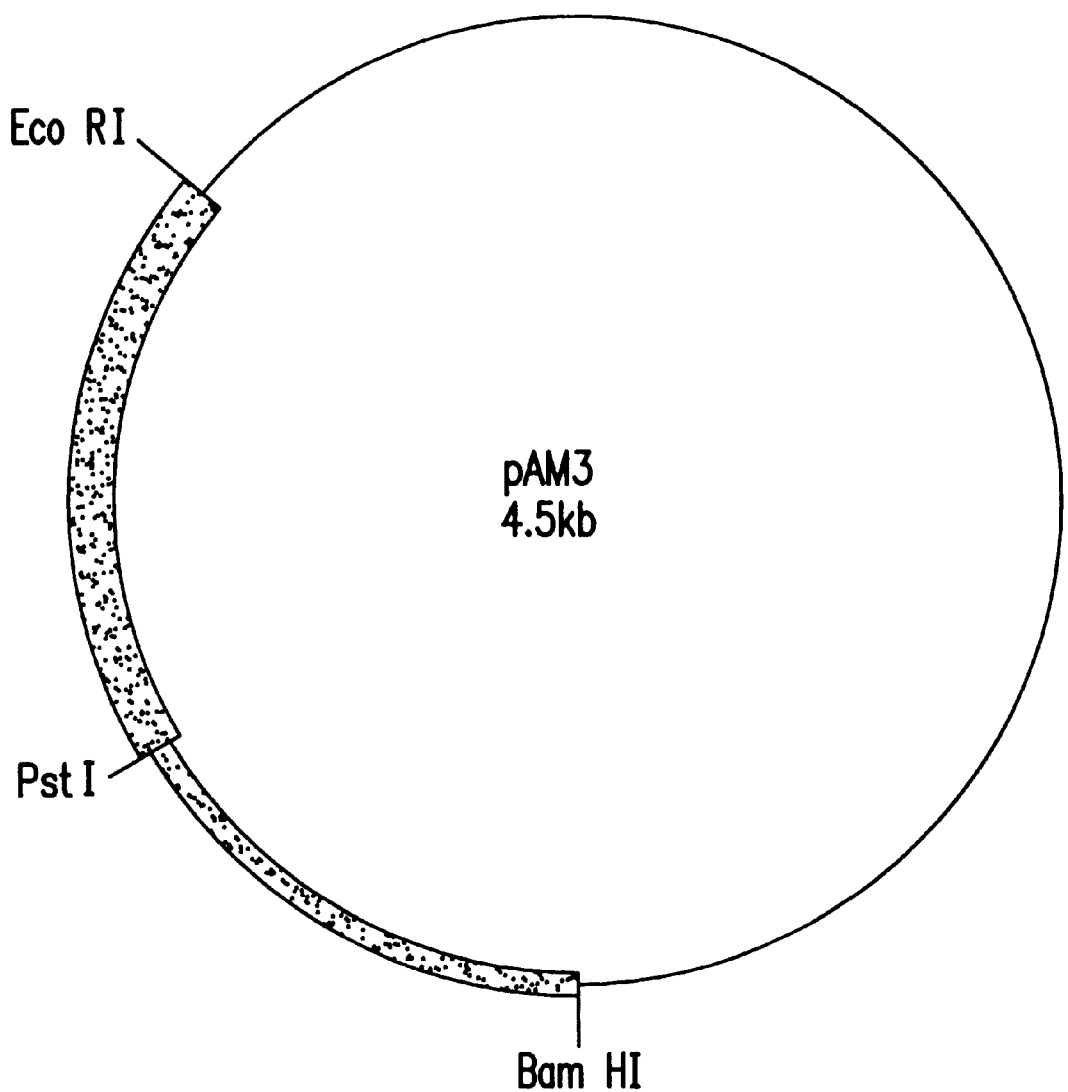
Figure 1C:
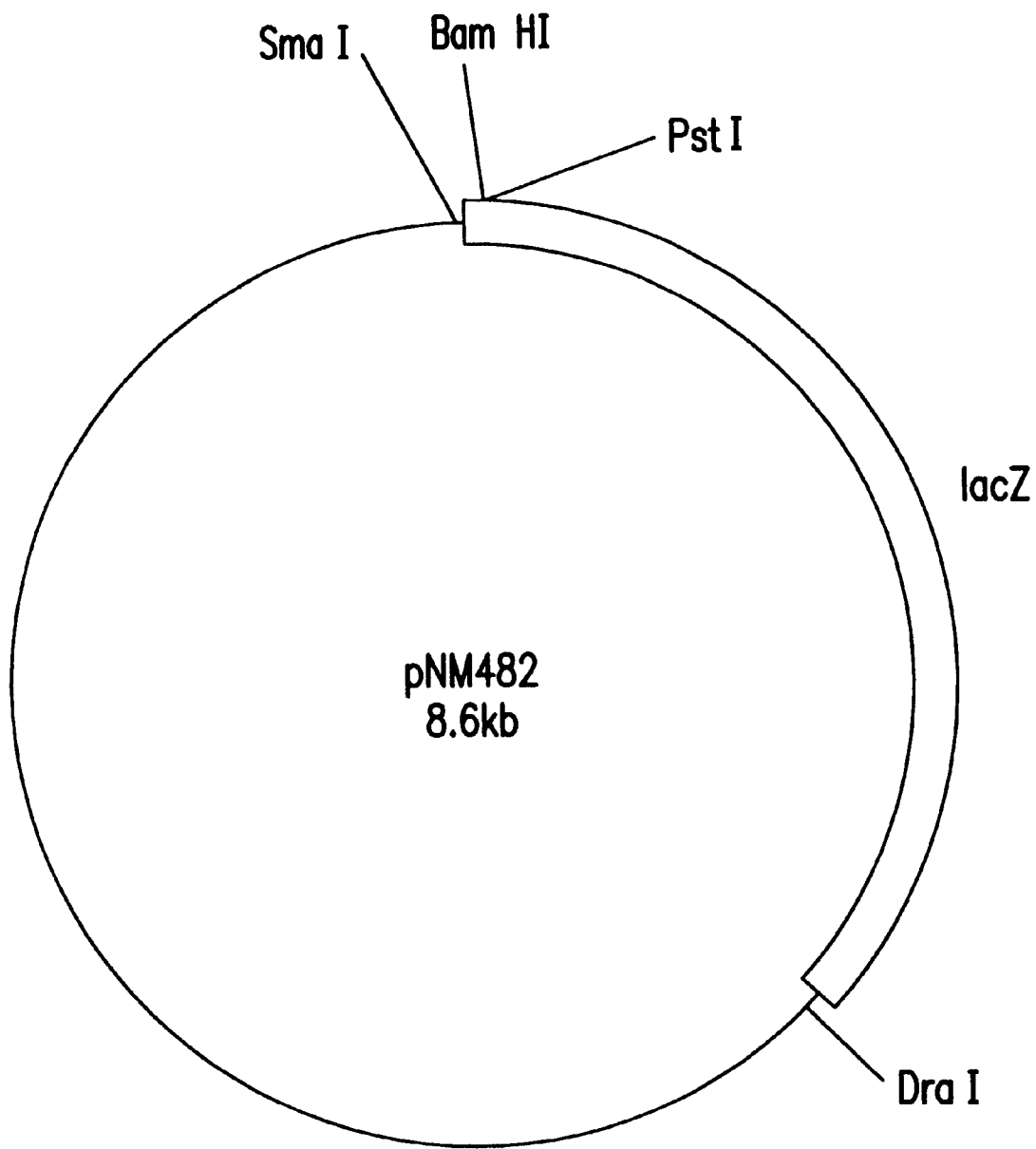
Figure 1D:
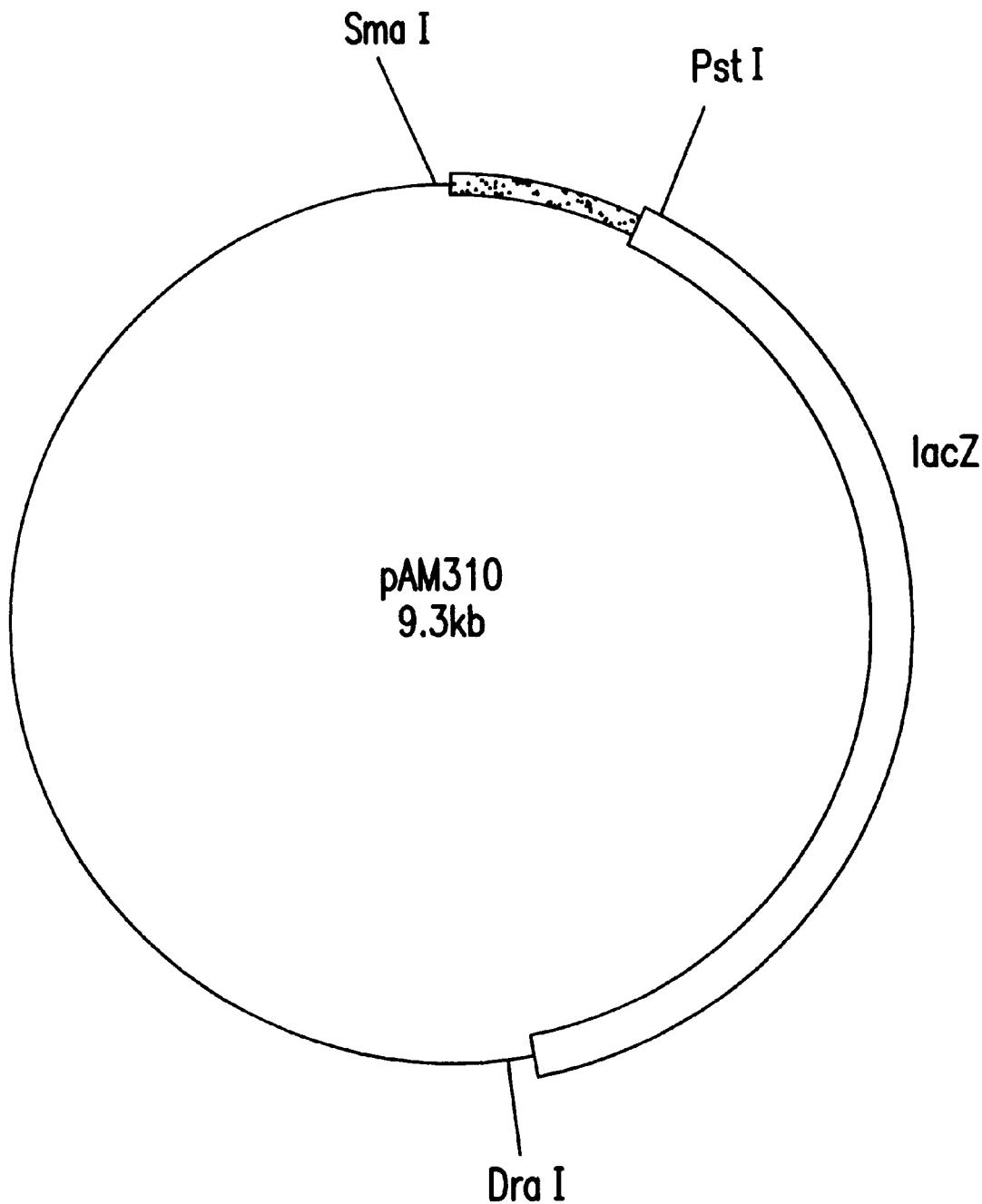
Figure 1E:
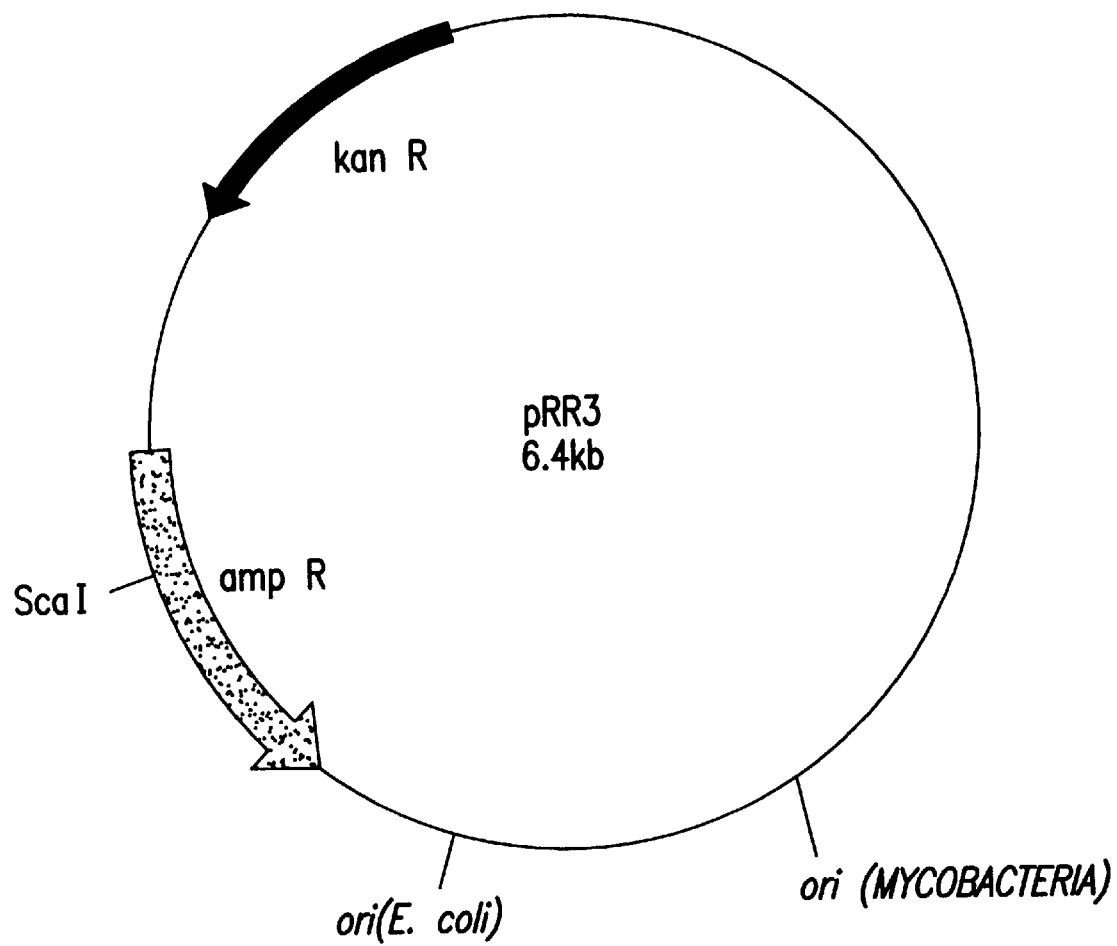
Figure 1F:
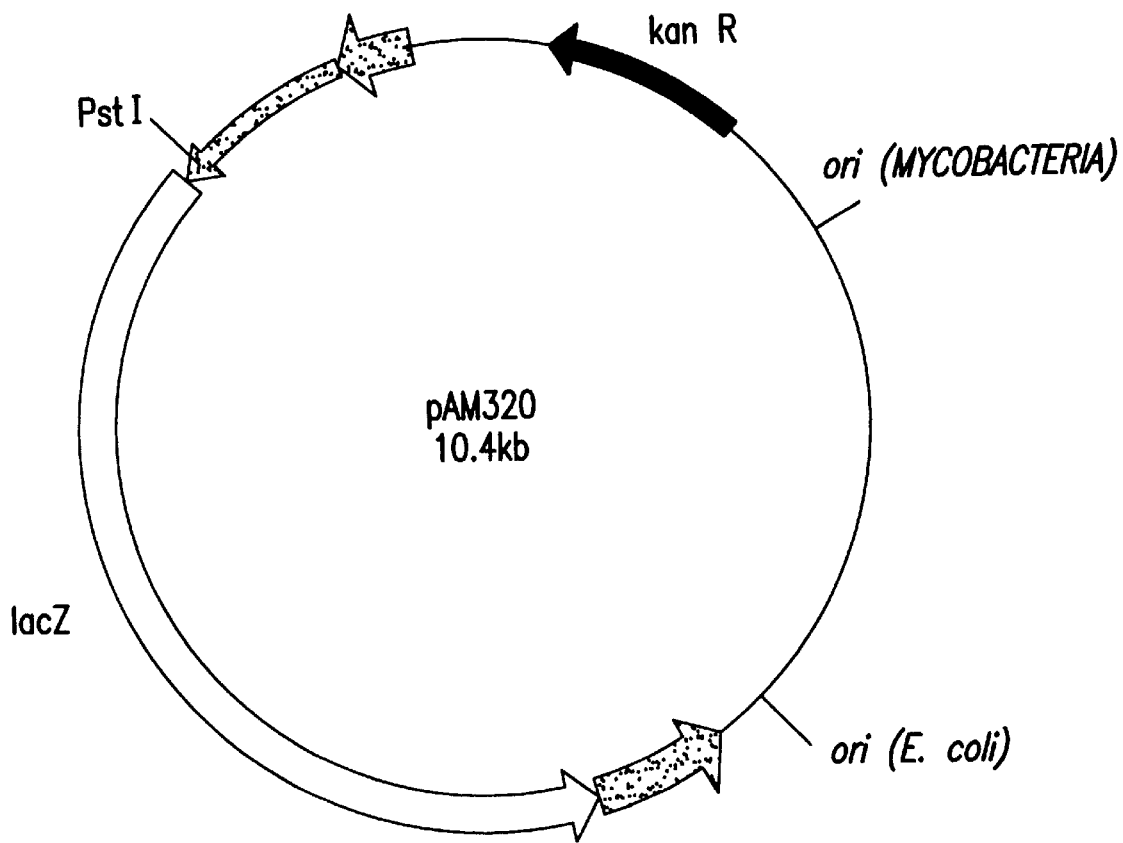
Figure 3:
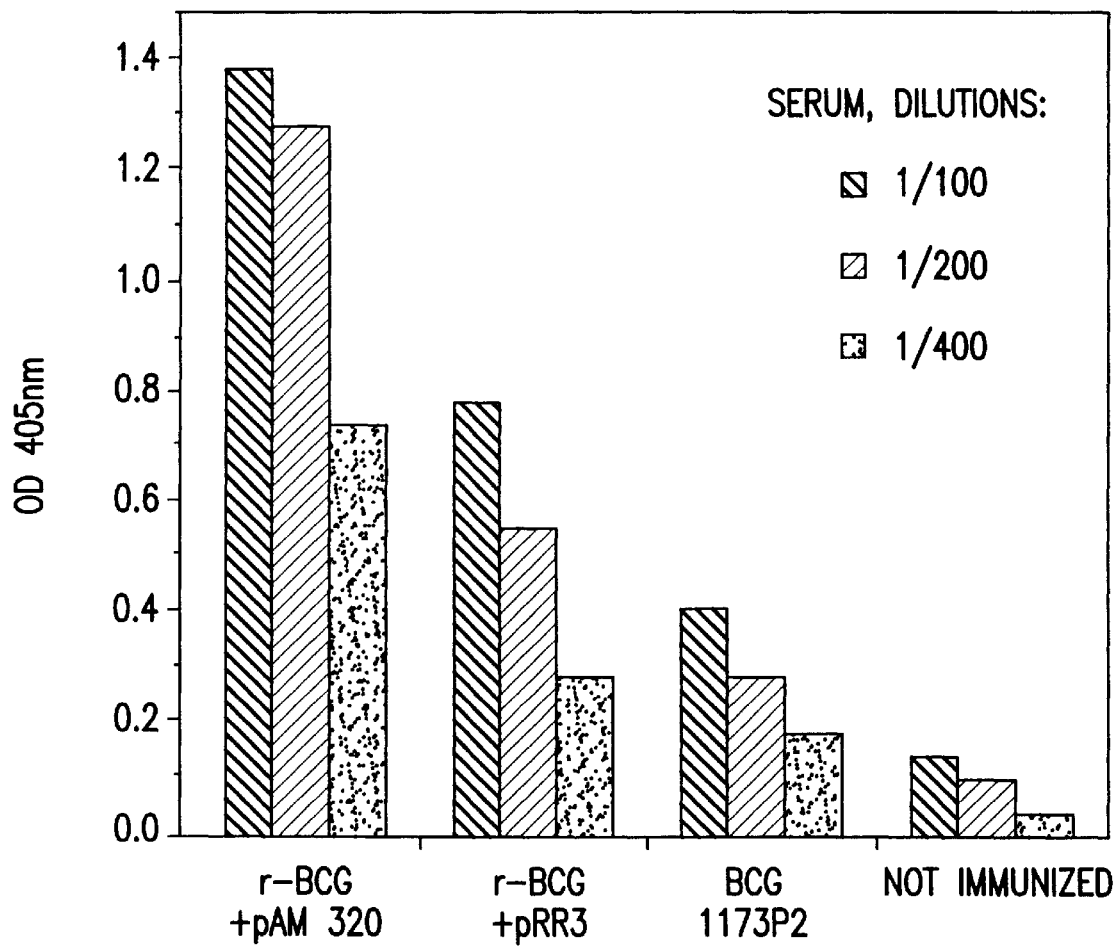

FIG. 3: ELISA on mouse sera taken 40 days after i.v. inoculation

Balb/c mice were immunised by the i.v. route with $10^7$ CFU of r-BCG transformed by pAM320, or with the BCG strain 1137P2. Several unimmunised mice were used as control. The sera were taken 40 days after immunization and tested. The anti-beta-galactosidase antibodies were detected by the ELISA method (Engval E. and Perlman P., 1971 Immunochemistry 8: 871–874). The microtitration plates were coated with 1 µg of beta galactosidase per well. The anti-beta-galactosidase antibodies were detected with goat anti-mouse immunoglobulin antibodies labelled with alkaline phosphatase (Biosis). Each value corresponds to a pool of sera from four or five mice.

Figure 4:
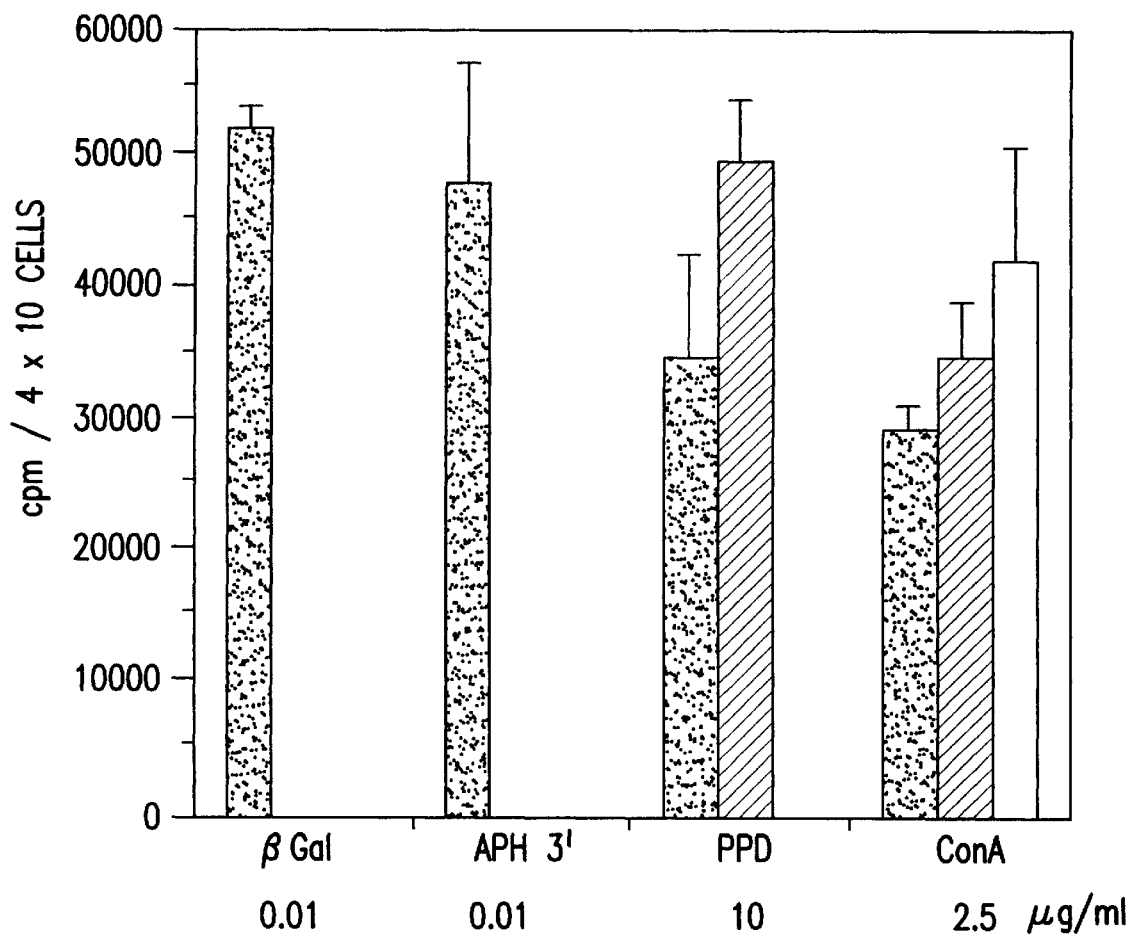

FIG. 4: Proliferative response of the lymph node cells of a Balb/c mouse immunised sucutaneously with $10^7$ CFU of BCG+pAM3, and the BCG strain 1173P2

A group of immunized mice was inoculated with 0.1 ml of IFA. Two weeks later the proliferative reponses of the LN cells (lymph node cells) to beta-galactosidase, APH3', PPD and ConA were tested.

Figure 5A:
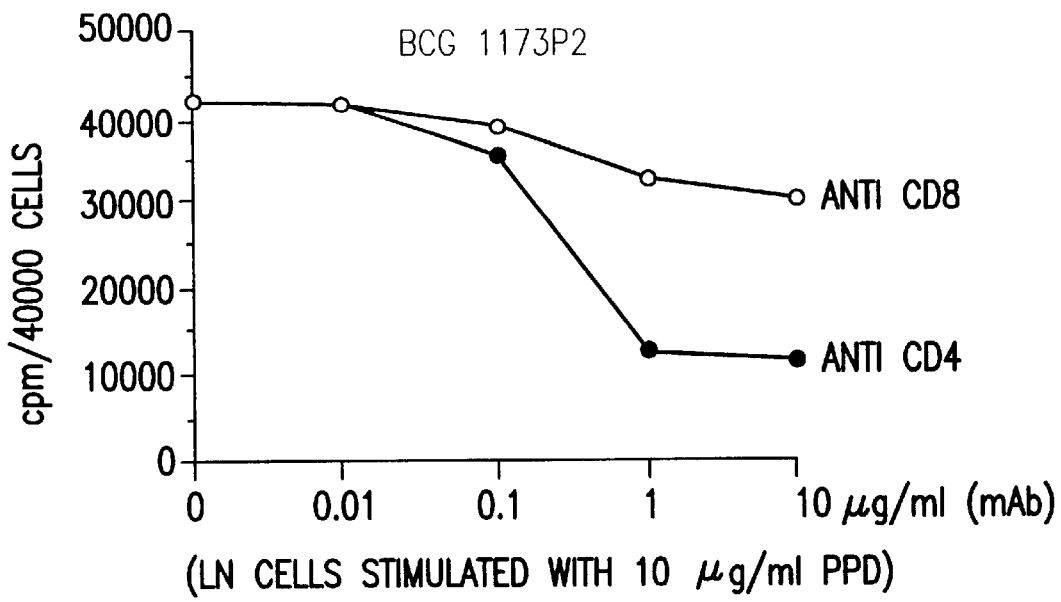
Figure 5B:
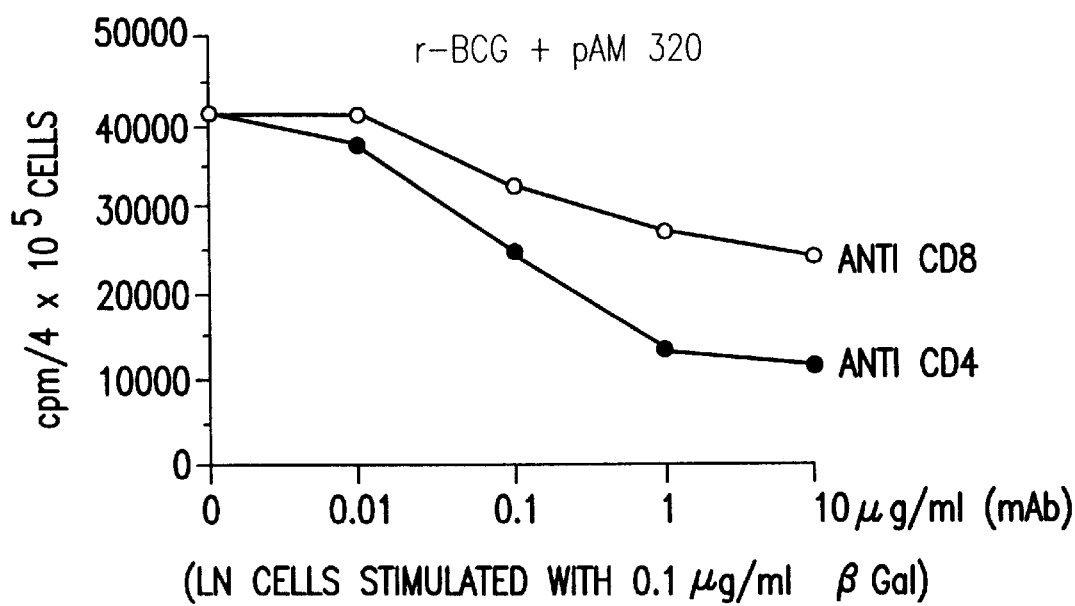

FIG. 5: Proliferation of specific CD4+ and CD8+ lymphocytes

Balb/c mice were immunized subcutaneously with 10 CFU of BCG 1173 P2 (a) and r-BCG+pAM320 b). Two weeks later the proliferative responses of their LN cells to PPD (10 μg/ml) (a) and beta-galactosidase (0.01 μm/ml) (b) were tested in the presence of anti-CD4 (O) or anti-CD8 (O) monoclonal antibodies.

Figure 6A:
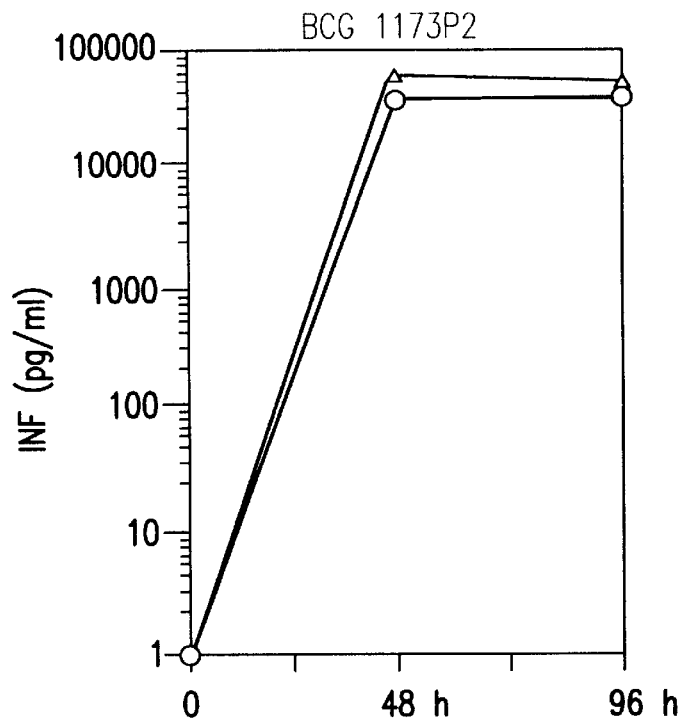
Figure 6B:
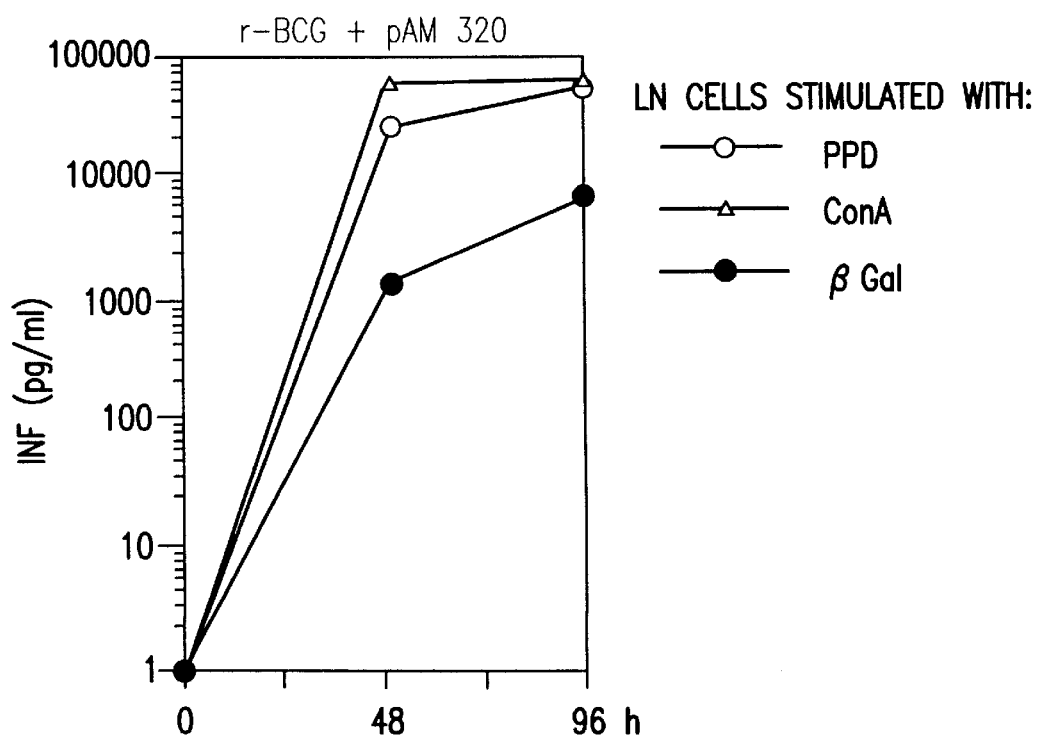

FIG. 6: Gamma-interferon responses of mouse LN cells.
a) mice immunized with BCG 1173P2
b) mice immunized with r-BCG (+pAM320) after stimulation with 1 μg/ml beta-gal (o), 10 μg/ml PPD (o), 2.5 μg/ml Con A (Δ).

FIG. 7: Cloning of the pan promoter (SEQ ID NO:5) adjacent to lacZ
PCR on pan
primers:

P1 =
5' CCCTCTAGAATTCCGTGACAAGGCCGAAGAGCCCGCGA 3'
(SEQIDNO:3)
P2 =
5' AACATATGAGATCTTCTCCTTCTGGGTTGGCCGCCCC 3'
(SEQIDNO:4)

PCR conditions: 35 cycles Denaturation for 2 minutes at 95° C. pairing for 2 minutes at 55° C., elongation for 2 minutes at 72° C. 50 μl reaction volume containing 10 μM of primers, 10 nmol of dNTP, the DNA target of pAM3.

Figure 8:
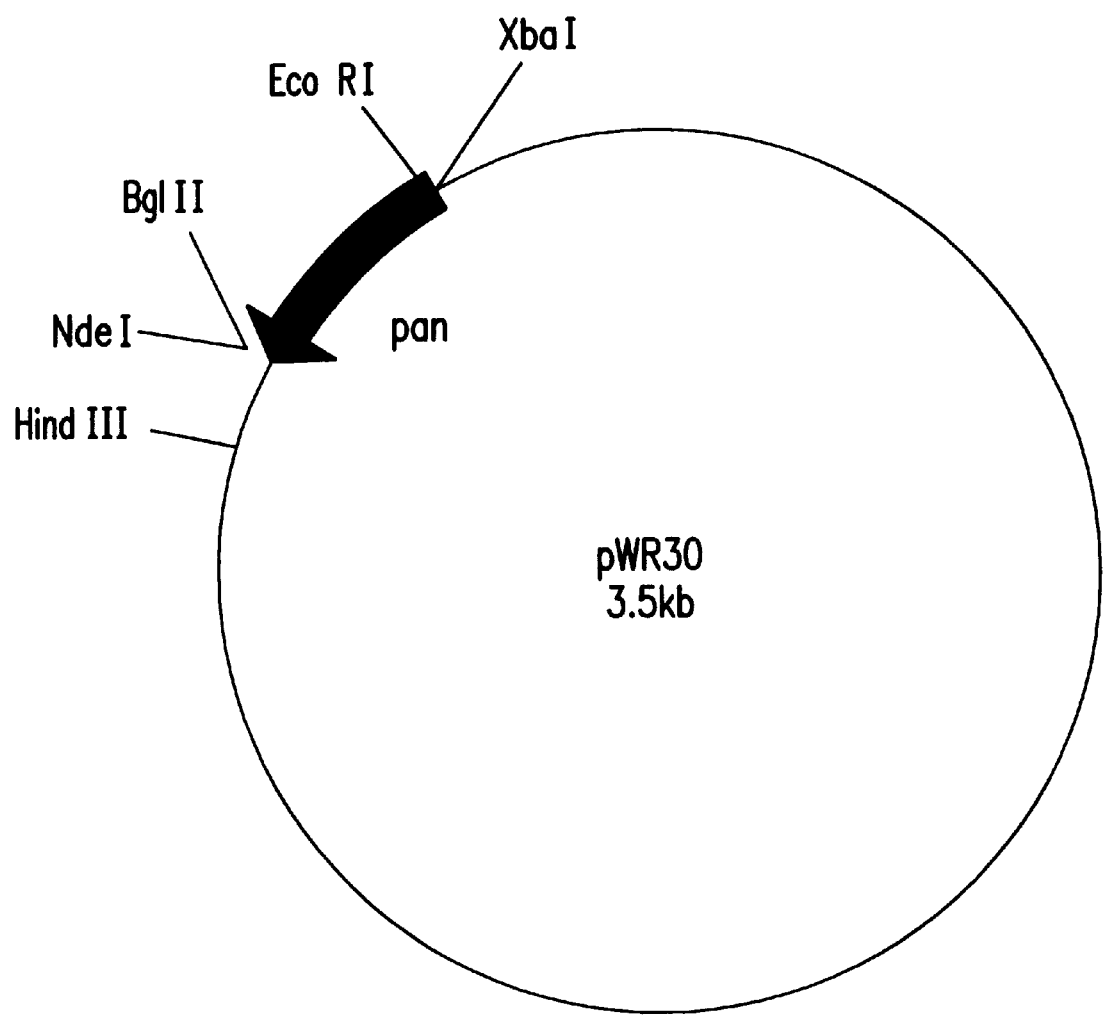
Figure 9A:
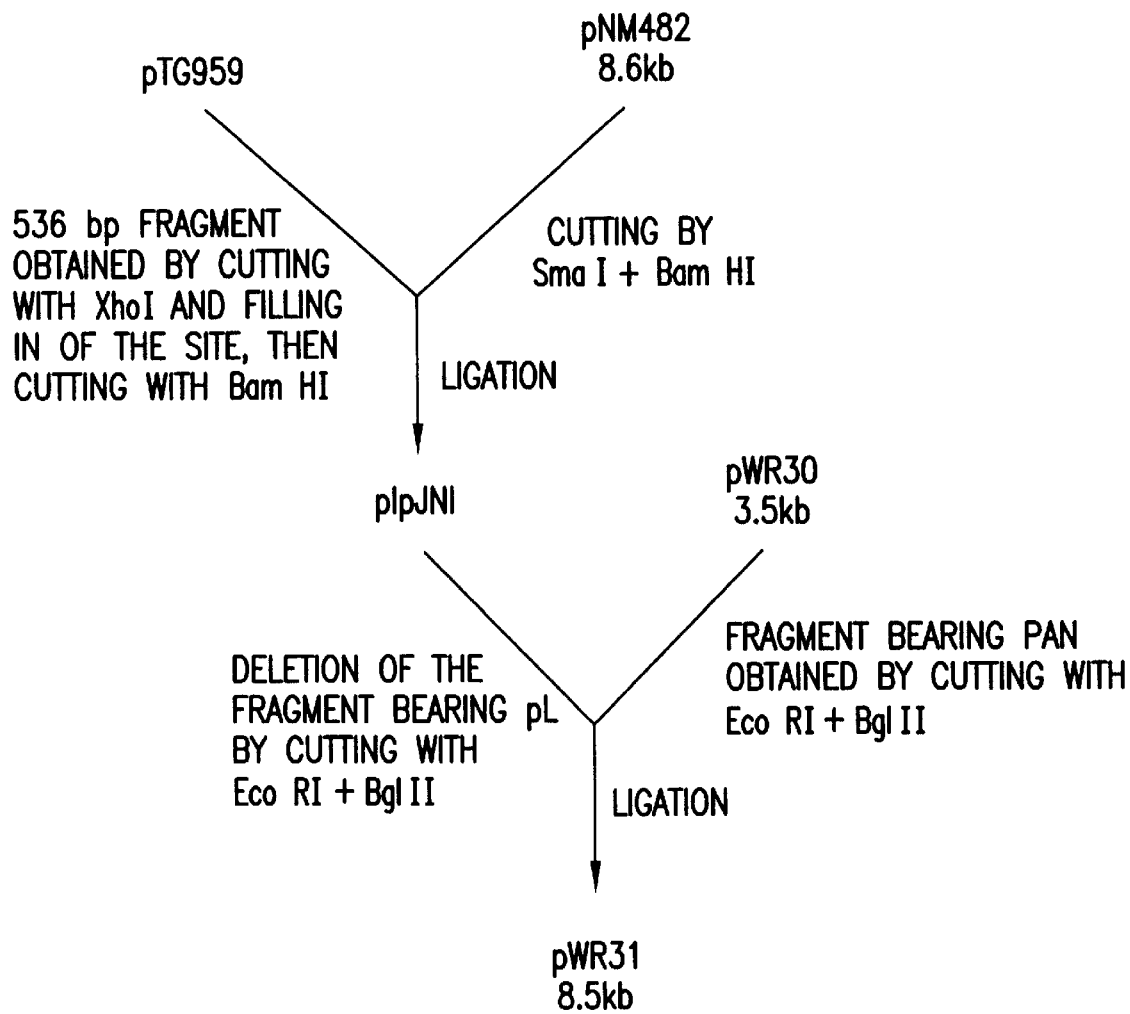
Figure 9B:
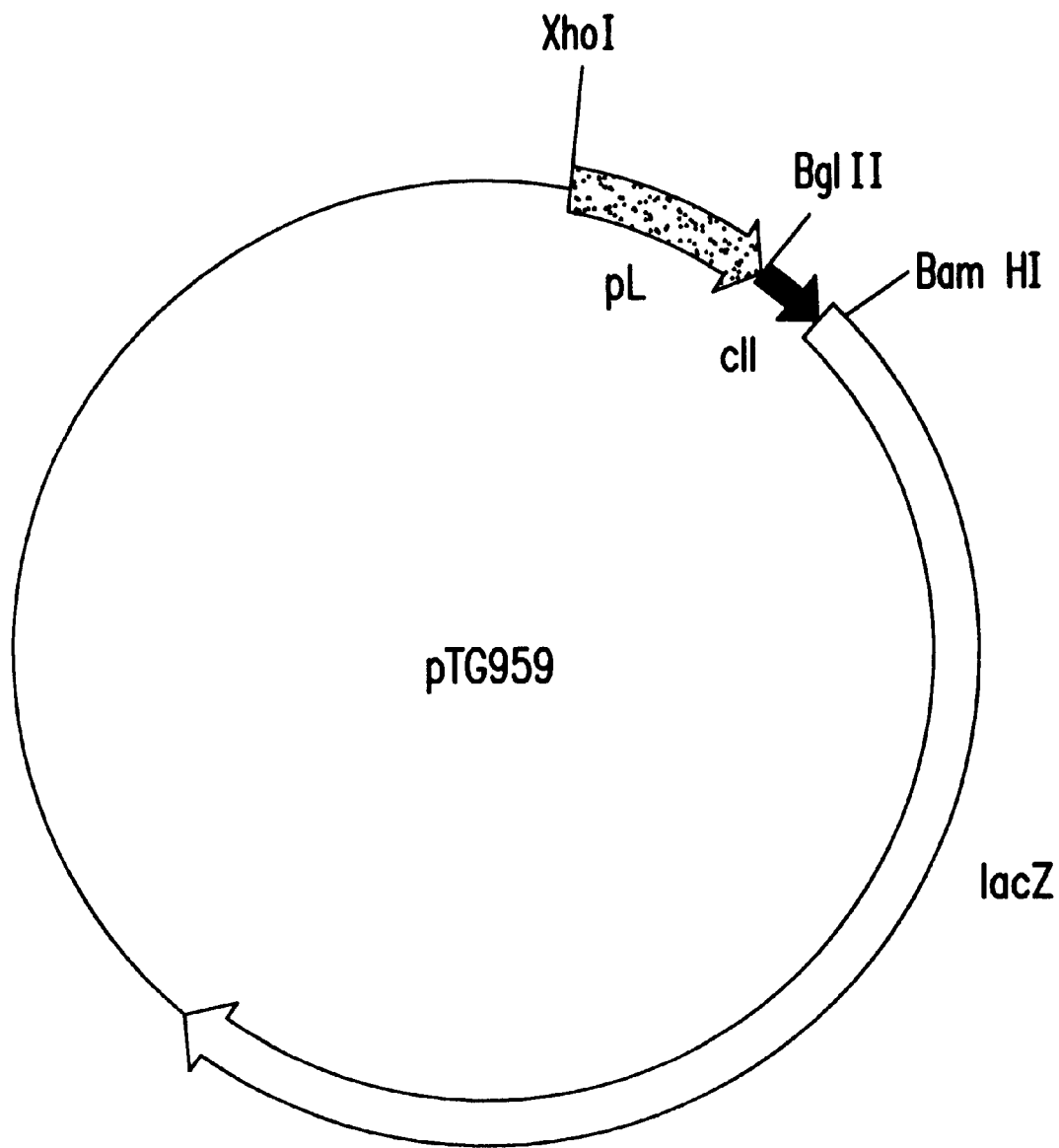
Figure 9C:
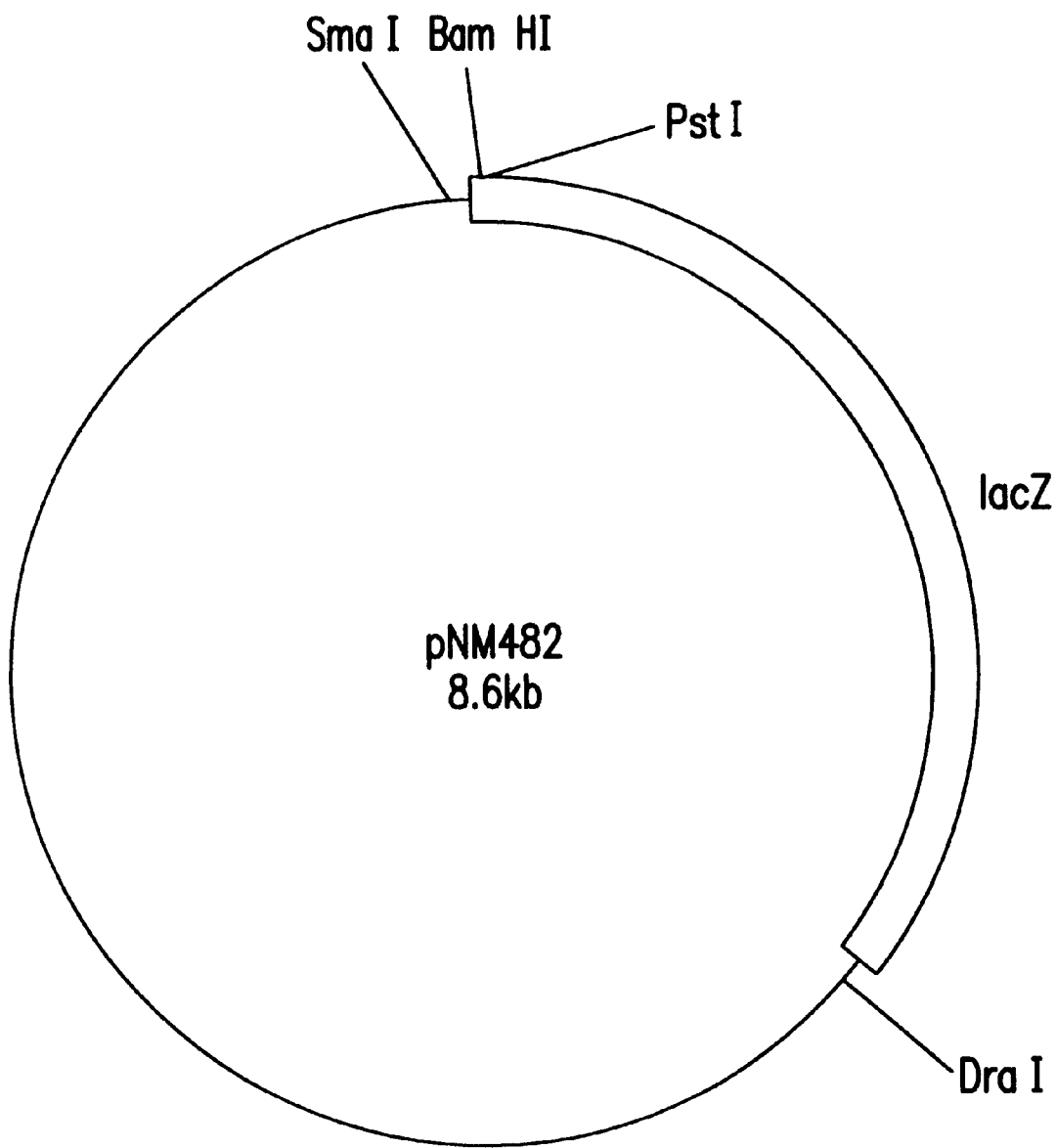
Figure 9D:
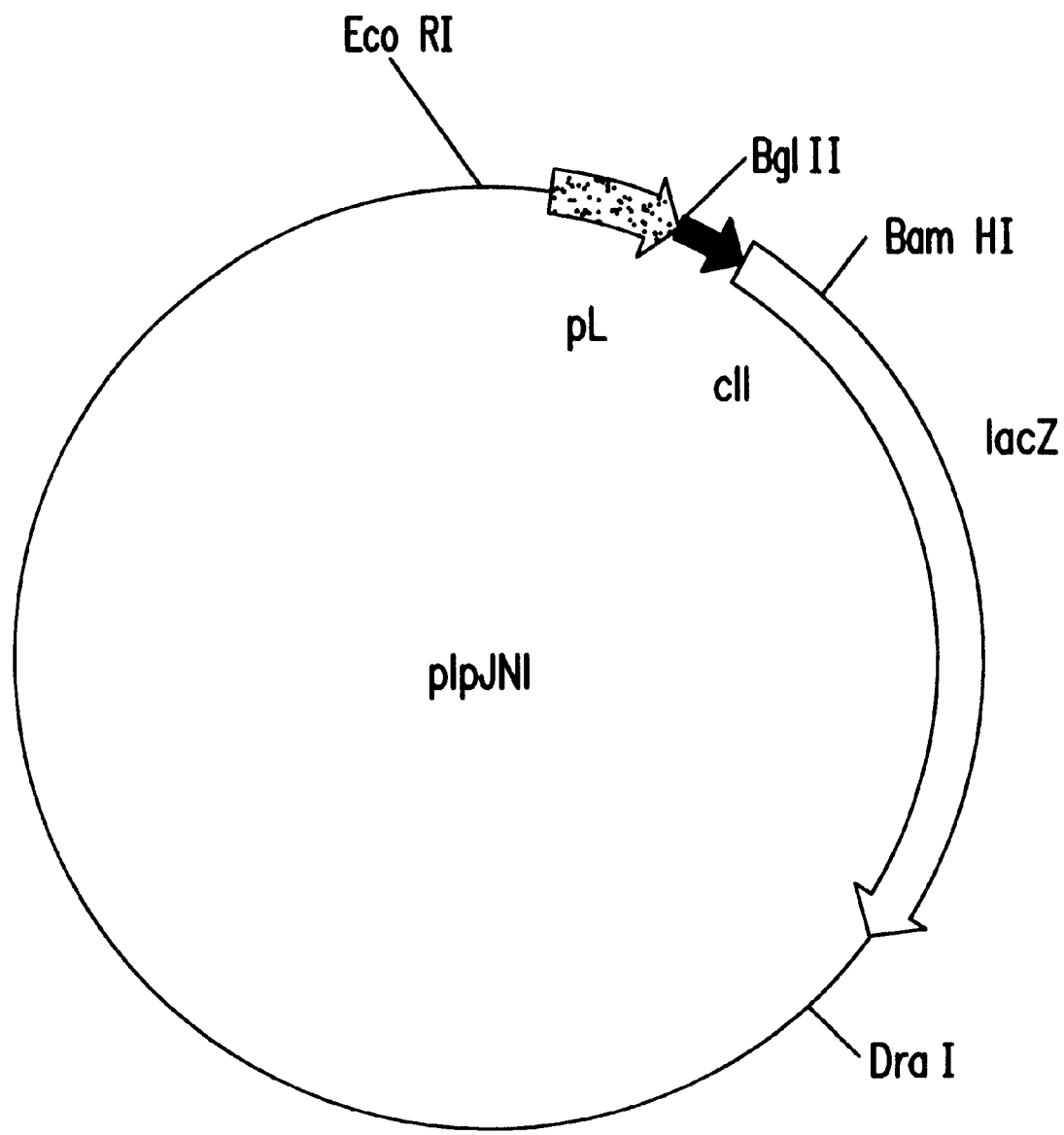
Figure 9E:
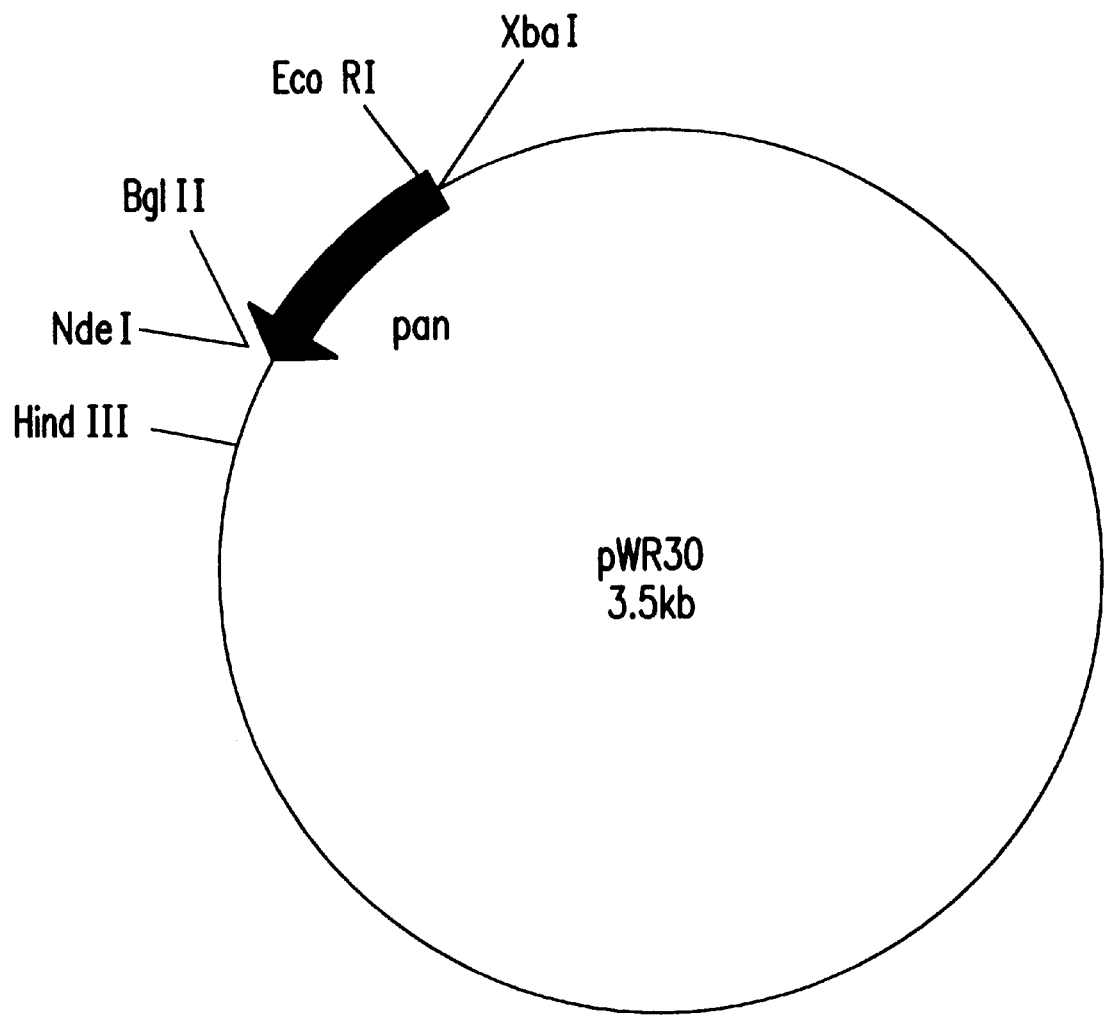
Figure 9F:
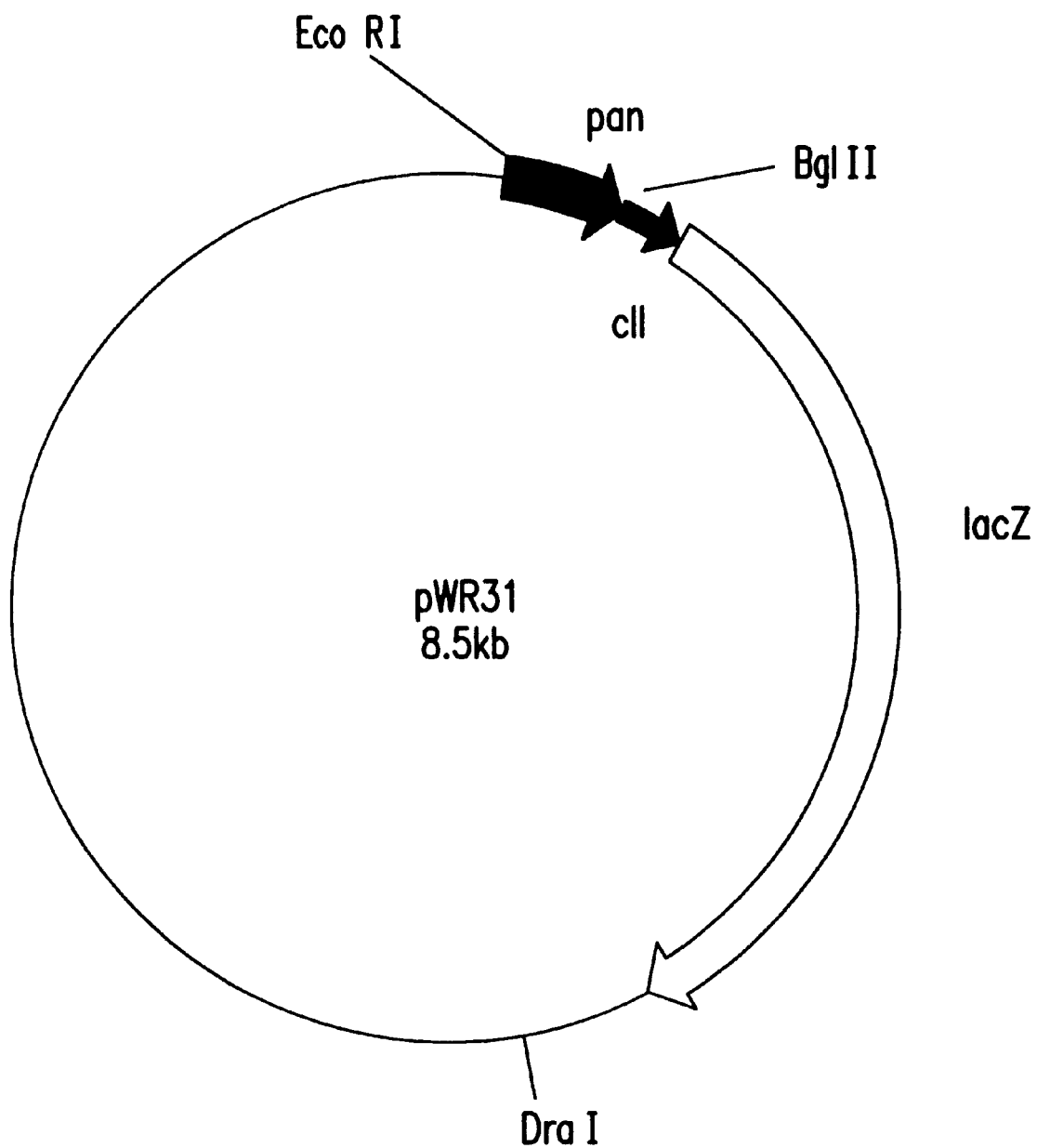
Figure 9G:
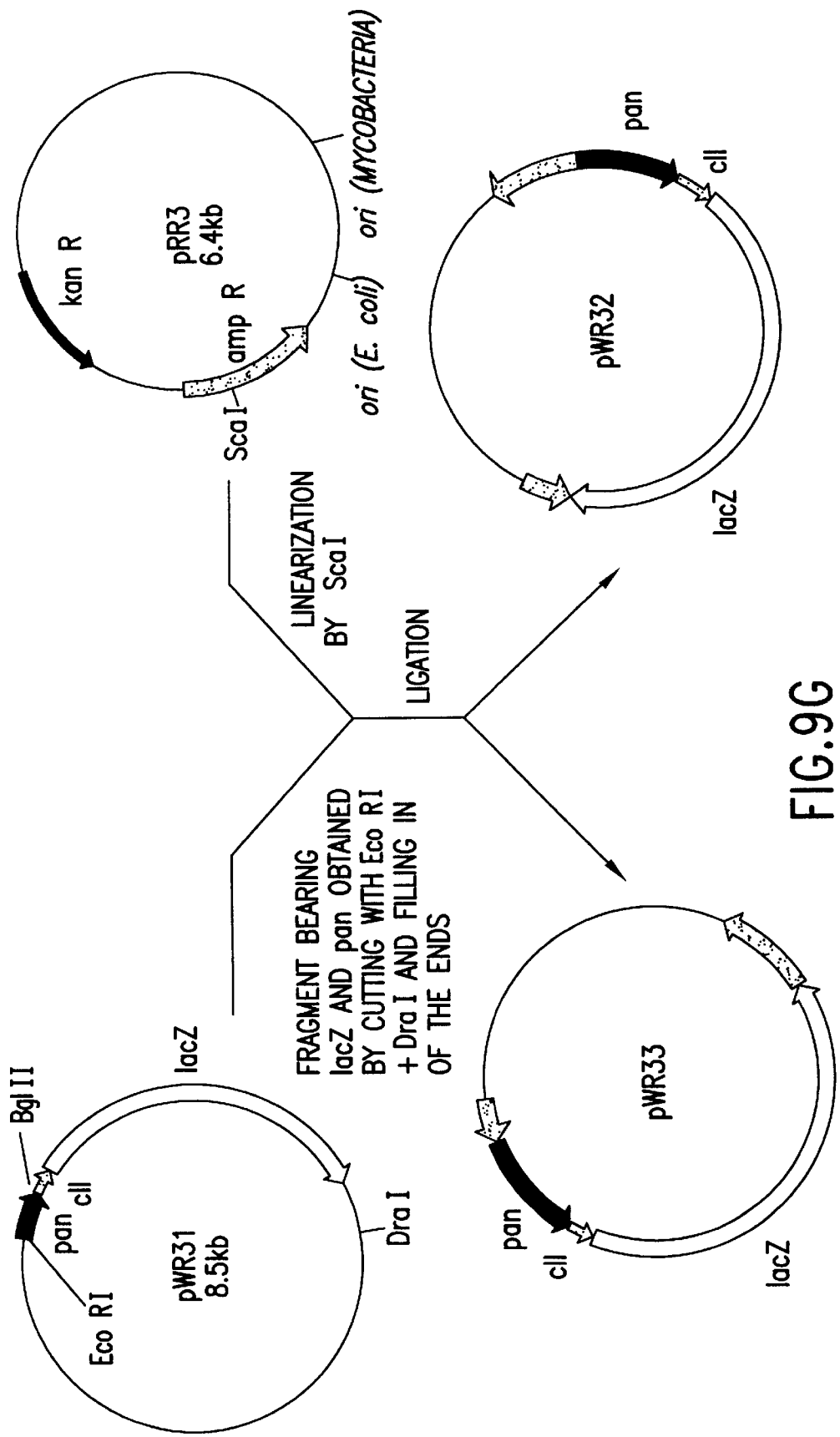

FIG. 8: Cloning of PCR product in MCS of pSL1180

The product obtained by PCR was digested with XbaI/NdeI and ligated to pSL 1180 (Pharmacia) digested with XpaI/NdeI to give pWR30

FIGS. 9a–9g: Schematic description of the construction of pWR31, pWR32 and pWR33

In the case of the FIGS. 7, 8, 9a and 9b: PCR (gene amplification) was used to produce a 716 bp fragment from pAM3 using the primers P1 and P2. This fragment contained the pan promoter with XbaI and EcoRI sites at the 5' end and BglII and NdeI sites at the 3' end. The fragment was digested with XbaI and NdeI and cloned into the multiple site (MCS) of pSL1180 to form the plasmid pWR30. During the preparation for the cloning of pan into a site adjacent to the lacZ gene, the pL promoter and the CII gene were doned in front of the truncated lacZ gene of pNM482. This makes it possible to generate a functional CII-LacZ fusion protein under the control of sequences upstream containing pL as well as a polylinker making possible subsequent constructions. The plasmid pTG952 was also digested with XhoI and its end filled up using the Klenow fragment. A 530 bp fragment was then recovered from the plasmid after digestion with BamHI and cloned into the SmaI/BamHI site of pNM482. The resulting plasmid pIPJN thus possessed a functional beta-galactosidase gene under the control of the pL promoter of lambda. In order to clone pan in pIPJN pWR30 was digested by EcoRI/BglII. The 159 bp fragment was purified using Geneclean and cloned into pIPJN digested by EcoRI/BglII to give pWR31. When the *E. coli* strains were transformed with this plasmid and grown in the presence of ampicillin and X-gel, blue colonies were formed. The fusion operon was then recovered from pWR31 by digestion using EcoRI/DraI. The EcoRI site was filled up using the Klenow enzyme and dNTPs, then ligated to the plasmid pRR3 digested by the enzyme ScaI. The two orientations of the operon in pRR3 were obtained. The transformation of *E. coli* and *M. smegmatis* with these two constructions (pWR32, pWR33) gave rise to the formation of blue colonies when bacterial were grown in the presence of an X-gal chromogenic substrate.

FIG. 10: Sequence of ORF2 (SEQ ID NO:8)

Figure 11:
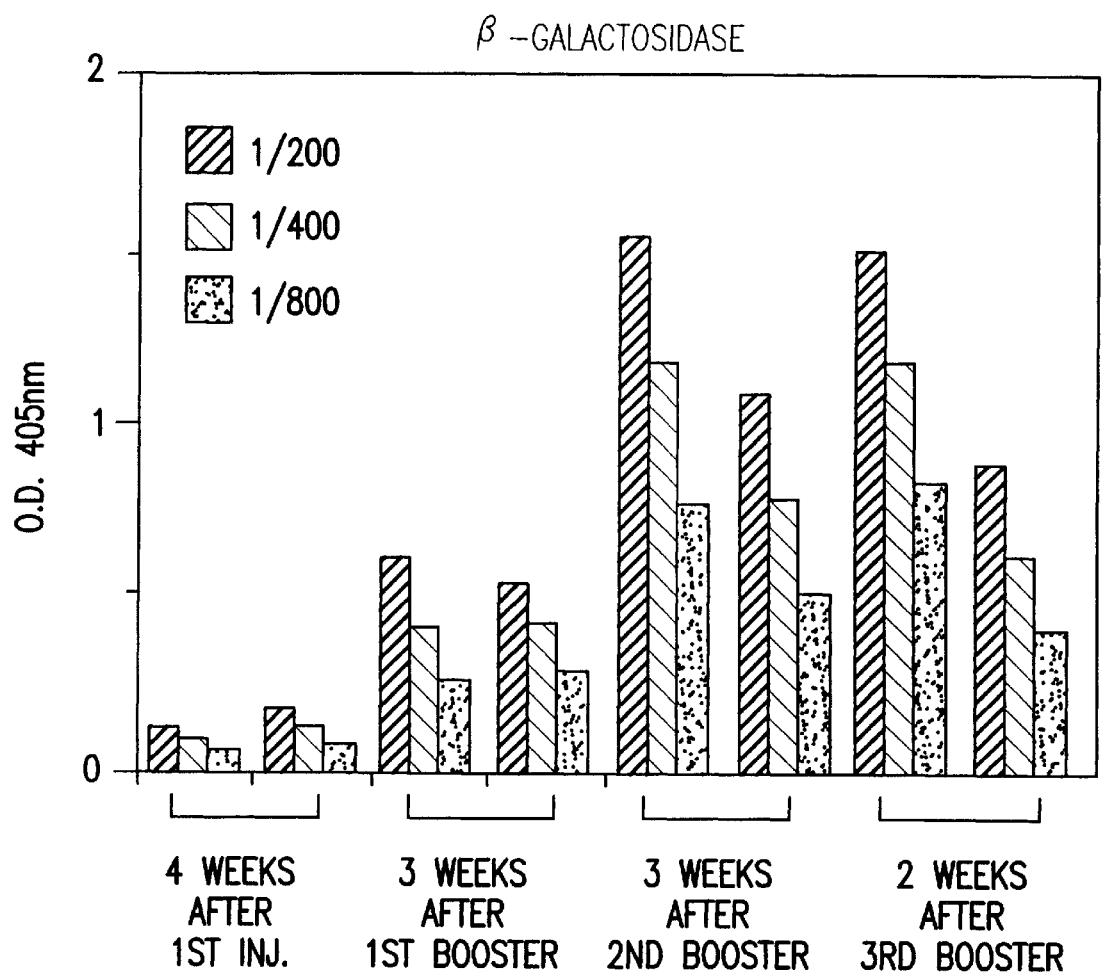
Figure 12A:
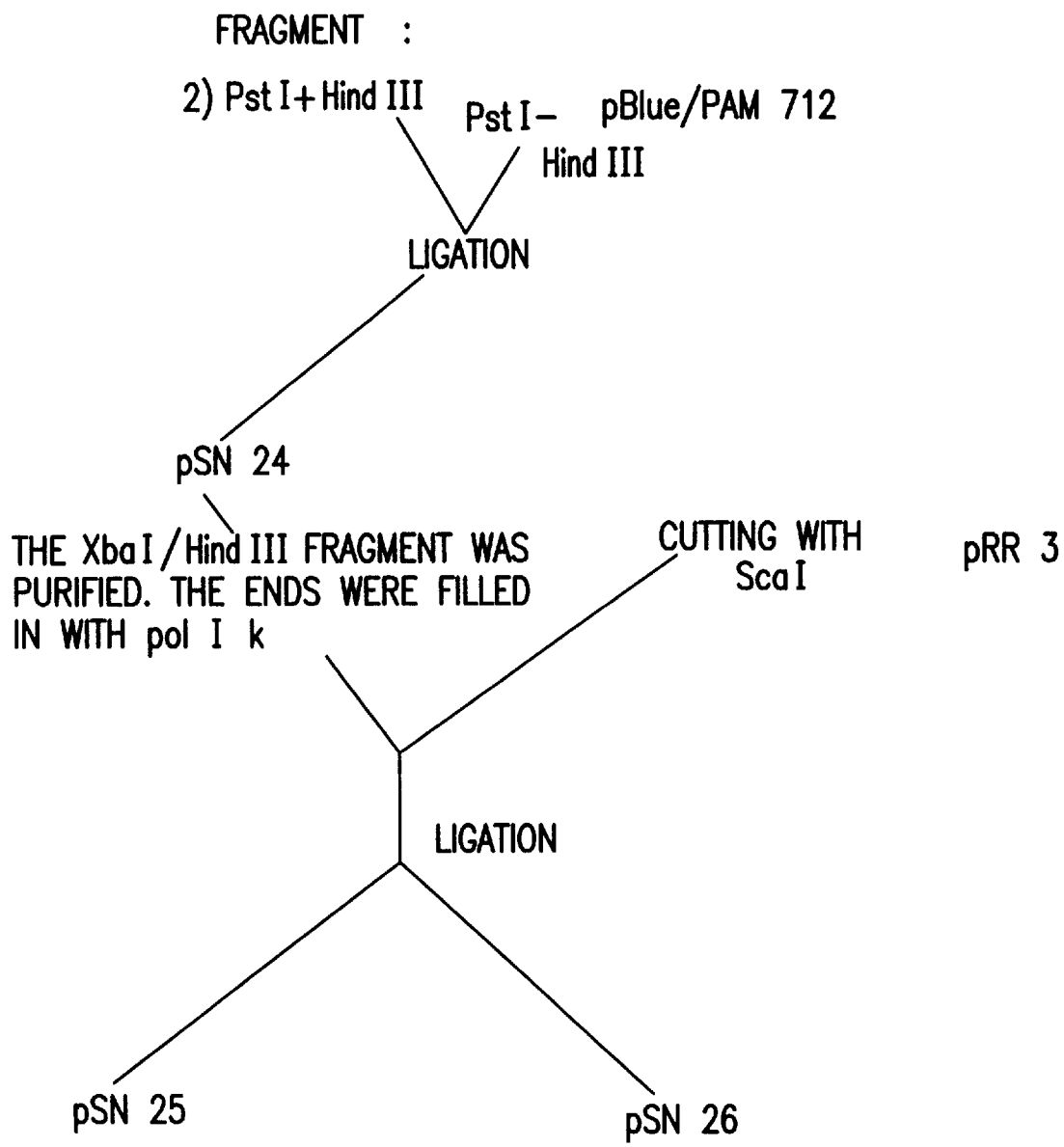
Figure 12B:
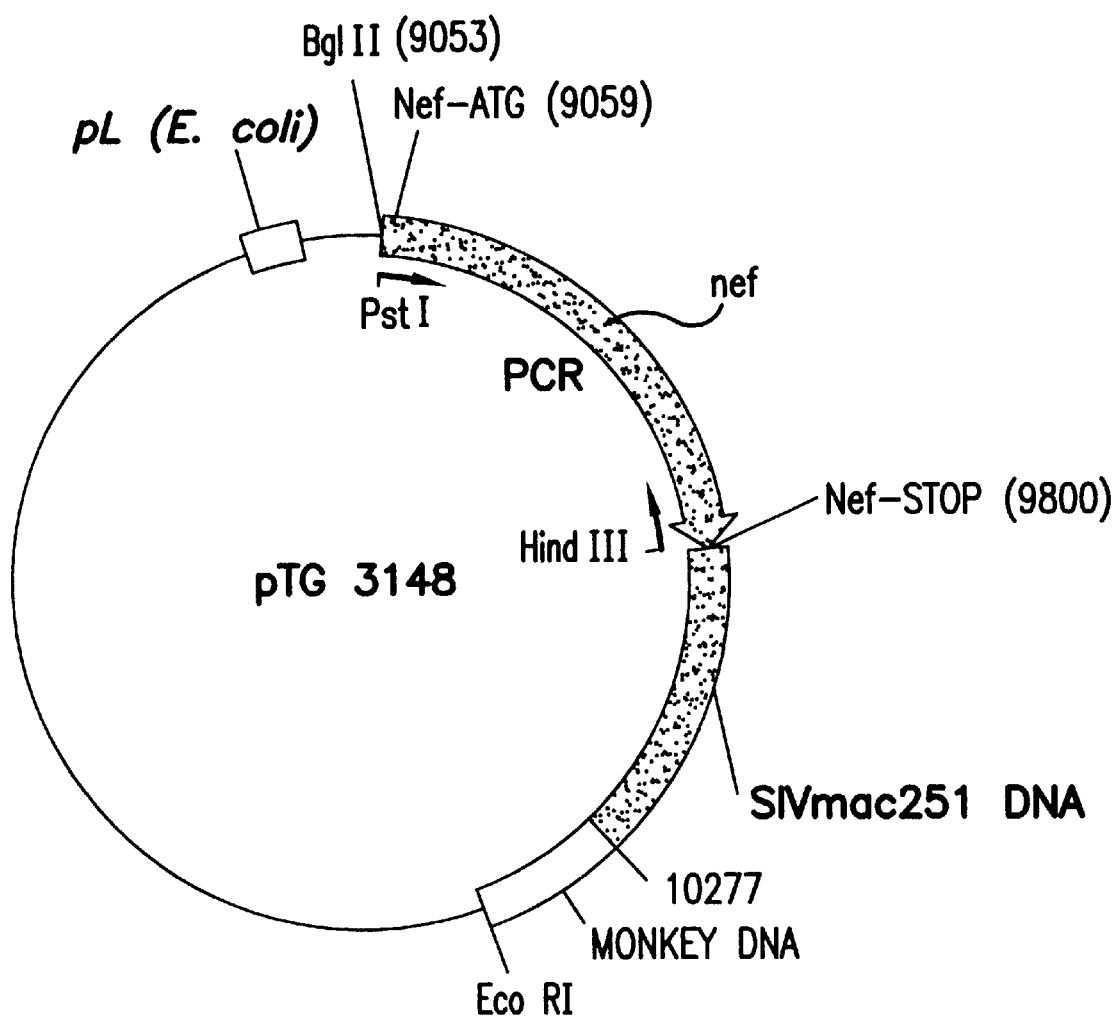
Figure 12C:
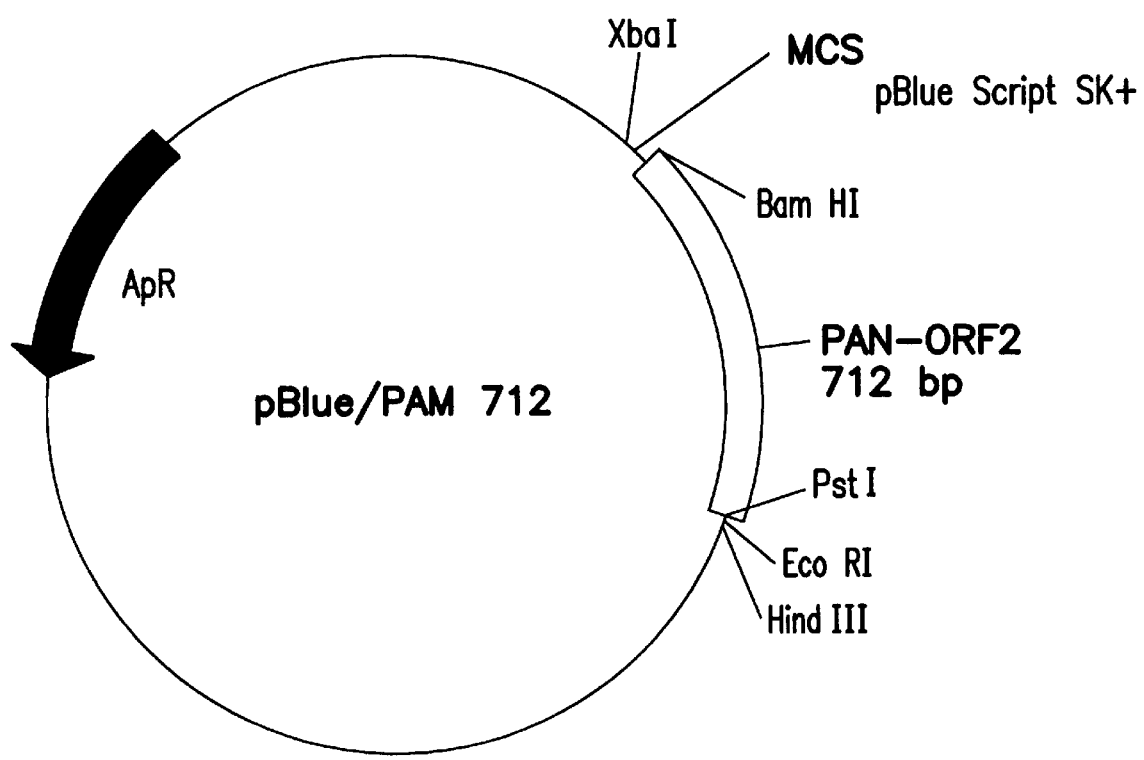
Figure 12D:
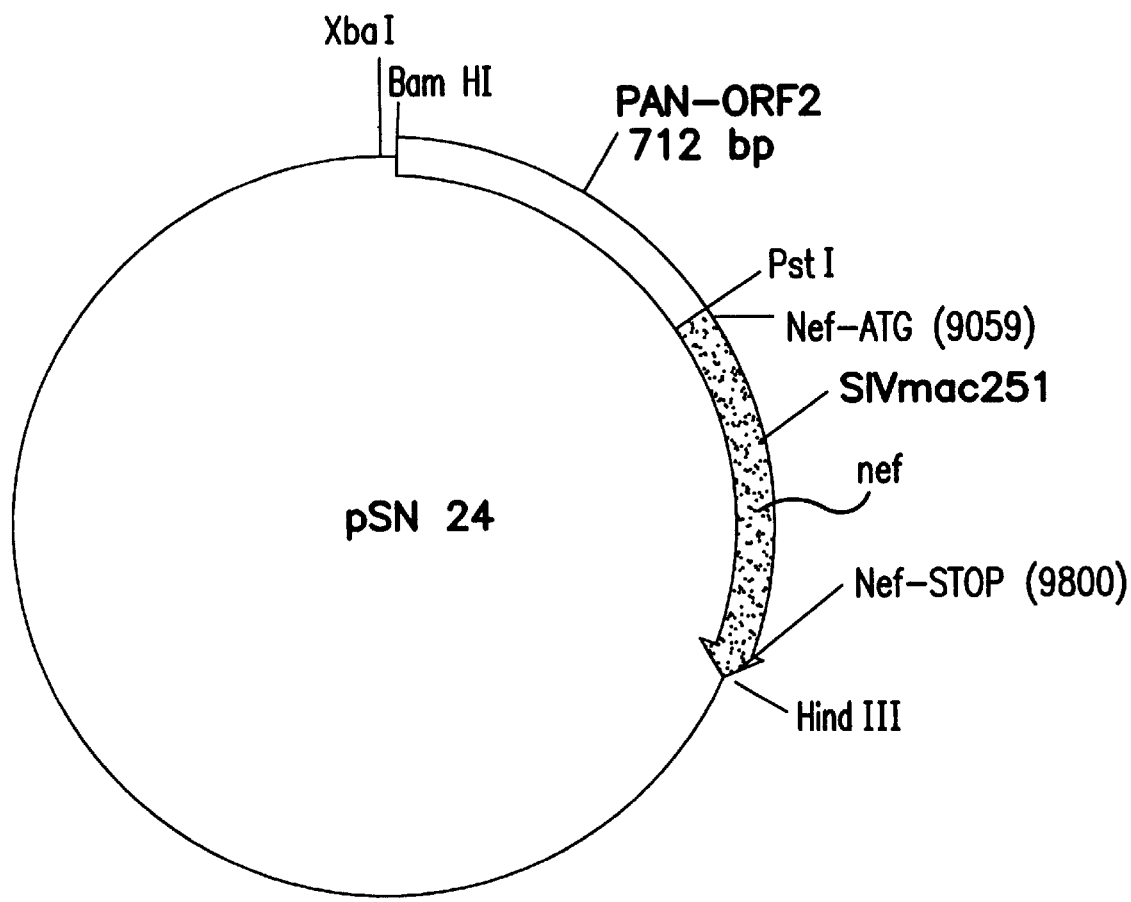
Figure 12E:
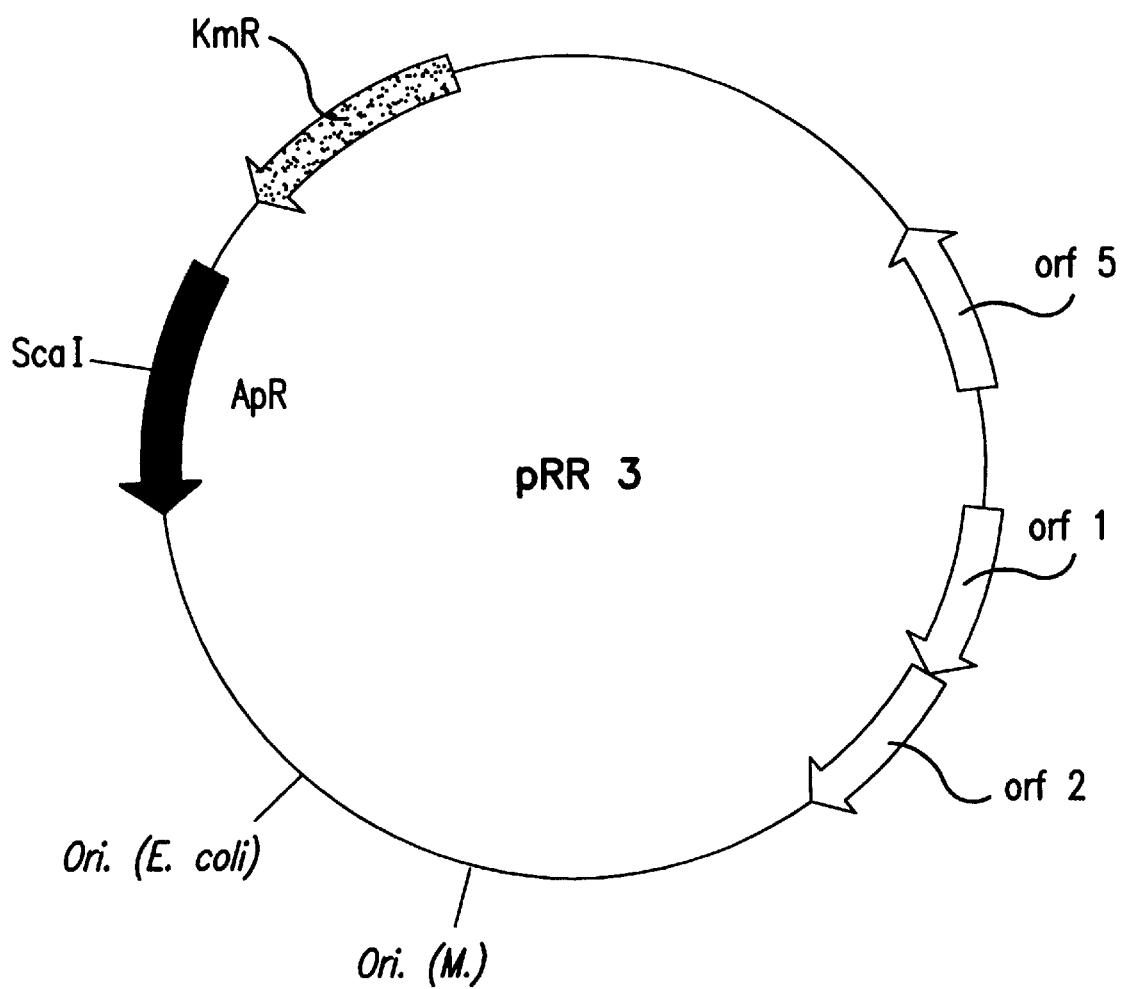
Figure 12F:
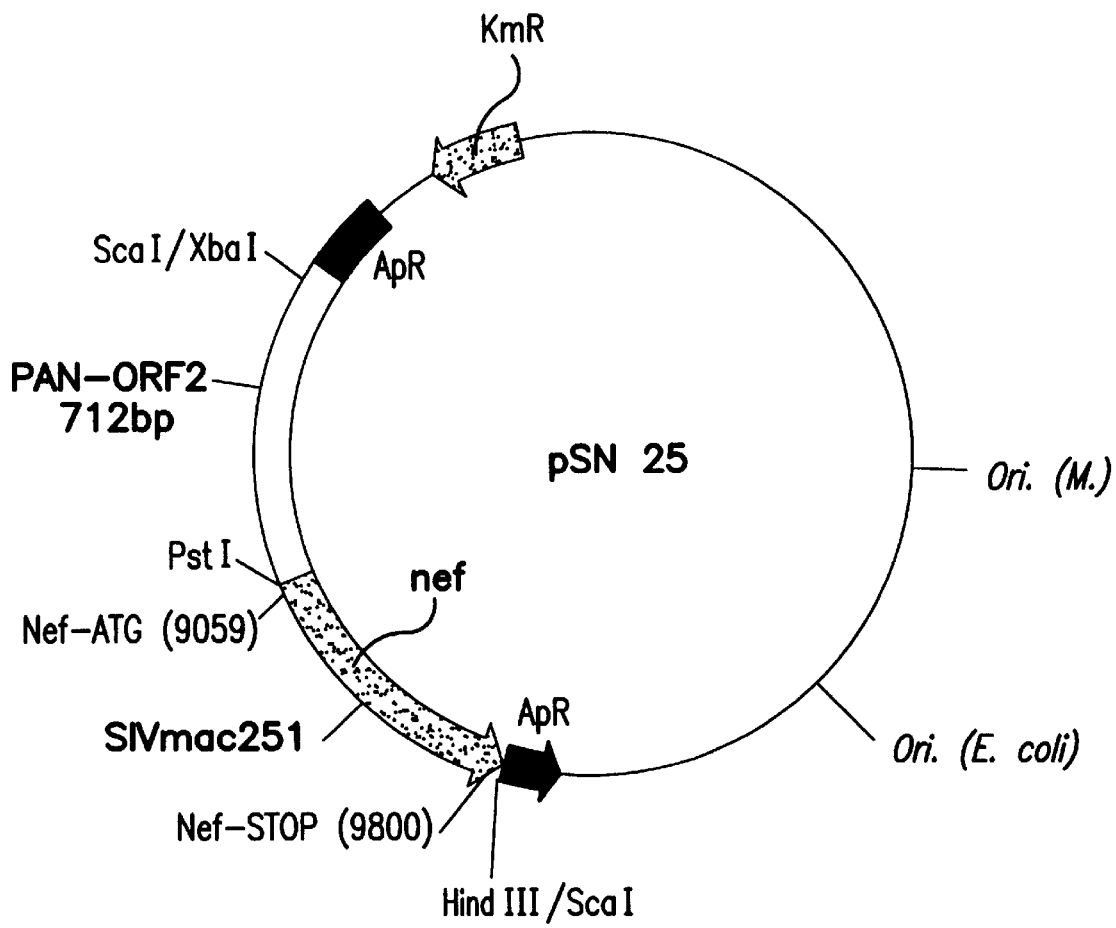
Figure 12G:
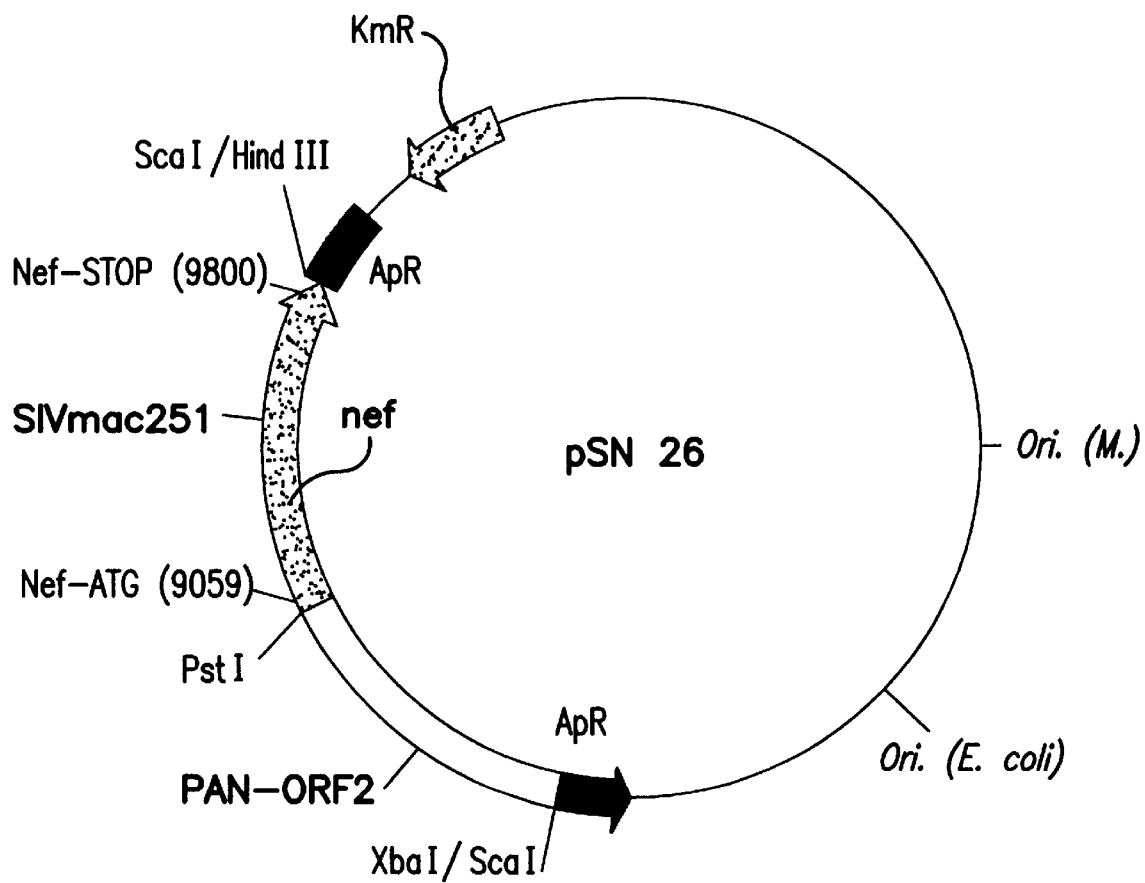

FIG. 11: Antibody response in the sera of animals immunized with the r-BCG expressing beta-galactosidase.

FIG. 12: Construction of the plasmids containing the fusions pAN-ORF2-Nef (SIV). The plasmid pTG3148 is a vector derived from pTG959 (Guy et al., 1997 Nature 330: 266–269) into which a BglII fragment containing the nef gene has been cloned. This fragment was isolated from monkey cells containing the SIV virus (mac251) integrated as provirus. The plasmid pBlue/pAM721 is derived from pBluescriptIISK+ (Stratagene) in which the BamHI/PstI fragment containing pAN-ORF2 excised from pAM1 was cloned between the BamHI and PstI sites of the polylinker.

Figure 13:
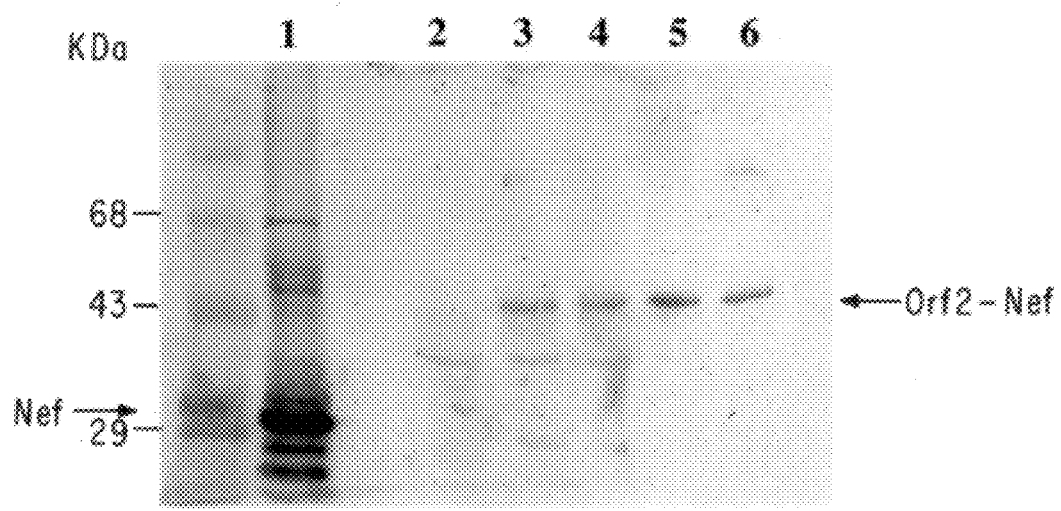

FIG. 13: Western blot type analysis of the expression of the polypeptide ORF2-Nef (SIV). The molecular weight markers are show to the left of lane 1; Lane 1: Extract of BCG; Lanes 3 to 4: Two extracts of recombinant BCG carrying the plasmid pSN25; Lanes 5 and 6: Two extracts of recombinant BCG carrying the plasnmid pSN26.

Figure 14:
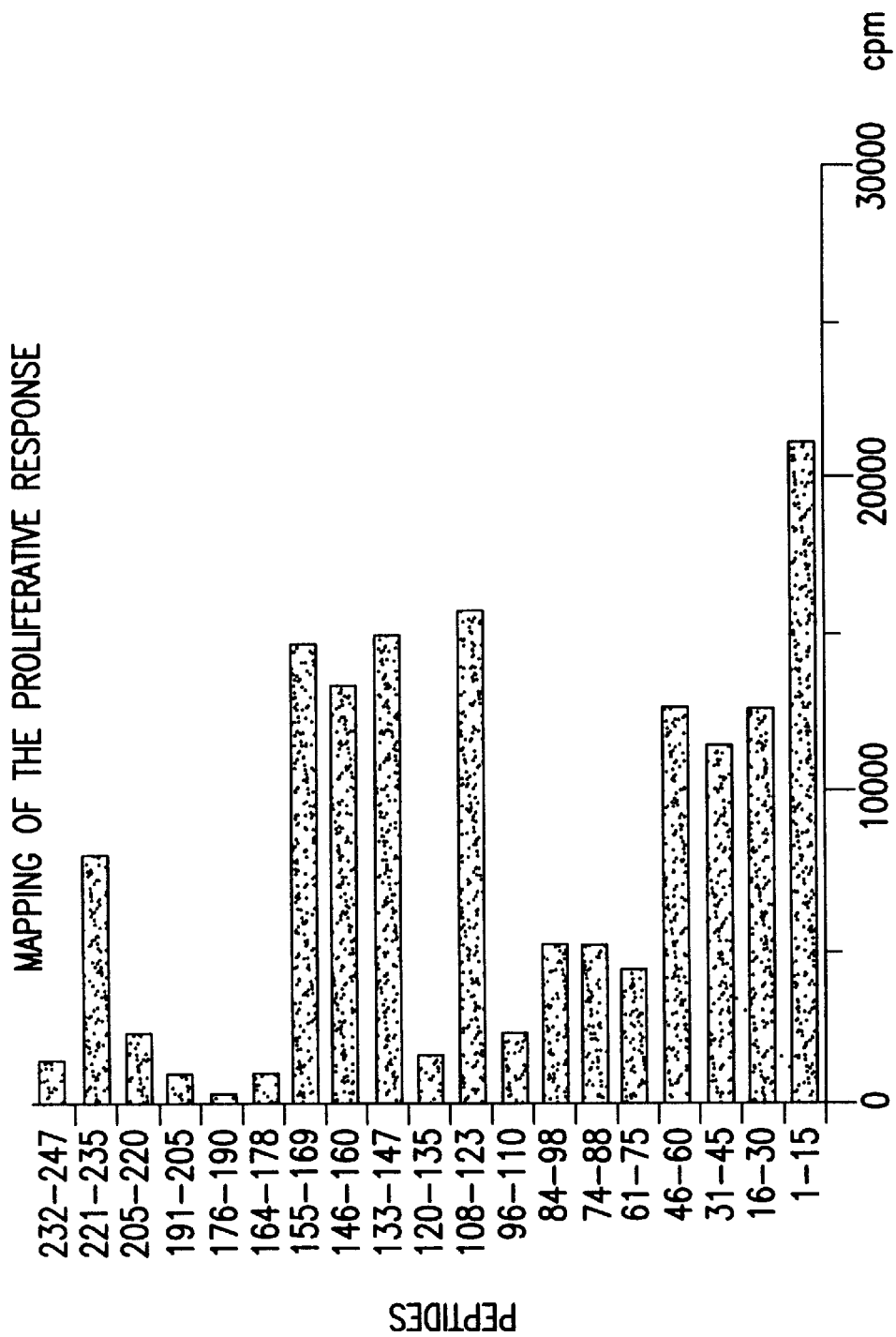

FIG. 14: analysis of the proliferative responses of cells taken from the lymph nodes of Balb/c mice inoculated with recombinant BCG bearing the plasmid pSN25. The immunization protocols are the same as those described at the Cold Spring Harbor conference (Vaccine, September 1991) and repeated in Winter et al., 1991 (Gene 109: 47–54). The proliferation was measured after in vitro stimulation with the different peptides shown along the ordinate in FIG. 3 as a function of their localization on the protein (from the N- to the C-terminus). Three peptide concentrations were used (0.1, 1 and 10 μg/ml). the proliferation maximum was observed at one or other of these concentrations, depending on the peptide. This is the maximal value which is shown in FIG. 3. Similarly, the proliferation was measured starting from mice immunized with non-recombinant BCG. The values obtained were always lower than 2500 cpm (except in the case of stimulation with the peptide 84–96 where a value of 5000 cpm was observed). The experiments performed with unimmunized rats gave values lower than 250 cpm.

Figure 15:
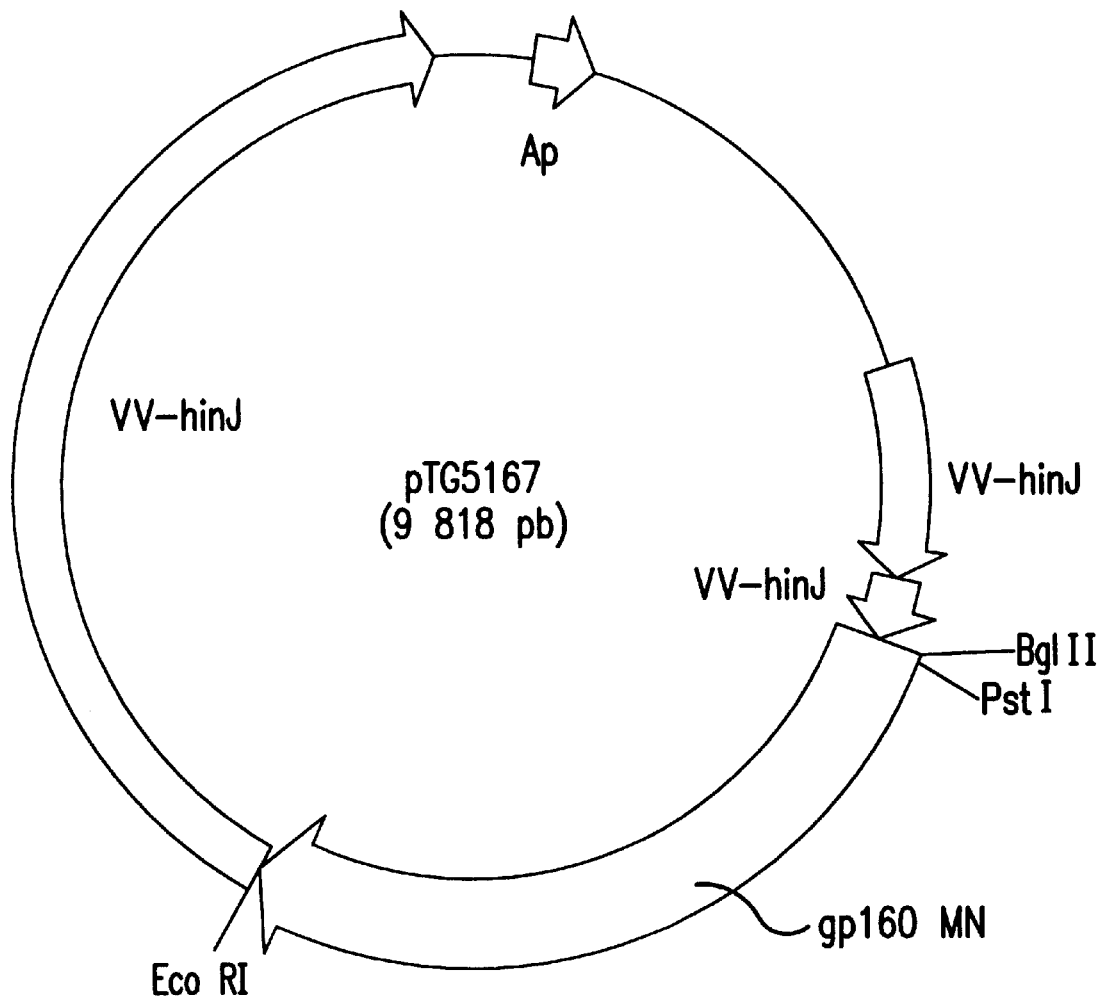
Figure 16A:
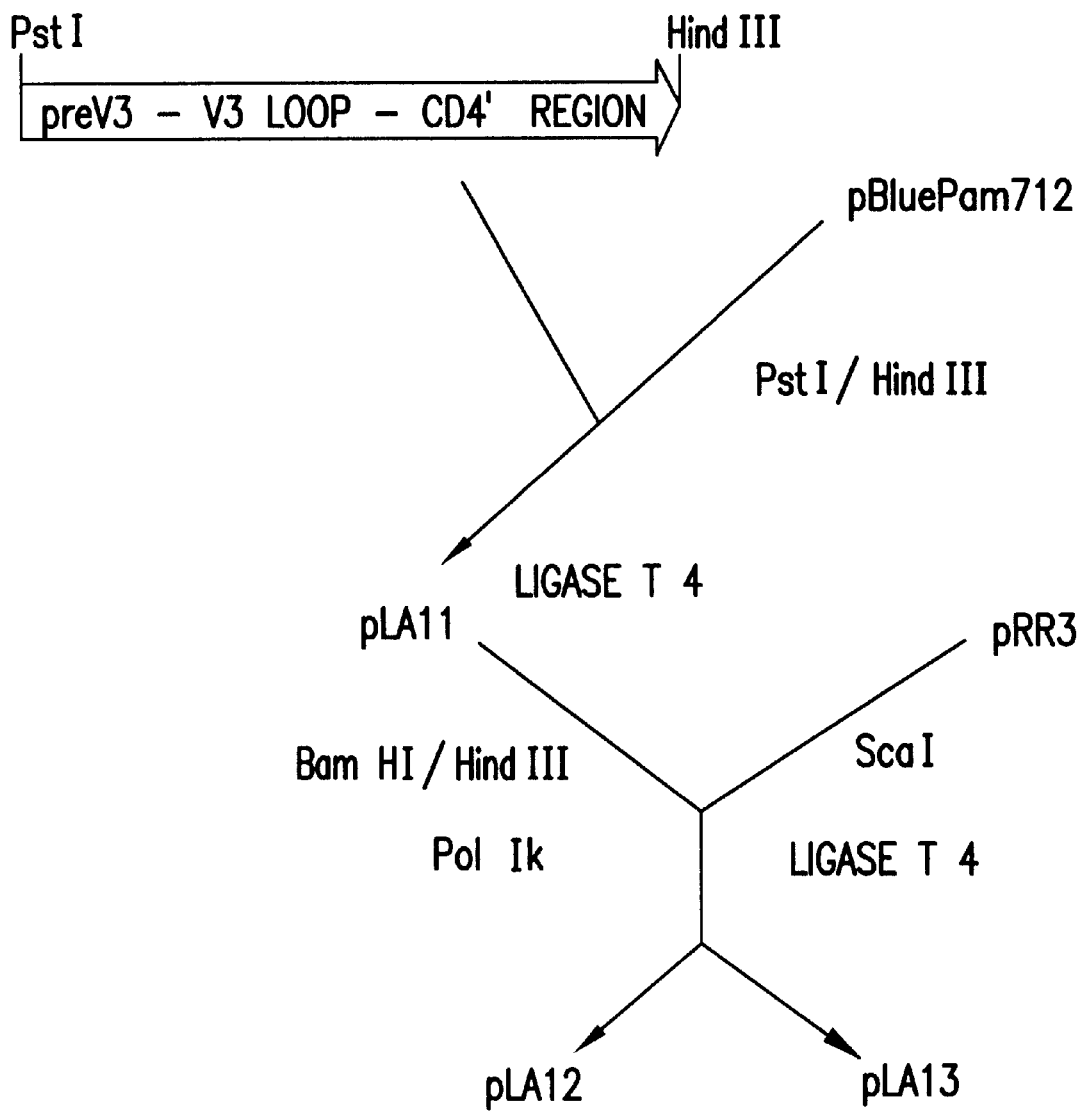
Figure 16B:
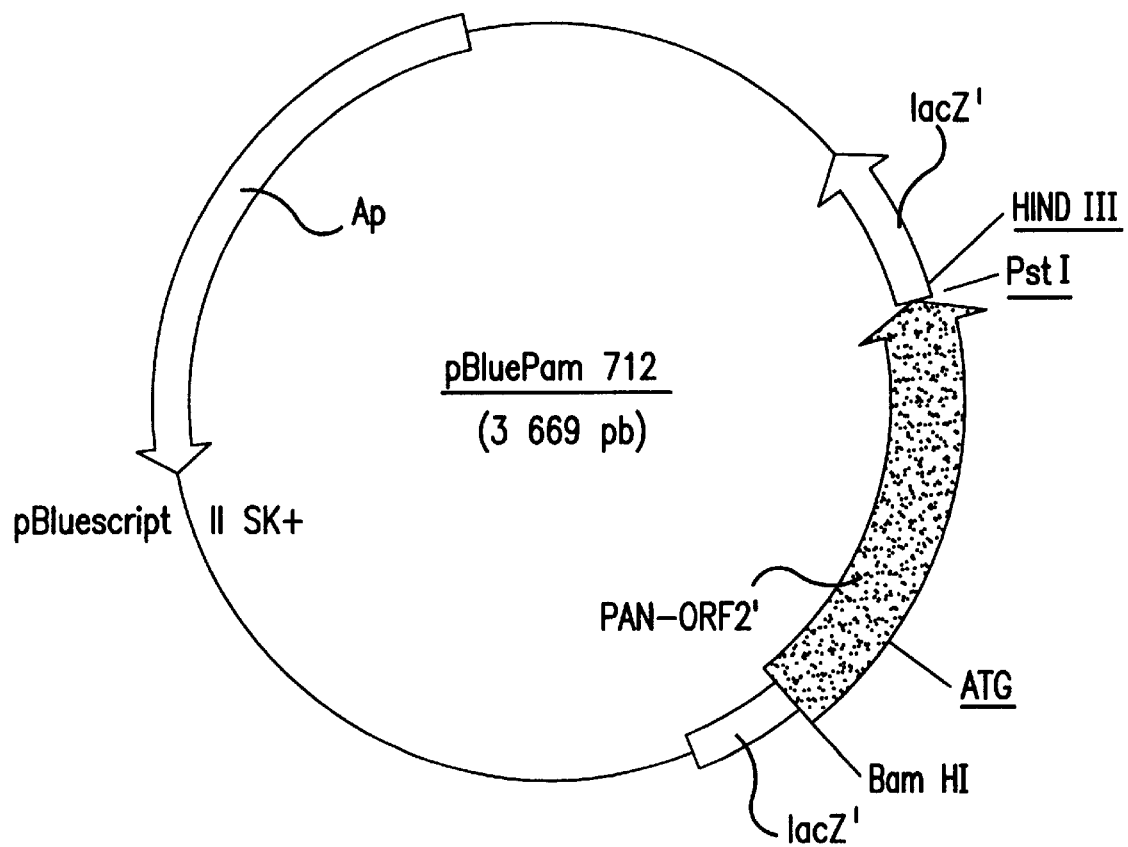
Figure 16C:
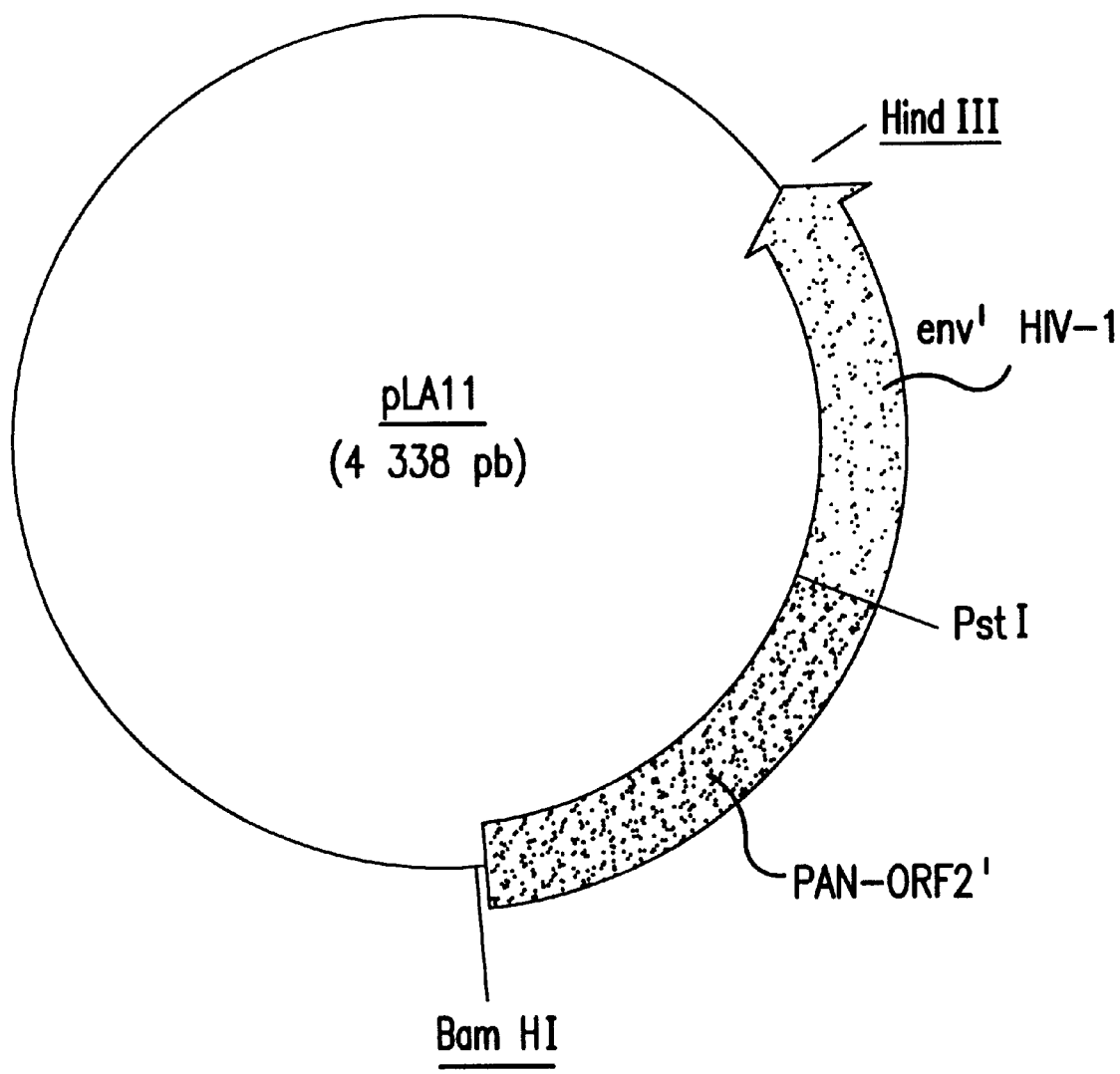
Figure 16D:
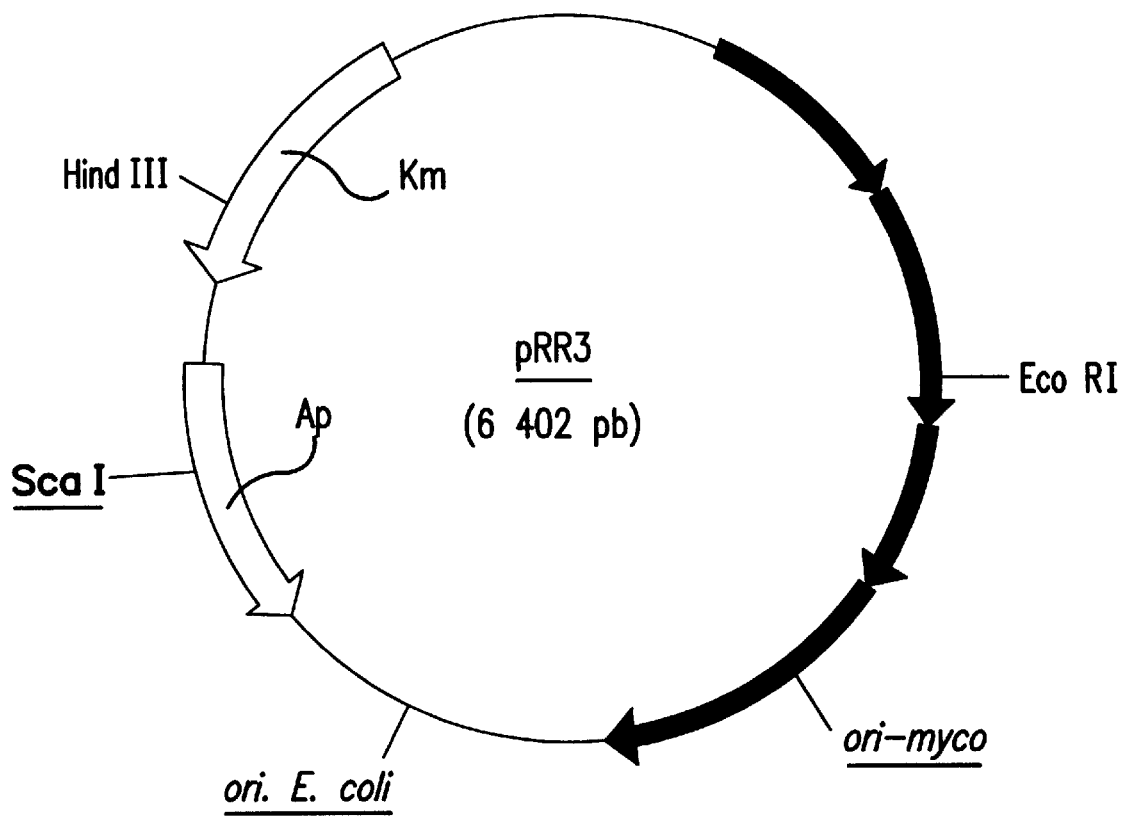
Figure 16E:
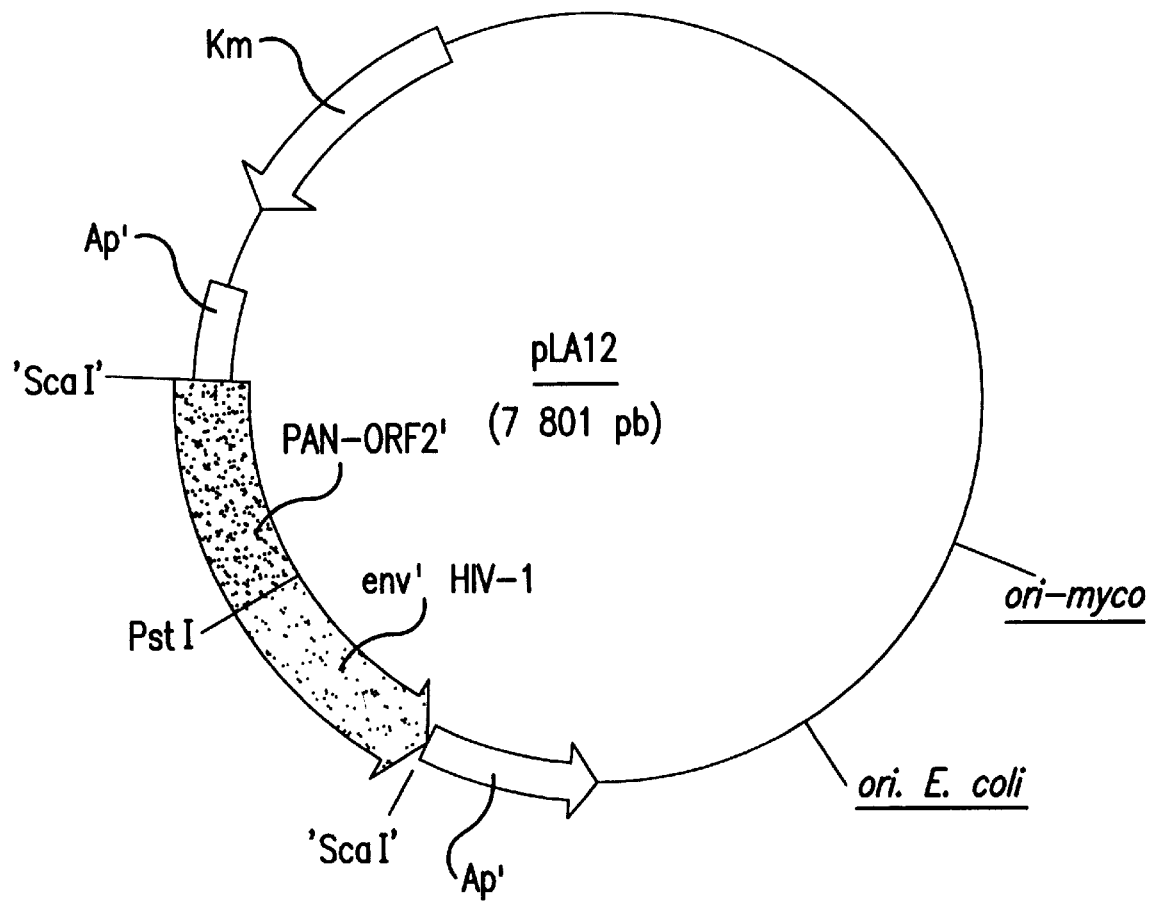
Figure 16F:
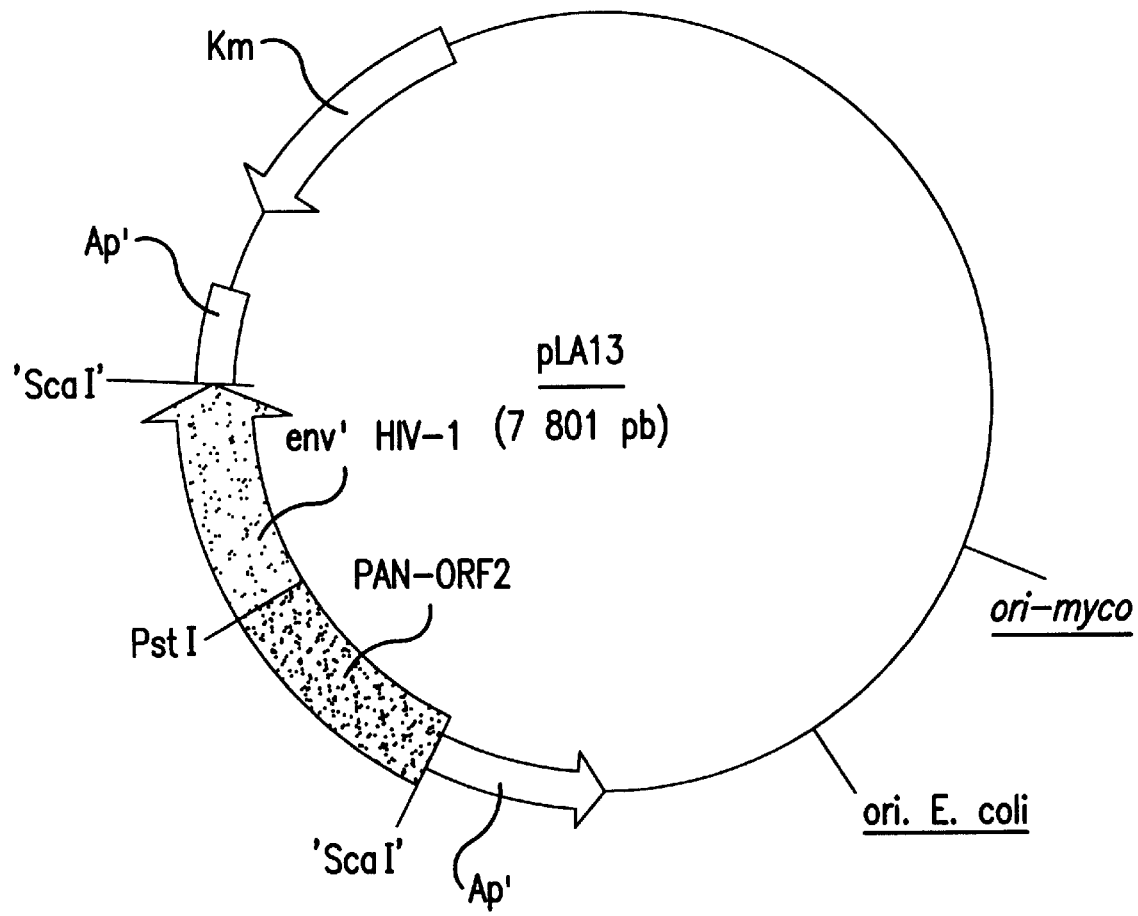

FIG. 15: Plasmid pTG5167. This is a derivative of pTG186 poly (Guy et al., 1987) in which a BglII-EcoRI fragment bearing the gene coding for the gp160 of protein HIV-1/MN was cloned in the polylinker.

Figure 17:
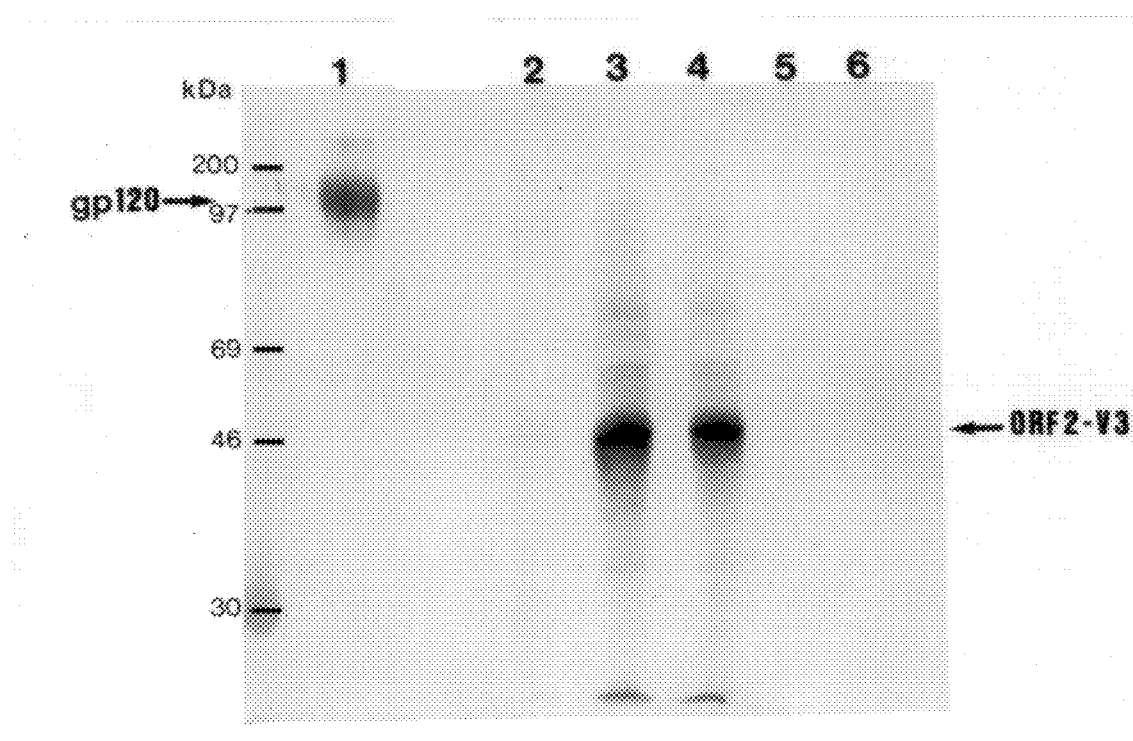
Figure 18A:
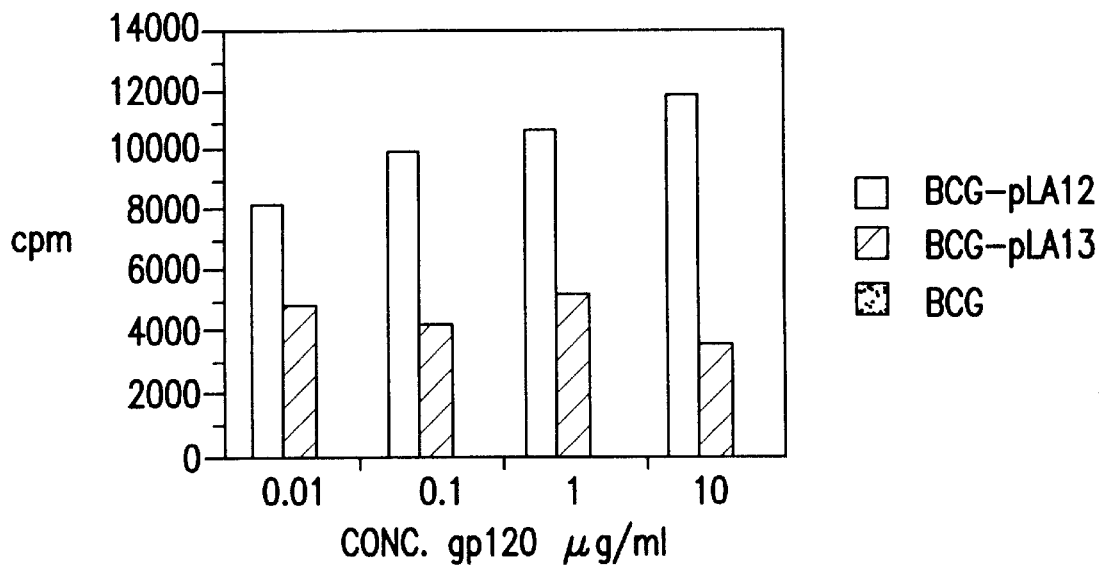
Figure 18B:
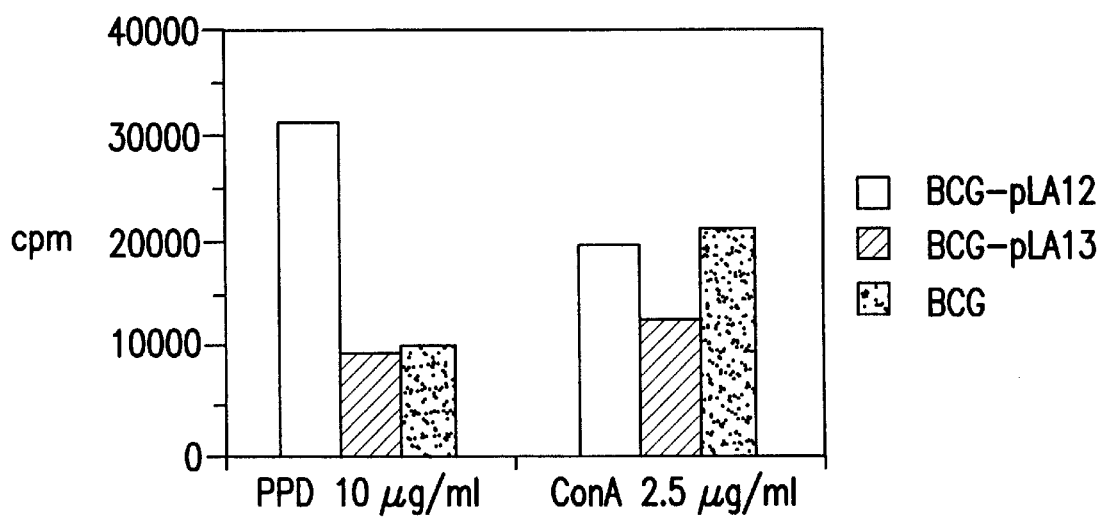

FIG. 16: Construction of the palsmids pLA12 and pLA13 bearing the fusion pAN-ORF2-Env (HIV-1/MN FIG. 17: Expression of the polypeptide ORF1-Env (HIV-1/MN by the BCG bearing the plasmids pLA12 and pLA13. 1: protein gp120 of HIV-1 FA1; 2: BCG standard cell extract; 3: BCG-pLA12, cell extract; 4: BCG-pLA13 cell extract; 5: BCG-pLA12, culture supernatant; 6: BCG-pLA13, culture supernatant. FIG. 18: Proliferative responses of the cells extracted from the lymph nodes of mice inoculated with the BCG bearing the plasmids pLA12 and pLA13.

4 Balb/c mice receive an intrdermal injection of $10^7$ CFU of BCG-pLA12, 4 others receive BCG-pLA13 and 4 more receive BCG 1173P2 standard. After 14 days the peripheral lymph nodes are removed for the proliferation test.

The gp120 protein of HIV-1-LAI is used to induce the proliferation of the lymph node cells which have been in contact with the fusion protein ORF2-region V3 produced by the recombinant BCG.

Figure 19:
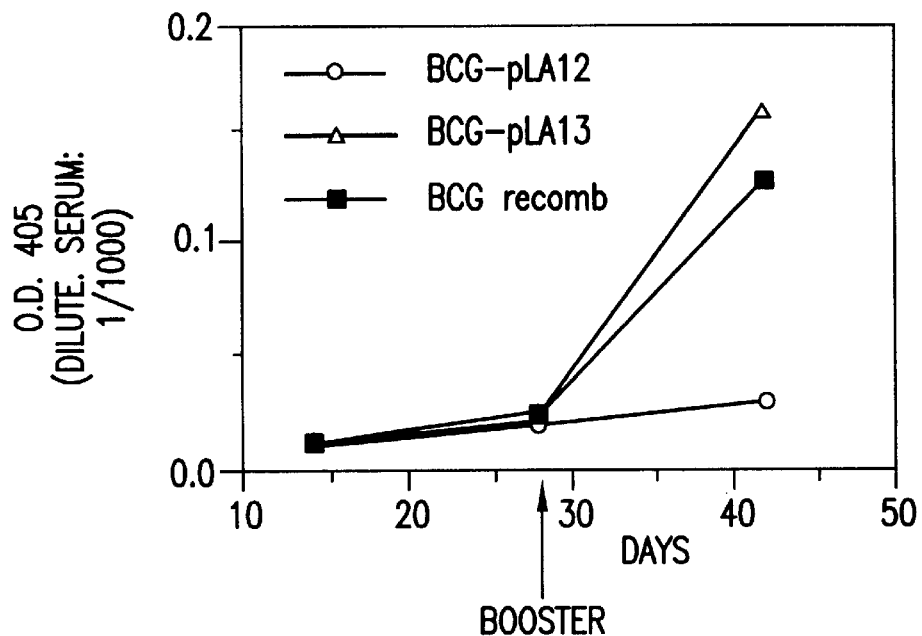

FIG. 19: Level of anti-peptide V3 antibodies measured by ELISA assays.

5 mice receive an intravenous injection of a vaccinal preparation which contains $5\times10^6$ CFU of BCG transformed with pLA12; 5 others receive the same quantity of recombinant BCG pLA13; 5 mice receive a similar quantity of recombinant BCGs which express the lacZ gene but not the ORF2-env' gene, "naive" mice were not given an injection. Blood samples were taken after 14 days, then every 2 weeks in order to measure the change in the level of specific antibodies to the fusion protein ORF2-env'.

For the ELISA assay we used as antigen capable of being recognized by the antibodies present in the sera a peptide of 20 amino acids of the V3 loop of gp120MN (aa306 to aa325), recognized by the antibody SC-D (K24-1).

FIG. 20: Plasmid pTG2103. This is a derivative of pTG959 (Guy et al., 1987) in which a BglII/EcoRI fragment bearing the gene which codes for the protein P24 of HIV-1/LAI has been cloned into the polylinker.

FIG. 21: Construction of the plasmids pLA22 and pLA23 bearing the fusion pAN-ORF2-gag (HIV-1/LAI).

FIG. 22: Expression of the polypeptide ORF2-gag (HIV-1/LAI) by BCG.

DETAILED DESCRIPTION

A part of the useful sequence I in the framework of the invention may be defined by performing a test such as the following: a specific part of sequence I is doned upstream of a vector bearing sites for promoter recognition and translation signals, containing for example the beta-galactosidase gene lacking its promoter and its first eight amino acids.

The conditions used for carrying out the test can be established on the basis of the description relating to the constructions shown in FIGS. 7 to 9 (SEQ ID NOS:3–5). A part thus tested of sequence I, which is useful in the framework of the invention, leads to the synthesis of a protein having a beta-galactosidase activity in different cell hosts, for example the actinomycetes.

A first particularly useful nucleotide sequence according to the invention which can be used for the cloning and/or expression of a nucleic acid is sequence (II), characterized in that it comprises:

a) the following nucleotide sequence or any part of this sequence which contains in particular the transcription initiation site (position +1) and elements necessary for the recognition and binding of the RNA polymerases of a specific cell host which will be transformed by this sequence, these elements comprising in particular the (TAC ACT) sequences at position −10 relative to the transcription initiation site and (TC GAC A) at position −35 relative to this site (SEQ ID NO:6)

```
GAT CCC GTG ACA AGG CCG AAG AGC CCG CGA CCG TGC

GGT CGT CGA CGA CCG AGT GTG AGC AGA CCC CCT GGT

GAA GGG TGA ATC

+1
GAC AGG TAC ACA CAG CCG CCA TAC ACT TCG CTT CAT
```

-continued

```
GCC CTT ACG GGG GGC GGC CAA CCC AGA AGG AGA TTC

TCA
``` b) a sequence which hybridizes with the sequence complementary to sequence a) under conditions given below.

The conditions of hybridization referred to above can be described as follows:

For example, a specific probe, labelled with $^{32}P$ ($10^6$ cpm/ml) and taken from the sequence with which it is desired to test the hybridization, is used and placed in contact with the test sequence for 16 hours at 65% C. in a hybridization solution (50% formamide, 5×SSPE, 200 μg/ml of salmon sperm DNA and 10×Denhardt). The membranes on which the hybridization is carried out are then washed twice for 30 minutes with a 1 SSC solution, 0.1 SDS at room temperature (20° C.), then washed twice with 0.1 SSC, 0.1% SDS for 30 minutes at 65° C.

Composition of 5×SSPE:
NaCl: 900 mM
$NaH_2PO_4$: 450 mM
$Na_2EDTA$: 5 mM
pH: 7.4
Denhardt:
Ficoll: 2.5 g/l
Polyvinylpyrrolidone: 2.5 g/l
BSA (Pentex fraction V): 2.5 g/l
0.1×SSC:
NaCl: 15 mM
$Na_3$ citrate: 0.1%

The nucleotide A marked +1 corresponds to a specific transcription initiation site in the framework of the invention and the nucleotide sequence upstream from this site contains elements for the recognition and binding of the RNA polymerases (regions −35 and −10) of cell hosts in which the sequence is capable of being used as promoter for the cloning and expression of specific nucleic acid sequences. The regions −35 and −10 are localized relative to the +1 site.

The above sequences (sequences I and II) contain the minimal sequence necessary for the initiation of transcription defined above as well as fragments upstream and downstreamfrom this sequence capable of playing a role in the regulation of transcription and/or expression. For example, these sequences contain a sequence of the Shine-Dalgarno type (A AGG AG), implicated in ribosome binding.

Another nucleotide sequence capable of allowing the expression of a nucleotide sequence in a cell host is characterized according to the invention in that it contains DNA sequence (III) selected from:

a) the following nucleotide sequence (SEQ ID NO:7):

| |
|---|
| TC GAC AGG TAC ACA CAG CCG CCA TAC ACT TCG CTT CA | b) a sequence which hybridize with the sequence complementary to sequence a) under conditions given below, c) any part of this sequence implicated in the transcriptional activity of a nucleic add.

The sequence designated in b) defined by its capacity to hybridize with I, II or III gives in each case the variants of the sequence of the invention which, while being modified at one or more nucleotides, conserve the properties of sequences I, II or III of the invention in the transcription of a nucleic acid. The modifications capable of being introduced in the variants are, for example, substitutions, insertions, deletions or inversions of nucleotides.

The nucleotide sequence comprising one of the sequences I, II, or III or a variant of I, II or III contains a nucleotide sequence which can function as a promoter for the expression of given nucleic acid sequences.

The nucleotide sequences of the invention can also be designated in what follows by the expression "sequence containing the promoter" when they contain the sequence III.

Optionally, sequence III can be used with a fragment of sequence I which is not necessarily adjacent to it in sequence I but which is implicated together with I in the expression of a given nucleic acid.

The above-mentioned sequences can be obtained by extraction, purification from the DNA of *M. paratuberculosis* or by chemical synthesis.

According to another embodiment of the invention, any variant of a nucleotide sequence comprising the sequences I, II or III described above can be defined by the fact that it conserves the functional properties of the sequences I, II or III and in particular their capacity to fulfil promoter functions for the transcription of nucleotide sequences within a given host.

The elements of nucleotide sequence I or sequence II which flank sequence III may be deleted at least in part and optionally substituted For example, the sequence included between the nucleotide positions +2 and +41 with respect to the transcription initiation site can be replaced wholly or in part by a sequence exogenous with respect to the sequence naturally present downstream of sequence II in Mptb, this exogenous sequence comprising Shine-Delgarno sequence capable of being recognized by the ribosome in a specific host.

As an example this sequence included between the positions +2 and +41 may be replaced by an exogenous sequence of bacterial origin, for example *E. coli*, which includes a Shine-Dalgarno sequence.

The invention also relates to the use of any part of sequence I or II outside the −35 and −10 regions or the Shine-Dalgarno (SD) sequence, likely to be implicated in the transcription or translation of a given nucleic acid.

The invention also relates to a recombinant nucleotide sequence characterized in that it comprises a nucleotide sequence such as that defined above and at least one nucleic acid sequence whose cloning and/or expression is desired in a specific cell host under the control of this promoter.

This sequence may be a sequence coding for a Mptb peptide, or a heterdogous sequence which codes for a peptide or a polypeptide of different origin.

A nucleic acid sequence is considered to be a heterologous sequence if it does not correspond to the sequence naturally adjacent to the sequences I or II in Mptb, a part of this sequence naturally adjacent corresponding to the sequence of 716 bp shown in FIG. 2.

The agents of the invention can thus be used for the expression of a nucleic acid sequence which codes for a peptide or a polypeptide of Mptb under the control of the nucleotide sequence of the invention in a cell host different from Mptb.

The recombinant sequence may be used both to clone a coding sequence in a specific host, for example a bacterium such as *E. coli.* and then to transfer this sequence in order for it to be expressed in a different host for example an Actinamycete and in particular in a mycobacterial strain, in particular a BCG strain.

The invention can be used to done or express any type of nucleic acid sequences and in particular sequences coding for peptides, polypeptides or proteins (the expression polypeptide may replace all of these terms) which have an antigenic character.

The object of the invention is, for example, a particular recombinant sequence complying with the preceding specification, characterized in that at least one nucleic acid sequence placed under the control of a nucleotide sequence of the invention I, II or III defined above codes for an immunogenic peptide or polypeptide or one capable of being made immunogenic.

As an example a nucleic acid sequence to be expressed incorporated into a recombinant sequence of the invention can be a sequence characteristic of a pathogenic organism. Pathogenic agents are for example viruses, parasites, bacteria. Mention is made of *M. leprae, M. tuberculosis, M. intracellulare, M. africanum, M. avium*, the sporozoites and merozoites of plasmodium, the bacilli responsible for diphtheria, tetanus, Leishmania, Salmonella, certain treponemae, the toxin of pertussis and other pathogenic micro-organisms and viruses, in particular the virus of mumps, German measles, herpes, influenza, Schistosoma, shigella, Neisseria, Borrelia, rabies, polio, hepatitis, AIDS HIV, HTLV-I HTLV-II and SIV as well as on cogenic viruses.

The nucleic acid sequence to be expressed may also code for an immunogenic sequence, for example a snake or insect venom The recombinant nucleotide sequence may also contain several antigen-coding sequences, optionally characteristic of different organisms, under the control of the same nucleotide sequence of the invention.

The invention preferably relates to a recombinant sequence characterized in that the nucleic acid sequence to be expressed codes for a peptide or polypeptide of a HIV retrovirus, for example an envelope peptide or polypeptide, or a peptide or polypeptide of the Nef protein of HIV-1 and HIV-2.

Other nucleic acid sequences may be used in the framework of the embodiment of the invention and mention should be made as examples of the antigens or immunogenic sequences of mycobacteria, in particular the proteins or protein fragments corresponding to genes implicated in virulence and antigens with protective potential. An antigen is said to be "with protective potential" if it is capable of triggering or promoting a protective immune response in particular by the production of antibodies or by the induction of an immune response of the cellular type, in particular of the CTL type.

It is possible to consider creating a recombinant sequence in which the nucleotide sequence of the invention is implicated in the control of the expression of one or more specific haptens or epitopes, optionally belonging to different organisms. Furthermore, these haptens or epitopes may be combined with a sequence coding for an antigen or more generally a polypeptide which can be used as carrier protein in particular for the expression, at the surface of the cell host and even for the secretion, of the hapten(s) or epitope(s).

By combination is meant either the formation of a hybrid coding sequence between the different sequences present in the recombinant sequences or a combination in the form of coding elements of an operon, the different coding sequences retaining in this case their individuality during their expression in a cell host or the formation of a fusion protein resulting from the expression of a fusion gene.

Nucleotide sequence I, II or III of the invention may be placed either upstream of the nucleotide sequence to be expressed and in phase with this sequence, or downstream fron the nucleic add sequence to be expressed The choice of position relative to the coding sequence may be determined as a function of the desired level of expression in a specific host.

In the recombinant nucleotide sequence of the invention a nucleotide sequence according to the invention and the nucleic acid sequence(s) to be expressed may thus constitute a fusion operon. In this case if several nucleic acids are present, they are expressed under the control of the sequence but in the form of individual products.

According to another embodiment of the invention nucleotide sequence I, II or III and the nucleic acid sequence(s) to be expressed constitute a fusion gene. In this case the expression product of this gene is constituted by a hybrid protein or fusion protein when several nucleic acids are used.

Generally, the invention relates to the use of a nucleotide sequence according to the preceding description for the cloning and/or expression of nucleic acid sequences in a cell host different from Mptb, in particular in Actinomycetes and in particular Mycobacteria and in particular in *M. bovis* for example in the avirulent strain BCG, in Cram-negative bacteria such as *E. coli* or in Gram-positive bacteria such as *B. subtilis*.

Also included in the framework of the invention is a cloning and/or expression vector of the integrative or replicative type, characterized in that it comprises at a site inessential for its integration or its replication, respectively, a nucleotide sequence comprising the sequences I, II or III or their variants according to the preceding specifications.

These vectors are thus either capable of replicating extrachromosomally or, on the contrary, in the form of elements integrated within a chromosome or more generally within an element of the genome of a host into which they have been incorporated, including a plasmid or a bacteriophage present in this host.

A vector according to the invention can also be characterized in that it is modified at a site inessential for its integration or its replication, respectively, by a recombinant nucleotide sequence described above.

A particular vector comprises in addition to the promoter and a heterologous sequence at least a part of the sequence designated by ORF2 of Mptb (FIG. 10) (SEQ ID NO: 8). This sequence is advantageously placed downstream from the sequence containing the promoter, preferably between the promoter and the heterologous nucleic acid sequence. Advantageously, this part of ORF2 corresponds to a sequence of 716 bp of Mptb as described in FIG. 2.

As examples of satisfactory vectors for carrying out the invention, mention may be made of plasmids, transposons, phages and any other vector which can be used for the expression of a sequence. In particular, a useful plasmid, optionally as intermediate plasmid for carrying out the invention, is an *E. coli* strain (Myc758) containing the 716 bp (PstI/BamHI) fragment cloned in the vector pUC18, deposited with the Collection Nationale des Microorganismes at Paris, France under the number I-1157 on Oct. 23, 1991.

This plasmid includes in particular the promoter of the invention corresponding to sequence II, defined by the restriction sites EcoRI/BglII (pan promoter) as well as a linker.

As examples of vectors mention should be made of the plasmids derived from pAL5000 (Ranzier et al., 1988, Gene 71: 315–321), RSF1010 (Hermans et al., 1991, Mol. Microbiol. 5: 1561–1566), pNG2 (Radford et al., 1991, Plasmid 25: 149–153), the transposons derived from Tn610 and IS6100 (Martin et al., 1990, Nature 345: 739–743), IS900 (Green et al., Mol. Microbiol.), IS901 (Kunze et al., 1991, Mol. Microbiol. 5: 2265–2272), IS6110 (Thierry et al., Nucl. Acids Res., 1990, 18: p188) and the phages L5 (Lee et al., 1991, Proc. Natl. Acad. Sci., 88: 3111–3115), D29 (Tokunga et al., 1964, J. Exptl. Med., 119: 139–149).

Other nucleotide sequence elements may be incorporated or be present in the vector of the invention; they may be for example expression markers and in this connection reference may be made to the genes for antibiotic resistance such as kanamycin or viomycin. Other regulatory elements may be sequences implicated in the expression of the coding sequence and in particular sequences of the operator type or also of elements capable of promoting the exportation, exposure at the membrane of the host, the excretion or secretion of the expression product of the heterologous sequence.

The invention also relates to a recombinant cell host characterized in that it is transformed by a recombinant nucleotide sequence described above or by a vector described above under conditions permitting the expression of the nucleic acid sequence(s) to be expressed which are contained in the recombinant sequence or in the vector.

A particularly advantageous cell host for carrying out the invention is a host which leads to the exposure at its surface, or even the excretion or secretion, of the expression product of the nucleic acid sequence(s) to be expressed which it contains or to its synthesis under conditions of intracytoplasmic localization.

Particular hosts are for example Actinomycetes strains, preferably avirulent strains like for example the avirulent BCG strain of the PASTEUR INSTITUTE NO 1173P2 used to constitute the vaccine sold under the name "Vaccin BCG Pasteur Merieux".

The inventors have however observed that the sequence containing the specific promoter of Mptb is capable of functioning in strains other than the Actinomycetes and can function for example in a Gram-negative bacterium such as *E. coli*. This sequence is also capable of being used in Gram-positive bacteria such as *B. subtilis* or in Streptomyces.

A procedure adapted for the preparation of recombinant cell hosts according to the invention is for example electroporation, in conformity with the description of Snapper et al. (1988, PNAS USA 85: 6985–6991) or conjugation according to the technique of Lazraq R et al. (1990, FEMS Microbiol. Lett. 69: 135–138).

In the light of the attractive properties of this promoter and of the possibility of expressing antigens and immunogenic sequences in selected strains and particularly in avirulent strains, the invention offers an immunogenic composition characterized in that it contains a recombinant cell host complying with the foregoing criteria, in sufficient quantity to trigger the production of antibodies, or to contribute to the production of preferably protective antibodies in a human or animal host to which it is administered.

This immunogenic composition may be used for triggering a protective response against a specific pathogenic agent by the production of antibodies and the induction of an immune response of the cellular type, provided that the expression product of the nucleic add sequence expressed under the control of sequences I, II or III is under conditions which trigger this production. The immunogenic composition may also be used as a booster composition to stimulate the production of antibodies initiated by a protein or another constituent.

The response generated subsequent to the administration of the immunogenic composition may be of the cellular type; in particular, it may be a CTL-type sequence.

The invention thus also makes it possible to prepare vaccines of the mixed vaccine type in which the antibody production is directed against both the cell host and in particular the BCG bacillus and against the expression product of the nucleic acid sequence to be expressed.

In addition to its attractive properties for the production of a vaccine, a composition comprising a recombinant cell host according to the invention can be used to carry out immunotherapy.

Such a vaccine or composition for immunotherapy can be used in animals or man and be administered by the intradermal, subcutaneous, oral or percutaneous route or by aerosols. Several administrations may be necessary for example inthe form of a booster to obtain sufficient protection.

A recombinant cell host according to the invention may also be used to produce any protein or peptide, particularly on an industrial scale. It is thus possible to use the invention for the production of antibiotics.

Other characteristics and advantages of the invention will become apparent in the Examples and the Figures which follow.

MATERIALS AND METHODS

Bacterial Strains, Phages, Plasmids and Culture Media

*M. bovis* BCG (BCG) strain Pasteur 1173 P2 called BCG (Calmette A. L' infection balladries et la tuberculous chez l' homme et chez les animaux. Processus d' infection et de défense. Etude biologique et expérimentale. Vaccination préventive. Ed Masson, Paris, 1928) was used as host for the construction of the different BCG recombinants (r-BCG). Other bacteria, phages and plasmids used in the experiments reported hereafter are described in Table I. The BCG was grown on Sauton medium (Sauton B., Comptes Rendus Académie des Sciences 1912: 155–1860 in Calmette et al., Vaccination préventive par le BCG p.811—Ed. Masson 1928) until a surface pellicle formed in order to produce a standard vaccinating preparation or one in the form of a dispersed culture. The bacterial clones of r-BCG were first grown on a Lowenstein-Jensen medium (Jensen K., Towards a standard of laboratory methods, 4th Rep. Subcomm laboratory methods. Bull Union Internat. against Tuberc., 1957, 27: 146–166) containing 10 μg/ml of kanamycin, then transferred to Sauton medium These cultures were used for analyses of expression in vitro and for the immunization of the animals. The *M. smegmatis* and *E. coli* strains were grown according to the method described by Ranes et al. (1990), J. Bact. 172: 2793–2797.

Preparation of the DNA of *M. paratuberculosis*

50 mg of lyophilized *M. paratuberculosis* strains (Murray A et al., NZ Vet. Journal previously cited) were resuspended in a homogenization buffer (0.1 M NaCl, 0.03M Tris-HCl, pH 7.5, 0.006M EDTA) mixed with 2 nl of glass beads (0.45–0.5 mm diameter) and homogenized in a Braun rotatory homogenizer at maximal speed for 2 minutes at 4° C. After centrifugation and extraction with phenol/chloroform, the DNA was precipitated with 95% ethanol and treated with 0.1 mg/ml of RNASe-free DNAse. After another extraction with phenol/chloroform and precipitation with ethanol, the DNA was resuspended in water (A260/280 ratio=1.8).

Construction of the Gene Library of *M. paratuberculosis*

The method used was based on the protocols described by Young et al. (Proc. Natl. Acad. Sci. (1985) 82: 2583–2587) modified by Murray et al. (NZ Vet. J. (1989) 37:47–50). The library contained $2.2\times10^5$ recombinant bacteriophages. After amplification in *E. coli* Y1090, the recanbinants represented approximately 85% and corresponded to a titer of $3\times10^{11}$ PFU/ml.

Screening of the Lambda gt11 Library of *M. paratuberculosis*

The library was screened by differential hybridization of the DNA obtained by transfer from Petri dishes containing the phage lysate to membranes (Young et al. previously cited) by using the whole chromosomal DNA of *M. paratuberculosis* (Mptb) and *M. phlei* as probes. The recombinant bacteriophage which gave a positive signal after hybridization with the DNA of Mptb but did not hybridize with *M. phlei* was kept for subsequent analyses. It was propagated by using the method of plate lysate as described by Maniatis et al. (J. Molecular Cloning: A laboratory manual. Cold Spring Harbor Laboratory. Cold Spring Harbor. N.Y. (1982)).

Manipulation of DNA

The DNA fragments were separated on 0.8% or 1% agarose gels containing 0.5% ethidium bromide. The DNA was eluted from the gels and purified by using the Geneclean II kit (Bio101 Inc La Jolla) according to the manufacturer's directions.

The cloning of fragments in plasmids and the transformation of *E. coli* were performed by using the standard procedures described by Maniatis et al. (publication previously cited). The transformation of mycobacteria was performed according to the description of Ranes et al. previously mentioned.

Determination of the Nucleotide Sequence

The DNA was cut randomly by sonication and the fragments were cloned randomly in M13. The clones were sequenced by the dideoxy chain termination method by using the Sequenase kit (USB) and 7-deaza-dGTP, an analogue of dGTP. Overlappings and the analysis of the sequence data from the fragments randomly obtained were carried out by using the computer programs described by Staden et al. (Nucleic Acids Res. (1986) 14: 217–231)

Preparation of RNA

A 100 ml culture of *M. smegmatis* MYC760 strains was grown to mid-log phase in a Middlebrook 7H9 medium, supplemented with an ADC (Difco) enrichment plus 25 μg/ml of kanamycin at 37° C. The cells were collected after centrifugation, washed with the same fresh growth medium and resuspended in a medium containing 1% (wt/v) sodium triisopropylnaphthalene sulphonate and 6% wt/v) of sodium 4-aminosalicylate 14 g of glass beads (4.5–5.5 mm) were added, the mixture was homogenized vigorously in a Vortex mixer for two periods of 2 minutes. The supernatant was extracted twice with phenol/chloroform and the nucleic acids in the aqueous phase were precipitated with propan-2-ol in the presence of 0.3 M sodium acetate at pH 6. After centrifugation for 10 minutes at 8000 rpm, the centrifugation pellet was washed with 100% ethanol, dried at room temperature for 10 minutes and resuspended in 1 ml of distilled water treated with DEPC. The RNA was precipitated with three volumes of 4M sodium acetate (pH 6) at −20° C. for 18 hours, collected by centrifugation and resuspended in distilled water (optical density OD 260/280=2.0). The RNA was stored at −20° C. in the form of a precipitate in propan-2-ol.

Mapping of the Transcripts

The plasmid pAM311 was linearised with BssHII to produce 5' extensions and dephosphorylated with calf intestine alkaline phosphatase. After purification of the plasmid with the Geneclean kit, the DNA was cut with the restriction enzyme PstI and the 3.1 kb fragment was isolated from a 1% agarose gel. The 5' hydroxyl end was radiolabelled with ATP (gamma $^{32}$P) (specific activity 3000 Ci/nmol) by using polynucleotide kinase (10 units). Unincorporated label was removed by passage through a Nick column (Pharmacia).

The RNA (40 µg) and the radidabelled DNA probe (0.1 µg) were mixed in a total volume of 30 82 l of distilled water, 240 µl of deionized formamide were added and the mixture was heated at 100° C. for 3 minutes. After rapid cooling in ice, 30 µl of 10X hybridization buffer (0.2M PIPES-NaOH, pH 6.4, 4M NaCl, 20 mM EDTA) were added and the incubation was continued at 60° C. for 3 hours. The DNA/RNA hybrids were precipitated with three volumes of ethanol at −20° C. for 16 hours. After centrifugation for 15 minutes at 4°C., the nucleic acid pellet was resuspended in 100 µl of buffer containing 50 mM sodium acetate at pH 4.6, 280 mM NaCl, 5 mM $ZnCl_2$ and 20 ug per ml of denatured salmon sperm DNA 2 µl of S1 nuclease (472 units) were then added and the digestion was continued for 30 minutes at 20° C. The reaction was stopped by addition of 25 µl of a solution containing 2.5 M $CH_3COONH_4$ and 50 mM EDTA at pH 8. The DNA/RNA hybrids were precipitated with propan-2-ol in the presence of 1 µg of carrier DNA (denatured salmon sperm DNA). After washing in 80% ethanol, the pellet was resuspended in 5 µl of distilled water and 7 µl of stop solution (95% v/v formamide, 20 mM EDTA, 0.05% bromophenol blue, 0.05% xylene cyanol FF). The mixture was heated at 100° C. for 5 minutes and then loaded on to a 6% polyacrylamide sequencing gel.

Serological Assays

Murine sera were assayed by ELISA to detect specific antibodies directed against beta-galactosidase according to the following procedure: microtiter plates with 96 wells (Nunc) were coated with 10 µg/ml of purified beta-galactosidase in PBS buffer for 1 hour at 37° C. and for 16 hours at 4° C. After three washings with PBS containing 0.1% Tween 20, the sera which had been preabsorbed with the BCG extracts for 16 hours at 4° C. were added to the wells in a dilution buffer (PBS+0.1% Tween 20, 1% BSA) for 2 hours at 37° C. After three washes, the antibody titers were determined by photometry at 405 nm using a rabbit anti-mouse IgG conjugated to alkaline phosphatase (Biosys, Compiegne) and 1 mg/ml of p-nitrophenyl phosphate as substrate.

Beta-galactosidase Assay

The beta-galactosidase activity was measured in *E. coli* cells treated with toluene and in *M. smegmatis* extracts subjected to a sonication treatment as described by Cossart et al. (J.Bacteriol. (1985) 161: 454–457).

Immunization of the Animals

6 Weeks old female Balb/c mice were obtained from Iffa Credo. In order to monitor the cellular immune responses the mice were inoculated subcutaneously (sc) at the base of the tail with $10^7$ colony-forming units (CFU) of BCG strains. The lymph node cells were removed 14 days after immunization and the proliferative responses were studied. A control group of mice received Freund's incomplete adjuvant (FIA) in saline solution. In order to monitor the production of antibodies, a group of mice was inoculated intravenously (iv) with $5 \times 10^6$ CFU of the BCG strains. Some of the mice were given an intravenous booster three times at intervals of 21 days with $10^6$ CFU; the serum samples were taken 28 days after immunization and 14 days after each booster in order to titer the antibodies.

The stability of the different BCG strains was analysed by determination of the number of BCG CFU recovered from the spleen two months after the inoculation (iv) with $10^7$ BCG CFU.

Proliferative Responses to Specific Antigens 14 days after immunization cell suspensions were prepared from inguinal lymph nodes (LN) taken from three mice and resuspended in RPMI1690 (Gibco) containing 2 mM L-glutamine, 50 µg/ml gentamycin, $5 \times 10^5$ M 2-mercaptoethanol and 10% fetal calf serum (FCS). The LN cells were grown at a concentration of $4 \times 10^5$ cells per well in flat-bottomed culture plates containing 96 wells (Corning) in the presence of a suitable antigen. The antigen concentrations used were the following: 0.01 µg/ml of APH3' and beta-galactosidase and 10 µg/ml of a purified protein derivative (PPD). Concanavalin A (ConA) was added at a concentration of 2.5 µg/ml as non-specific positive reaction control. Some cell suspensions remained unstimulated. Each assay was carried out in triplicate The cultures were incubated for five days at 37° C., the last 22 hours in the presence of tritiated methyl thymidine (3H dThd 1 mCi=37 KB2 Amersham) 0.4 µCi/well in an atmosphere of moist air containing 7% $CO_2$. The cells were then harvested on glass fiber filters (Automash 2000 Dynatch) and the radioactivity incorporated was measured. The results are expressed as a function of counts per minute (cpm) minus background. The standard errors of the mean for the cultures in triplicate were determined. The background values of the unstimulated control cultures were less than $10^4$ cpm.

Anti-CD4 and Anti-CD8 Monoclonal Antibodies

In order to determine the ratio of the T cell subgroups implicated in proliferation monoclonal antibodies against the T cell subgroups were added to the LN cell culture at different concentrations. The L3T4 (CD4+) hybridoma GK 1-5 of rat anti-mouse specific CD4+ and LYT2 (CDB8+) (hybridoma H35 17-2 of rat anti-mouse specific CD8+) were produced according to the method described by Dialynas D. P. et al., 1984, J. of Inmunology vol. 31, p. 2445–2451). In brief, in order to obtain monoclonal antibodies from ascites, nude mice were inoculated a first time with cells corresponding to 106 hybridomas, The antibodies were collected by precipitation with ammonium sulfate The quantity of proteins was measured by means of the optical density at 280 nM.

Measurement of the Cytokines

The synthesis of gamma-interferon was measured in the culture supernatants of LN cells at the end of the proliferation assay. The level of gamma-interferon was determined by a solid phase immunoenzymatic assay by using the multiple sandwich principle (Genzyme). The supernatant was diluted (½–¹⁄₁₀). The gamma-interferon standard was diluted to obtain values within the linear range of the assay (128–8200 pg/ml).

RESULTS

Isolation and Characterization of the Recombinant Bacteriophages

A lambda gt11 genome library was constructed in order to isolate specific sequences of *M. paratuberculosis* (Mptb).

Recombinant phages which hybridized strongly with the chromosomal DNA of Mptb but not with the DNA of *M. phlei* were taken up again individually and used to prepare the phage lysate stocks (Maniatis et al., previously cited). One of these recombinants was selected at random for additional assays. Its genome contains a 3.8 kb insertion. The DNA of mycobacteria was recovered from this fragment by digestion using the restriction enzymes EcoRI and BamHI This led to the production of four fragments which were separated on an agarose gel. One of these fragments, 1.6 kb, was eluted from the gel and ligated to the plasmid pGEM-2 digested by EcoRI/BamHI Competent *E. coli* DH5 alpha cells (Bethesda Research Laboratories, Gaithersburg Md. USA) were transformed with the ligation mixture according to the manufacturer's directions then applied to plates with an LB medium containing 100 μg/ml of ampicillin. A single colony was selected and used to prepare a sufficient quantity of the recombinant plasmid which was designated pAM3 by using the standard procedure described by Maniatis et al. previously mentioned When pAM3 was labelled with the chemical probe kit (Promega) and used as probe in a dot-blot assay, hybridization occurs only with the DNA extracted from *M. paratuberculosis*. The different isolates of Mptb assayed included the type strain *M. paratuberculosis*, isolates of 23 Mptb originating from beef cattle, sheep and goats and an isolate from a human patient with Crohn's disease. The pAM3 plasmid did not hybridize with *M. avium* serovar 2 and 3, *M. intracellulare, M. tuberculosis* strain H37Rv, *M. bovis, M. phlei, M. smegmatis* or *N. asteroides.*

Sequence Analysis

The nucleotide sequence of the 716 bp BamHI/PstI fragment is reported in FIG. 2. Sequence analysis for consensus signals at the start of transcription and translation led to the demonstration of a potential region at −35 (positions 83–88), a region at −10 (positions 106–111) and a Shine-Dalgarno (SD) sequence at the positions 147–152. A long open reading frame (ORF) designated as ORF2 follows the SD sequence with an ATG initiation codon at position 160. The nucleotide sequence analysis of the fragment showed a homology with the insertion element IS900 *M. paratuberculosis*. The 153-716 segment was identical with the nucleotide sequence 1451 to 888 of IS900 (Green et al. (1989) Nud. Acids Res. 17: 9063–9073). ORF2 is oriented in the opposite direction to the transcription of the potential transposase of this element ORF1197. The segment 1-152 is outside the IS900 sequence.

ORF2 does not exhibit similarity with other sequences if reference is made to the sequences contained in the data bases. When IS900 is used as genomic probe for the Southern blot tests of different isolates of Mptb. patterns of almost identical multiple bands are obtained, irrespective of the origin of the isolates (McFadden et al. (1987) J. Clin. Microbiol. 25: 796–801). This absence of polymorphism suggests that IS900 is integrated predominantly at specific sites within the Mptb genome. A limited number of sequences adjacent to the end of IS900 has been reported, it seems to contain conserved nucletide sequences (Green et al. (1989) Nucl. Acids Res. 17: 9063–9073). The Shine-Dalgarno (SD) sequence AAGGAG shown in FIG. 2 is adjacent to the element IS. The reverse complementary sequence to this SD sequence (CTCCTT) is identical with the flanking sequence reported for IS900 contained in the clone pMB22 derived from the genome library of the human isolate of mptb derived from a patient suffering from Crohn's disease.

Analysis and Expression of ORF2

In order to study the expression of ORF2 at the transcriptional and translational level, the 716 bp BamHI/PstI fragment of pAM3 was cloned between the BamHI and PstI sites of the fragment containing several cloning sites (MCS) of the plasmid pNM482 (Minton et al. (1984) Gene 31: 269–273). The MCS is adjacent to a truncated beta-galactosidase gene (lacZ) lacking its first eight N-terminal amino acids and its start signals for transcription and translation. The introduction of a correctly aligned segment containing appropriate regulatory signals and coding sequence downstream leads to the formation of a hybrid gene which confers the $LacZ^+$ phenotype ORF2 was in phase with the lacZ gene whose construction is described above and the translation product should be expressed in the form of a fusion protein ORF2-beta-galactosidase containing 185 amino acids of ORF2. However, the transformation of *E. coli* MC1061 did not produce colonies transformed by $Lac^+$. The expression of the fusion gene ORF2-lacZ ina mycobacterial system has been studied. Consequently, the 3.8 kb SmaI/DraI fragment containing the fusion gene was ligated in the form of a fragment with blunt ends to the ScaI site of the plasmid pRR3, a shuttle vector between the mycobacteria and *E. coli* to produce pAM320. The transformation of *M. smegmatis* with this plasmid by electroporation followed by culture in the presence of kanamycin and X-gal led to the production of blue colonies appearing in three days. A similar experiment to transform the BCG with this plasmid also made it possible to obtain blue colonies which appeared after approximately 21 days. Thus, it was possible to express orf2 in the form of a fusion protein with beta-galactosidase.

In order to quantify the expression of orf2, the level of activity of beta-galactosidase was measured in *M. smegmatis* and in *E. coli* both transformed with pAM320 or with pRR3. The results are given in Table III 250 Units were found in *M. smegmatis* transformed with pAM320 harbouring the fusion gene orf2-lacZ but no activity was found in the *M. smegmatis* strain transformed with pRR3. In the *E. coli* strains transformed with pAM320 only a low level of activity was found (5/7 units). These results show that the fusion orf2-lacZ is not expressed in *E. coli* and suggests that orf2 must be expressed specifically in mycobacteria.

Transcription Analysis

The transcription initiation site of the fusion gene orf2-lacZ within pAM320 was determined by high resolution mapping with the S1 nuclease. The experiments demonstrated that the transcription initiation site of the sequence is situated upstream from orf2 at position 119 (FIG. 4). A second initiation site is present outside the mycobacterial sequence. Two explanations can be found for this observation. First, this may be due to hybridization of the probe with a small quantity of shuttle plasmid which has been coprecipitated during the preparation of the RNA, otherwise this may be due to the reading of the results of transcription through the intermediary of the gene for resistance to ampicillin in pRR3. These results as well as the expression of the fusion protein with beta-galactosidase indicate that the promoter element pan which is adjacent to the element IS900 is capable of controlling the expression of orf2. That is the first demonstration of the induction of the expression of a gene localized within an insertion sequence, by means of an adjacent chromosomal promoter.

Construction of the Fusion Operon orf2-lacZ

In order to characterize more precisely the activity of the promoter pan, orf2 was deleted and a fusion operon with the lacZ gene was constructed (FIGS. 7, 8 and 9).

pWR32 and pWR33 are recombinants of pRR3 containing the fusion pan-LacZ in both orientations (FIG. 9). The transformation of either *E. coli* or *M. smegmatis* with these constructions followed by growth in the presence of kanamycin and X-gal led to the production of blues colonies in the case of both species of bacteria Thus pan is functional in *E. coli* when it is present in the fusion operon with LacZ but it is not functional when it is present in a fusion gene with orf2.

pWR32 induced the same level of beta-galactosidase activity in *M. smegmatis* as pAM320. However, the level of activity with pWR33 was 10 times higher in *E. coli*. This must be due to the constitutive activity of a promoter upstream from the fusion gene pAM-lacZ.

Specific Cellular Immune Response

Balb/c mice were inoculated subcutaneously with BCG recombinants harbouring the plasmid pAM320 which expresses the phosphotransferase APH3' under the control of its own regulatory region and lacZ under the control of pan. The proliferative responses of the LN cells collected 14 days after immunization were analysed. A specific response to in vitro stimulation with different antigens was observed (FIG. 4). Only the mouse LN cells immunized with r-BCG expressing lacZ and APH3' proliferated in response to in vitro stimulation by beta-galactosidase and by the aminoglycoside phosphotransferase (APH3'). The cell proliferation in response to a PPD (Protein Purified Derivative) extract was similar with the mouse LN cells immunized with the non-recombinant BCG strain. The LN cells of the unimmunized animals proliferated only in response to ConA. This unspecific proliferation was of the same order of amplitude in all groups of animals.

It has been demonstrated that the CD4+ and CDB+ T cells are implicated in the proliferative responses described above by alternative inhibition of proliferation with anti-CD4+ and anti-CD8+ monoclonal antibodies. These results are presented in FIG. 5. 70% Inhibition of the specific response to beta-galactosidase is observed after addition of anti-CD4+ antibodies to the LN cell cultures. In similar experiments 30% inhibition was observed after addition of anti-CD8+ antibodies to the cultures. These results show that the greatest response is obtained with the CD4+ subgroup of the T cells. Two different populations of CD4+ T cells participate in the regulation of the immune response in mice. One subgroup of CD4+T cells designated as TH1 produce interleukin-2 (IL2) and gamma-interferon and preferentially activate the macrophages to kill or inhibit the intracellular growth of the pathogenic agent. The other subgroup of CD4+ T cells which is designated as TH2 produces other lymphokines including IL4, IL5 and is implicated in the induction of humoral responses. A significant production of gamma-interferon was detected in the supernatants of LN cell cultures with specific antigens (FIG. 6). These values were slightly lower than those obtained after stimulation with PPD or ConA However, they remain significant because the minimal value of the standard curves was 100 pg/ml. The production of gamma-interferon by these LN cells isolated from animals immunized with non-recombinant BCG was only observed after stimulation in vitro with PPD or ConA.

Antibody Response

Blood was taken four weeks after the intravenous inoculation with the two strains of BCG and 14 days after each of the i.v. boosters. The antibodies directed against beta-galactosidase were detected by an ELISA assay on the sera of animals immunized with the r-BCG, which expresses beta-galactosidase (FIG. 3). An increase in the antibody response was observed after the various booster doses. The results are presented in FIG. 11. A considerable increase in the level of antibodies is observed after the first and again after the second booster. A third booster does not cause an increase in the level of antibodies. Antibodies directed against beta-galactosidase are detected in the sera of animals immunized with non-recombinant BCG. This response is much weaker than the response induced by r-BCG which expresses beta-galactosidase and may be due to a polyclonal activation by BCG. No antibodies were detected in the non-immunized mice These results demonstrate that the humoral response may be triggered by the r-BCG expressing a foreign (heterologous) antigen under the control of pan. Beta-galactosidase was chosen as model system but it may be replaced by any type of antigen of interest for the purposes of vaccination.

In Vivo Stability of the Different r-BCG Strains

The BCG bacilli were recovered from spleen homogenates two months after i.v. inoculation. Table II shows that the different r-BCG clones used in this study behave similarly to that of the non-recombinant BCG strain. After spreading r-BCG strains on media containing kanamycin and X-gal $2.0 \times 10^5$ blue CFU were obtained as compared with $7.4 \times 10^5$ CFU after growth in a medium in the absence of selection by kanamycin. Hence about 27% of the r-BCG population is stable after two months of in vivo growth. This proportion must make possible the multiplication and persistence of the BCG in the macrophages of the target organ which are required for long-term immunogenic stimulation.

Conclusion

The results presented here demonstrate that the r-BCG strains harbouring plasmids which code for APH3' under its own control region and beta-galactosidase under the control of pan can trigger cellular and humoral immune responses specific for these antigens in the mouse These polypeptide antigens are localized in the cytoplasm of r-BCG. As has already been described for BCG, the r-BCG derivatives must multiply within the macrophages and present the peptides of beta-galactosidase in combination with the MHC antigens. This leads to recognition by the T lymphocytes which respond by proliferating. The LN cells showed marked proliferation in response to stimulation in vitro. The CD4+ and CD8+ T cells proved to be implicated in the proliferative response with 70% of CD4+ cells and 30% CD8+ cells The production of gamma-interferon suggests an effective role of the TH1 cell subgroup. These cells are responsible for the activation of the macrophages required for the elimination of intracellular pathogenic agents. The antibody titers found also suggest the cooperation of the T cell subgroup designated as TH2 which play a role in the induction of the humoral response.

The fact that 27% of these R-BCG strains are recovered without major rearrangement after two months growth in vivo in mice suggests that they will make possible the induction of a long-term (memory) immune response. The subsequent cloning of the antigens an the chromosome using different methodologies such as transposition, homologous recombination, integration mediated by a phage or a plasmid will allow the construction of r-BCG strains which have an even more satisfactory stability and which induce more persistent long-term immune responses due to continuous stimulation.

TABLE I

Bacterial strains, phages and plasmids

| Bacteria | Description | Source or Reference |
|---|---|---|
| M. paratuberculosis | Bacterial strain isolated from a bovine with Johnes' disease | University of Massay New Zealand |
| N. smegmatis mc²155 | mc⁶ mutant with high efficiency of transformation | Snapper et al |
| M. bovis BCG | Pasteur BCG strain 1173P2 | Institut Pasteur Paris |
| E. coli Y1090 | Receptor strain for lambda gt | Sold by Pormega |
| E. coli MC1061 | Receptor strain for transformation by the plasmids which replicate in E. coli | Maniatis et al |
| E. coli DH5α | Receptor strain for transformation by the plasmids which replicate in E. coli | Maniatis et al |
| Phage | | |
| Mptg lamda gt11 | Genomic DNA library of Mptb | Murray et al |
| pUC$_{18}$ | Vector with high copy number | Murray et al |
| PGEM-2 | Plasmid vector with high copy number | Sold by Promega |
| pNM482 | Vector for promoter detection | Minton et al |
| pRR3 | E. coli - mycobacteria shuttle vector | Ranes et al |
| pAM-3 | Recombinant pGEM-2 containing a 1.6 kb EcoRI/PstI fragment of Mptb | Described in the text |
| pAM310 | pNM482 recombinant containing a 716 bp BamHI/PstI fragment of pAM3 | Described in the text |
| pAM320 | pRR3 recombinant containing a 3.8 kb DraI/SmaI fragment of pAM310 | Described in the text Described in the text |
| pAM311 | pUC$_{18}$ recombinant containing a 716 bp BamHI/PstI fragment of pAM-3 | Described in the text |
| pAM312 | pUC$_{18}$ recombinant containing a 1.6 kb EcoRI/BamHI fragment of Mptb | Described in the text |
| pSL 1180 | Derivative of pUC$_{18}$ | Pharmacia |
| pWR30 | pSL 1180 recombinant containing the XbaI/NdeI digestion product (168 bp) by PCR | Described in the text |
| pTGT 959 | Plasmid containing the PL promoter of lambda | Transgene |
| pIpJNI | pNM482 recombinant containing the XhoI/BamHI fragment of pTG959 | Described in the text |
| pWR31 | pIpJN recombinant containing the EcoRI/BlgII fragment of pWR30 (159 bp) | Described in the text |
| pWR32 + pWR33 | pRR3 recombinant containing the EcoRI/DraI fragment (3.8 kb) of pWR31 in both directions | Described in the text |

TABLE II

In vivo stability of r-BCG (+ pAM320)
BCG CFUs recovered from murine bone marrow homogenates
2 months after inoculation IV with 10⁷ Kan-kanamycin CFU

| r-BCG (+ pAM320) Clone | Culture medium 7H11 | Culture medium 7H11 + Kan + X-gal |
|---|---|---|
| 39.3 | 759000 | 199000 |
| 39.4 | 720000 | 194000 |
| BCG 1173P2 | 740000 | 0 |

TABLE III

Beta-galactosidase activity (units/mg*)
Recombinant host organism

| Plasmid | M. smegmatis | E. coli |
|---|---|---|
| pRR3 | 0 | N.D |
| pAM320 | 250 | 5–7 |
| pWR32 | 250 | 350 |
| pWR33 | 350 | 2500 |

*Dry weight, deduced from the optical density at 600 nm (1 mg dry weight per ml = 3.7 optical density units at 600 nm)
N.D. = not determined Examples of use of the pan promoter associated with ORF2 expression of viral antigens and induction of specific immune responses by the BCG expressing these antigens.

The pan promoter associated with the open reading frame ORF2 was used to express several viral antigens in the BCG. Immune responses directed against these viral antigens were observed after inoculation of the mouse with the BCG strains expressing them.

In these tests the expression of the viral antigens of the SIV strain Mac251 and HIV was assayed. The SIV or HIV sequences are given in the publication "Human retrovirus and AIDS 1991" (a compilation and analysis of nucleic acid and amino acid sequences, edited by Myers G. et al., published by Theoretical Biology and Physics, Group T-10, Mail Stop K710, Los Alamos National Laboratory, Los Alamos, N. Mex. 87545 USA).

1) The nef gene of SIV The entire nef gene of SIV was inserted at the PstI site of ORF2. In order to do this, a fragment containing the nef gene of SIV was synthesized in vitro by PCR Two oligonucleotides SN1 (5' CCCCTGCAGAGATCTATGGGTGGAGCTATT 3'(SEQ ID NO:10)) and SN2 (5' AAAAAGCTTTTAGCCTTCTTCTAACTT 3'(SEQ ID NO:11)) were synthesized by the APPLIGENE company. They were used to amplify the nef gene of SIV starting from the plasmid pTG3148 bearing it and obtained from TRANSGENE (FIG. 12). The amplified fragment bears the restriction sites PstI and HindIII. It is cut by the corresponding restriction enzymes and cloned in the plasmid b/pAM712 (FIG. 12). The recombinant plasmid bearing nef of SIV was called pSN24. Starting from this plasmid, the XbaI HindIII fragment bearing the nef gene of SIV was cut by the enzymes XbaI and HindIII, the ends were filled in by the Klenow enzyme and the fragment resulting fragment was cloned into the ScaI site of pRR3 in both orientations. The resulting plasmids were called pSN25 and pSN26.

The plasmids pSN25 and pSN26 were transferred into *M. smegmatis* and the BCG by electroporation. The fusion polypeptide ORF2-Nef is identified by Western blot by using sera of monkeys infected with SIV (FIG. 13). After inoculation of mice with the BCG expressing ORF2-Nef (SIV), a cellular immune response directed against Nef (SIV) was observed by using the proliferation test of lymph node cells after stimulation by Nef (SIV) peptides. The peptides are derived from the ANRS. They are the peptides 1–15; 16–30; 40–60 and 221–235 for which the numbers correspond to the positions of the amino adds at the N-terminus and C-terminus of the intact Nef protein. The amplitude of the responses obtained with the different peptides is indicated in FIG. 14. It is probable that they are CD4+ and CDS+ T lymphocytes as we have already shown in the case of Nef of HIV-1.

2) the env gene of HIV-1, strain MN In order to do this the cloning was performed in the same way as the cloning of nef of SIV. The gene fragment coding for the polypeptide from amino acid 242 to amino acid 335 of the gp120 protein was synthesized in vitro by PCR. Two oligonucleotides: JENVMN3:5' CGACTGTAAAAATG-TACTGACGTCCCCC 3' (SEQ ID NO: 12) and JEN-VMN4:5' TAAAAGCTTTTACTCGGTGTCGTTCGTGTC 3'(SEQ ID NO: 13) were synthesized by IGOLEN I. They were used to amplify the env gene starting from the plasmid pTG5167 constructed by Transgene (FIG. 15). The amplified fragment bears the restriction sites PstI and HindIII. It is cut by the corresponding restriction enzymes and cloned in the plasmid b/pAM712 between the PstI and the HindIII sites (FIG. 16). The resulting plasmid was called pLA11. It contains a fusion gene ORF2-env containing the 554 bp corresponding to the N-terminal part of ORF2 and the 686 bp corresponding to the N-terminal part of the env gene. The fusion PAN-ORF2-env was excised by pLA11 by a double cut by means of the enzymes BamHI and HindIII. The ends of the fragments were filled in by the Klenow polymerase. The resulting fragment was cloned in pRR3 at the ScaI site giving rise to the plasmids pLA12 and pLA13 depending on the orientation of the insert. The plasmids pLA12 and pLA13 were introduced by electroporation in *M. smegmatis* and in the BCG. The expression of the fusion ORF2-Env was detected with the aid of Western blot by using the monoclonal antibody SC-D (K24-1) of HYBRIDOLAB. As shown in FIG. 17, expression of a fusion polypeptide of the expected molecular weight (45.5 kDa) is observed.

Mice were inoculated with the BCG expressing the fusion ORF2-Env. Fifteen days after the inoculation, an in vitro proliferative response of the lymph node cells was observed after stimulation by the protein gp120 (FIG. 18). It is probable that they are also CD4+ and CD8+ T lymphocytes. Other mice were inoculated by the i.v. route and a booster dose was given after 28 days. Blood was taken at different times after injection. Fifteen days after the boster a high level of antibodies was detected by the ELISA assay by using the gp120 protein or peptides corresponding to the part of Env expressed by the BCG (FIG. 19).

3) The gag gene of HIV-1 strain LAI

Figure 20:
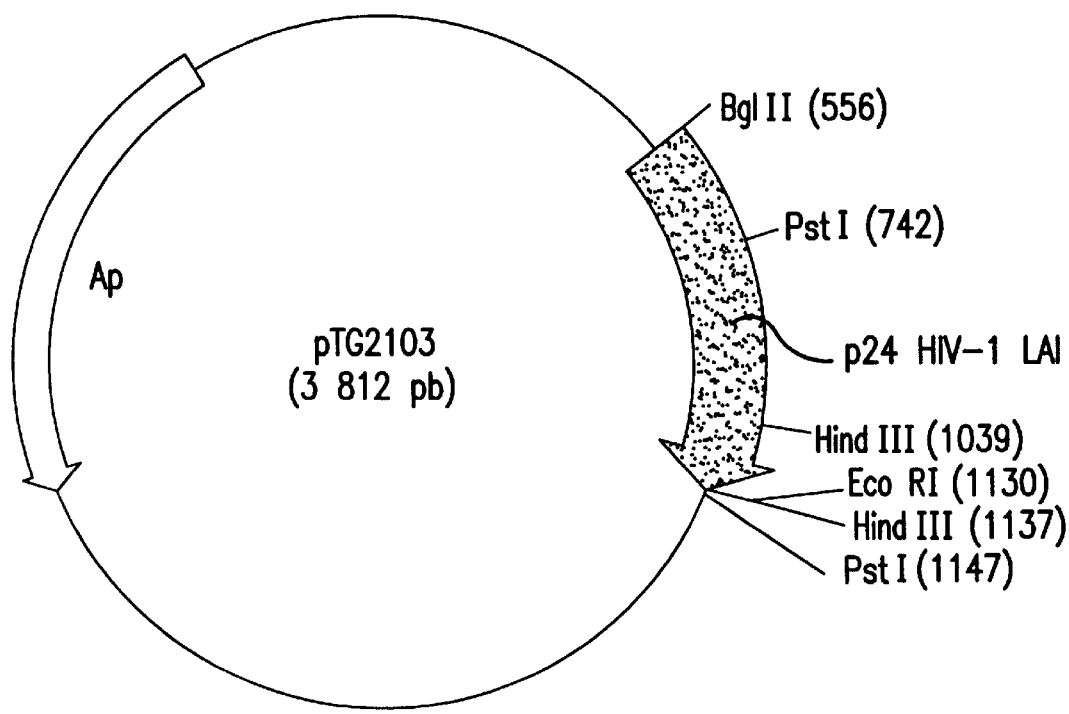
Figure 21A:
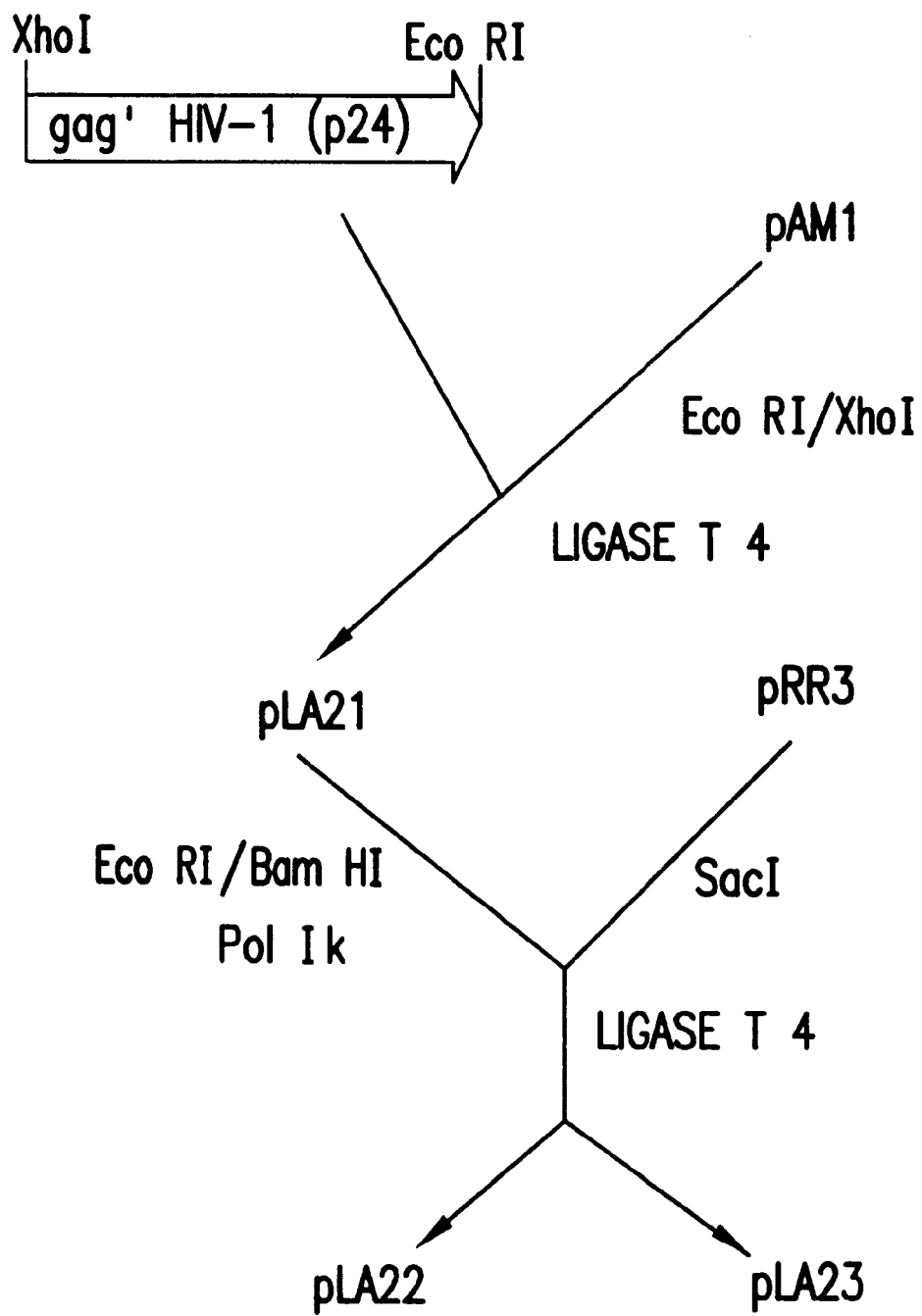
Figure 21B:
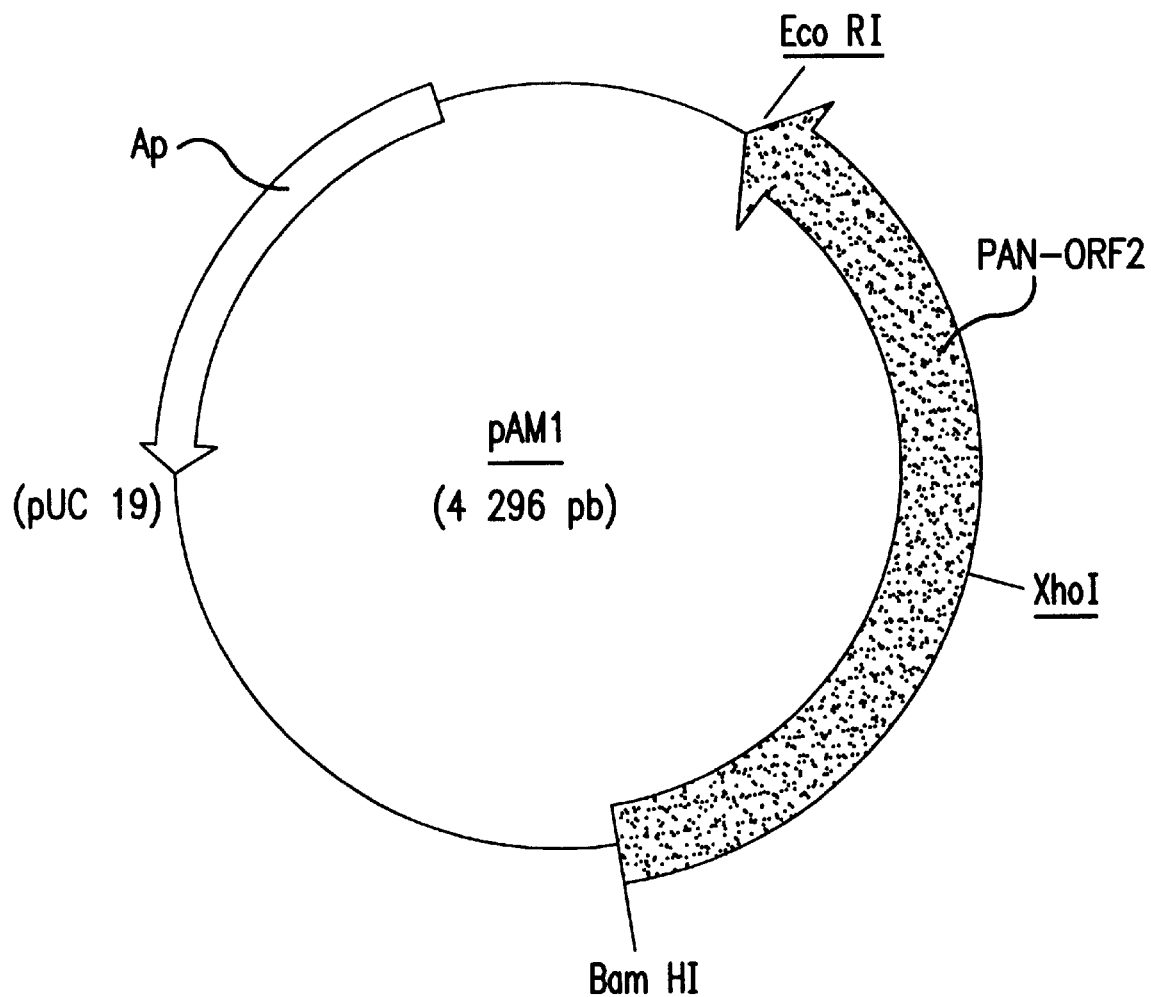
Figure 21C:
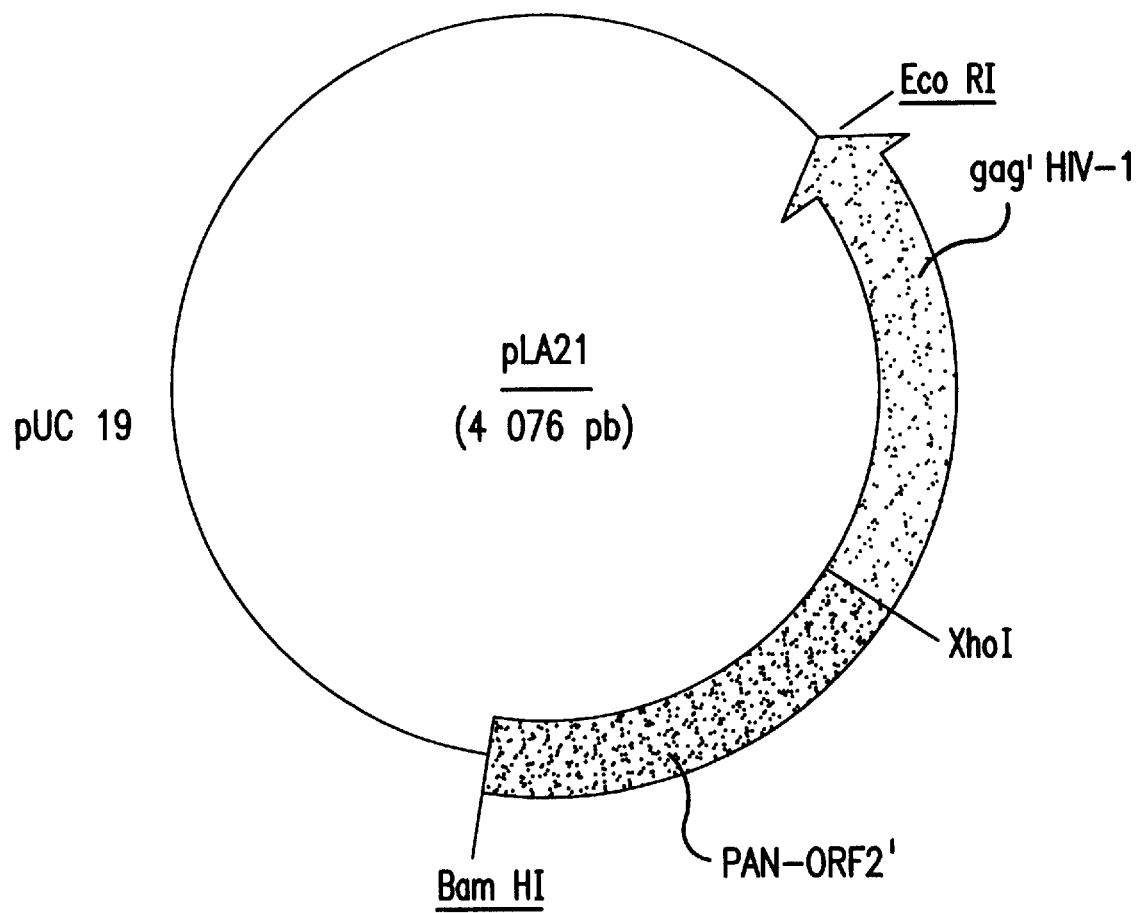
Figure 21D:
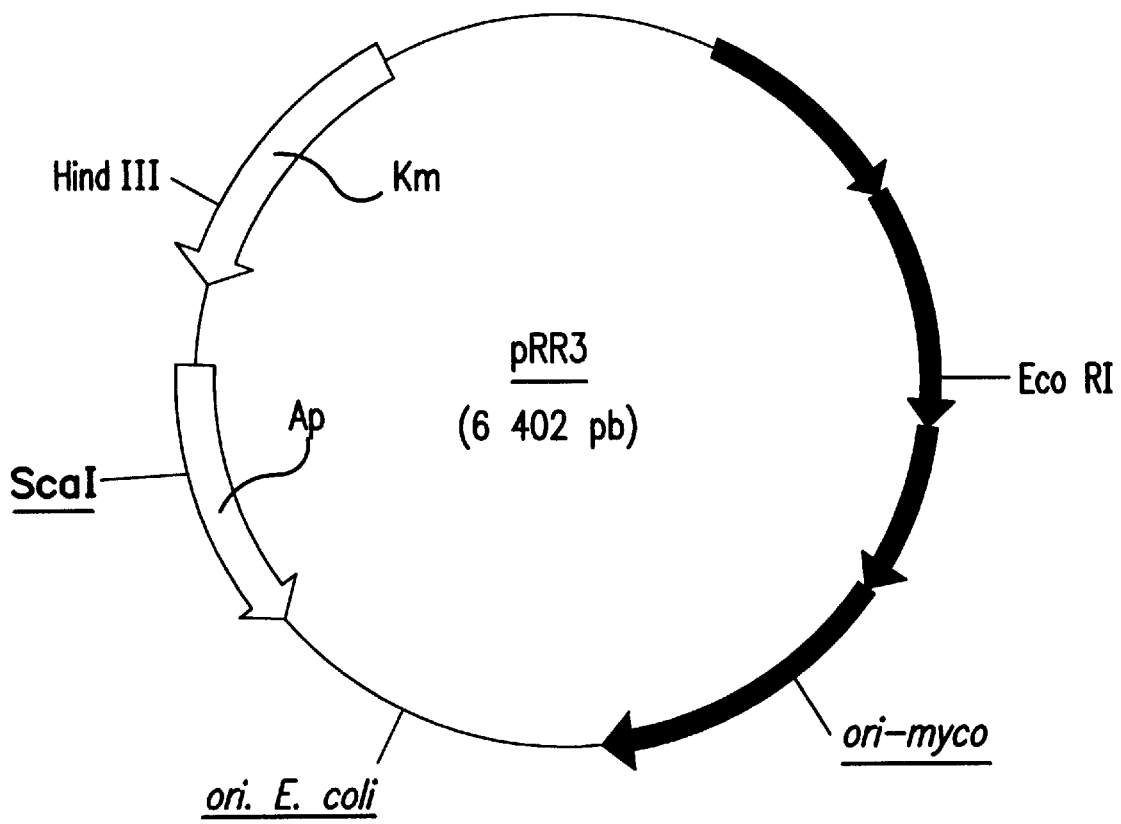
Figure 21E:
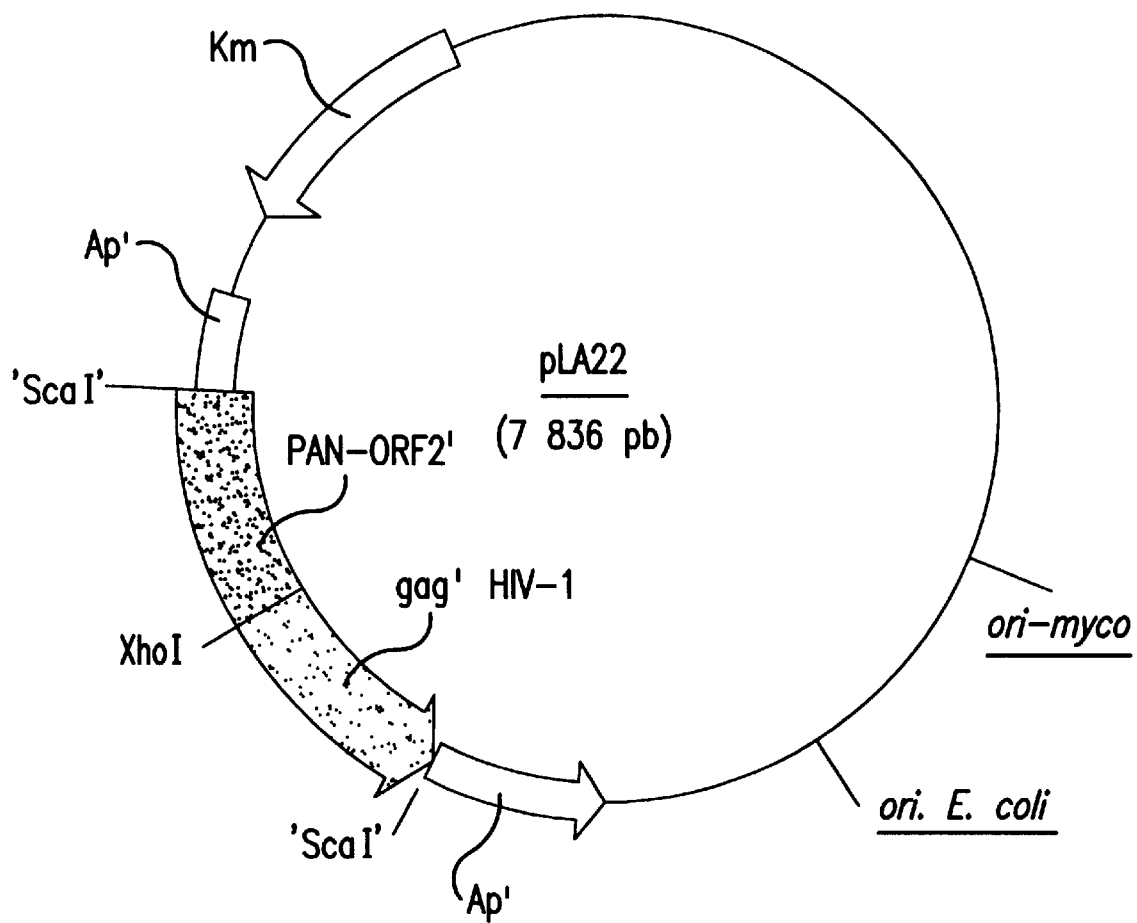
Figure 21F:
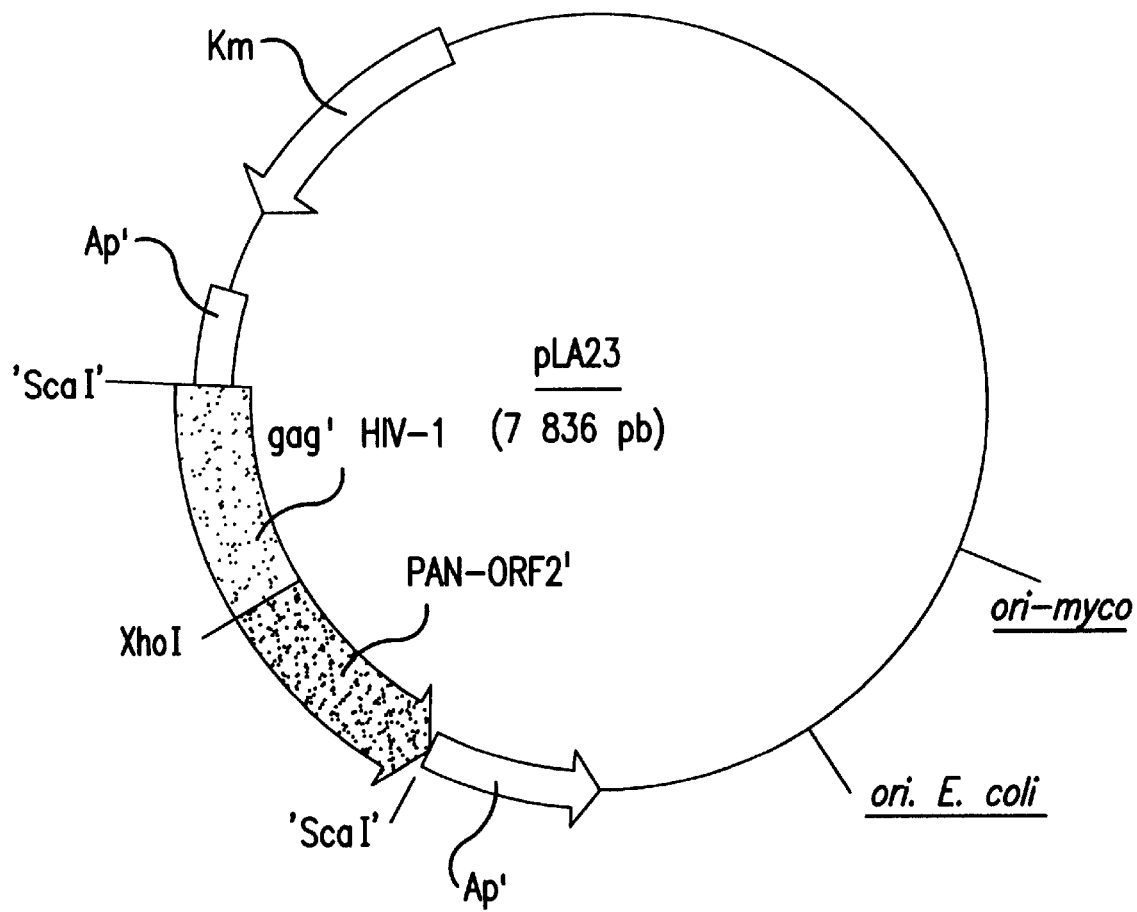
Figure 22:
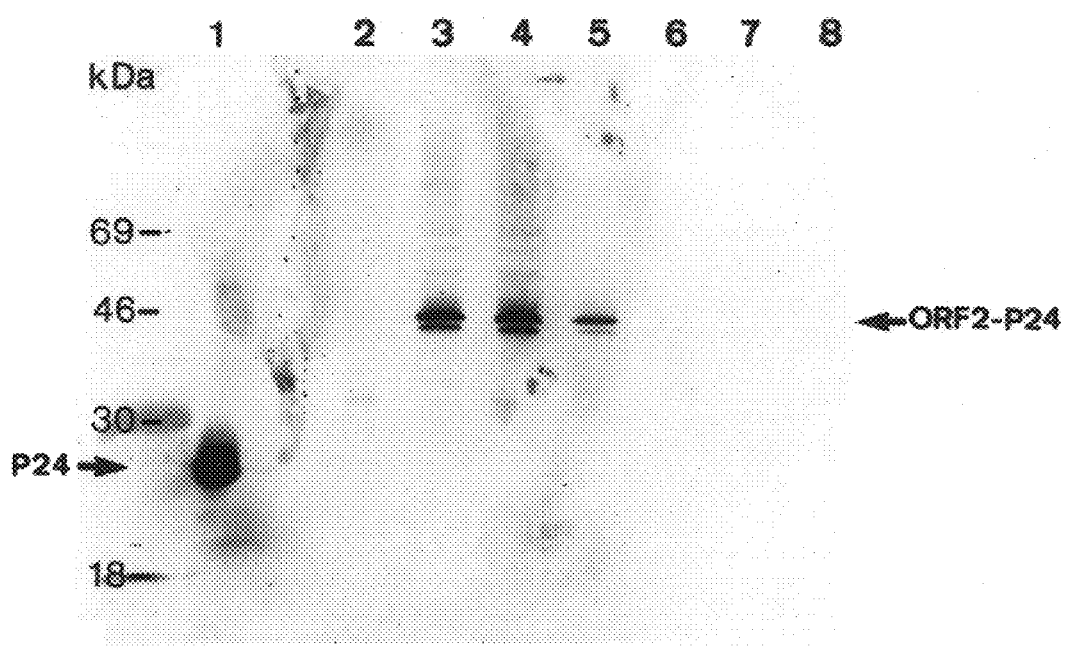

By using constructions similar to those presented above, the part of the gag gene coding for the protein P24 (the first 217 amino acids) of the HIV-1 virus LAI was inserted at the XhoI site within the ORF2. In order to do this a fragment containing the gag gene was synthesized in vitro by PCR by using the oligonucleotides EML3:
5' GGGCGCGCTCTCGAGTATGAGAACTTTAAATGCA 3' (SEQ ID NO:14) and EML5: 5' GTTCGAATTCTCA-CAAAACTCTTGC 3' (SEQ ID NO:15) and the plasmid pTG2103 constructed by Transgene (FIG. 20) as matrix. This fragment containing the gag gene was cut by the enzymes XhoI and EcoRI and cloned between the XhoI and EcoRI sites of the plasmid pAMI (Murray et al., 1992), thus generating a fusion ORF2-Gag and giving rise to the plasmid pLA21 (FIG. 21). The BamHI/EcoRI fragment bearing the fusion ORF2-Gag was excised from this plasmid pLA21 by cutting with the enzymes EcoRI and BamHI The ends of the fragments were filled in by means of the Klenow polymerase and the resulting fragment was cloned in pRR3 at the ScaI site to give rise to the plasmids pLA22 and pLA23. These plasmids were transferred by electroporation into *M. smegmatis* and the BCG. The fusion ORF2-Gag is expressed in the form of a polypeptide of 46.5 kDa by *M. smegmatis* and the BCG (FIG. 22).

We claim:

1. A purified DNA molecule comprising regulatory units for the expression of a heterologous nucleotide sequence in a host cell, which purified DNA molecule comprises:
   (a) the DNA sequence of SEQ ID NO:1;
   (b) the DNA sequence of SEQ ID NO:6; or
   (c) fragments of the sequence of (a) or (b) which comprise a transcription initiation site and elements necessary for the recognition and binding of an RNA polymerase; or
   (d) sequences which (i) hybridize with sequences complementary to the sequences of (a), (b) or (c) at 65° C. in a hybridization solution of 50% formamide, 5× SSPE, 200 µg/ml salmon sperm DNA and 10× Denhardt's solution and (ii) comprise a transcription initiation site and elements necessary for the recognition and binding of an RNA polymerase.

2. The purified DNA molecule of claim 1, wherein the elements necessary for the recognition and binding of an RNA polymerase comprise a sequence TACACT 10 nucleotides 5' to the transcription initiation site, and a sequence TCGACA 35 nucleotides 5' to the transcription initiation site.

3. The purified DNA molecule of claim 1, wherein the fragment of (c) is
   (1) SEQ ID NO:7; or
   (2) sequences which (i) hybridize with the sequence complementary to the sequence of (1) at 65° C. in a hybridization solution of 50% formamide, 5× SSPE, 200 µg/ml salmon sperm DNA and 10× Denhardt's solution and (ii) comprise a transcription initiation site and elements necessary for the recognition and binding of an RNA polymerase.

4. The purified DNA molecule of claim 1, wherein nucleotides identified as nucleotides +2 to +41 of SEQ ID NO:1 are substituted with a different sequence, wherein said different sequence comprises a Shine-Dalgarno sequence.

5. A purified DNA molecule comprising as a first DNA molecule the DNA molecule of claim 1 operably linked to a second DNA molecule such that said second DNA molecule is expressed in a host cell.

6. The purified DNA molecule of claim 5, wherein said second DNA molecule encodes a peptide or polypeptide is a hapten molecule.

7. The purified DNA molecule of claim 5, wherein said second DNA molecule encodes a peptide or polypeptide of human immunodeficiency virus (HIV).

8. The purified DNA molecule of claim 5, wherein said HIV is HIV-1 or HIV-2.

9. The purified DNA molecule of claim 8, wherein said peptide or polypeptide is an envelope protein or Nef.

10. The purified DNA molecule of claim 5, wherein said second nucleotide sequence is a mycobacterial sequence.

11. The purified DNA molecule of claim 5, wherein said mycobacterial sequence encodes a protein associated with virulence.

12. The purified DNA molecule of claim 10, wherein said mycobacterial sequence encodes a protein which induces protective antibodies in an immunized host animal.

13. The purified DNA molecule of claim 5, wherein said second nucleotide sequence encodes one or more epitopes.

14. The purified DNA molecule of claim 5, wherein the purified DNA molecule is a fusion operon.

15. The purified DNA molecule of claim 5, wherein the purified DNA molecule is a fusion gene.

16. A vector for cloning or expression of a heterologous protein comprising the purified DNA molecule of claim 5.

17. The vector of claim 16, wherein the vector is a plasmid, transposon or phage.

18. The vector of claim 17, wherein the vector was deposited with the Collection Nationale des Microorganismes on Oct. 23, 1991 under No. I-1157.

19. The vector of claim 16, wherein said purified DNA molecule is located 5' to a site for inserting a second DNA molecule.

20. The vector of claim 16, wherein said purified DNA molecule is located 3' to a site for inserting a second DNA molecule.

21. The vector of claim 16, further comprising a DNA sequence which encodes an expression marker.

22. The vector of claim 16, further comprising a DNA sequence which regulates expression of the second DNA molecule in a specific host cell.

23. A host cell transformed with the vector of claim 16.

24. The host cell of claim 23, wherein said host cell expresses the protein on its surface.

25. The host cell of claim 23, wherein said host cell secretes the protein.

26. The host cell of claim 23, wherein said host cell is Actinomycetes.

27. The host cell of claim 26, wherein the Actinomycetes is *M. bovis*.

28. The host cell of claim 27, wherein the *M. bovis* is BCG.

29. The host cell of claim 23, wherein said host cell is a gram-negative bacterium.

30. The host cell of claim 29, wherein said gram-negative bacterium is *E. coli*.

31. The host cell of claim 23, wherein said host cell is a gram-positive bacterium.

32. The host cell of claim 31, wherein said gram-positive bacterium is *B. subtilis* or Streptomyces.

33. An immunogenic composition comprising an amount of the host cell of claim 23 sufficient to induce antibodies or induce a cellular immune response in an immunized animal.

34. The immunogenic composition of claim 33, wherein the antibodies are protective.

35. The host cell of claim 16, wherein said host cell expresses a protein encoded by said second DNA molecule.

36. A method for cloning and/or expression of a nucleotide sequence in a host cell other than *Mycobacterium paratuberculosis* (Mptb) comprising operably joining said nucleotide sequence to the purified DNA molecule of claim 1, and transforming said host cell with said nucleotide sequence joined to said purified DNA molecule.

37. The method of claim 36, wherein said host cell is Actinomycetes, *M. bovis*, *E. coli* or a gram-positive bacterium.

38. The method of claim 37, wherein the *M. bovis* is bacillus of Calmette and Guerin (BCG), or the gram-positive bacterium is *B. subtilis*.

39. A vector for cloning or expression of a heterologous protein comprising the purified DNA molecule of claim 1.

40. The vector of claim 39, wherein the vector is a plasmid, transposon or phage.

41. The vector of claim 39, wherein said purified DNA molecule is located 5' to a site for inserting a second DNA molecule.

42. The vector of claim 39, wherein said purified DNA molecule is located 3' to a site for inserting a second DNA molecule.

43. The vector of claim 39, further comprising a DNA sequence which encodes an expression marker.

44. The vector of claim 39, further comprising a DNA sequence which regulates expression of the purified DNA molecule in a specific host cell.

45. A host cell transformed with the vector of claim 39.

* * * * *

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
      (A) LENGTH: 716 base pairs
      (B) TYPE: nucleic acid
      (C) STRANDEDNESS: single
      (D) TOPOLOGY: linear (ix) FEATURE:
      (A) NAME/KEY: CDS
      (B) LOCATION: 160..714

(xi) SEQUENCE DESCRIPTION: SEQ ID NO:1:

```
GATCCCGTGA CAAGGCCGAA GAGCCCGCGA CCGTGCGGTC GTCGACGACC GAGTGTGAGC        60

AGACCCCCTG GTGAAGGGTG AATCGACAGG TACACACAGC CGCCATACAC TTCGCTTCAT       120

GCCCTTACGG GGGGCGGCCA ACCCAGAAGG AGATTCTCA ATG ACG TTG TCA AGC          174
                                            Met Thr Leu Ser Ser
                                              1               5

CGC CGC GGT AGT GGT TGC GGG GTG GTA GAC AGC GTG GTC GCG CAG CAT        222
Arg Arg Gly Ser Gly Cys Gly Val Val Asp Ser Val Val Ala Gln His
             10                  15                  20

GGC CCA CAG GAC GTT GAG GCG GCG GCG GGC CAG GGC GAG GAC GGC TTG        270
Gly Pro Gln Asp Val Glu Ala Ala Ala Gly Gln Gly Glu Asp Gly Leu
     25                  30                  35
```

```
GGT GTG GCG TTT TCC TTC GGT GCG TTT TCG GTC GTA GTA GGT GCG CGA         318
Gly Val Ala Phe Ser Phe Gly Ala Phe Ser Val Val Val Gly Ala Arg
         40                  45                  50

GGA GGG GTC GGT GCG GAT GCT GAC CAA GGC CGA CAG GTA GCA GGC GCG         366
Gly Gly Val Gly Ala Asp Ala Asp Gln Gly Arg Gln Val Ala Gly Ala
 55                  60                  65

CAG CAG GCG CCG GTC GTA GCG TCG GGG GCG TTT GAG GTT TCC GCT GAT         414
Gln Gln Ala Pro Val Val Ala Ser Gly Ala Phe Glu Val Ser Ala Asp
 70                  75                  80                  85

GCG GCC GGA ATC TCG TGG TAC CGG CGC CAG GCC GGC GAC GCC GGC GAG         462
Ala Ala Gly Ile Ser Trp Tyr Arg Arg Gln Ala Gly Asp Ala Gly Glu
                 90                  95                 100

GCG GTC GGC GGA GGC GAA TGC GGC CAT GTC CCC GCC GGT GGC GGC GAG         510
Ala Val Gly Gly Gly Glu Cys Gly His Val Pro Ala Gly Gly Gly Glu
         105                 110                 115

GAA CTC AGC GCC CAG GAT GAC GCC GAA TCC GGG CAT GCT CAG GAT GAT         558
Glu Leu Ser Ala Gln Asp Asp Ala Glu Ser Gly His Ala Gln Asp Asp
     120                 125                 130

TTC GGC GTG GCG GTG GCG GCG AAA TCG CTC CTC GAT CAT CGC GTC GGT         606
Phe Gly Val Ala Val Ala Ala Lys Ser Leu Leu Asp His Arg Val Gly
 135                 140                 145

GTC GCC GAT TTC GGT GTC GAG GGC CAT CAC CTC CTT GGC CAG GCG GGC         654
Val Ala Asp Phe Gly Val Glu Gly His His Leu Leu Gly Gln Ala Gly
 150                 155                 160                 165

CAC CAC AGT GGC CGC CAG TTG TTG GCC GGG CAC GAT GCT GTG TTG GGC         702
His His Ser Gly Arg Gln Leu Leu Ala Gly His Asp Ala Val Leu Gly
                 170                 175                 180

GTT AGC GGC CTG CA                                                      716
Val Ser Gly Leu
         185

(2) INFORMATION FOR SEQ ID NO:2:

(i) SEQUENCE CHARACTERISTICS:
        (A) LENGTH: 185 amino acids
        (B) TYPE: amino acid
        (D) TOPOLOGY: linear (ii) MOLECULE TYPE: protein (xi) SEQUENCE DESCRIPTION: SEQ ID NO:2:

Met Thr Leu Ser Ser Arg Arg Gly Ser Gly Cys Gly Val Val Asp Ser
 1               5                  10                  15

Val Val Ala Gln His Gly Pro Gln Asp Val Glu Ala Ala Gly Gln
             20                  25                  30

Gly Glu Asp Gly Leu Gly Val Ala Phe Ser Phe Gly Ala Phe Ser Val
         35                  40                  45

Val Val Gly Ala Arg Gly Gly Val Gly Ala Asp Ala Asp Gln Gly Arg
     50                  55                  60

Gln Val Ala Gly Ala Gln Gln Ala Pro Val Val Ala Ser Gly Ala Phe
 65                  70                  75                  80

Glu Val Ser Ala Asp Ala Ala Gly Ile Ser Trp Tyr Arg Arg Gln Ala
                 85                  90                  95

Gly Asp Ala Gly Glu Ala Val Gly Gly Gly Glu Cys Gly His Val Pro
             100                 105                 110

Ala Gly Gly Gly Glu Glu Leu Ser Ala Gln Asp Asp Ala Glu Ser Gly
         115                 120                 125

His Ala Gln Asp Asp Phe Gly Val Ala Val Ala Ala Lys Ser Leu Leu
 130                 135                 140

Asp His Arg Val Gly Val Ala Asp Phe Gly Val Glu Gly His His Leu
```

```
            145                 150                 155                 160
Leu Gly Gln Ala Gly His His Ser Gly Arg Gln Leu Leu Ala Gly His
                    165                 170                 175

Asp Ala Val Leu Gly Val Ser Gly Leu
            180                 185
```

(2) INFORMATION FOR SEQ ID NO:3:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:3:

```
CCCCTCTAGA ATTCCGTGAC AAGGCCGAAG AGCCCGCGA                              39
```

(2) INFORMATION FOR SEQ ID NO:4:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:4:

```
AACATATGAG ATCTTCTCCT TCTGGGTTGG CCGCCCC                                37
```

(2) INFORMATION FOR SEQ ID NO:5:

(i) SEQUENCE CHARACTERISTICS:
        (A) LENGTH: 168 base pairs
        (B) TYPE: nucleic acid
        (C) STRANDEDNESS: single
        (D) TOPOLOGY: linear (xi) SEQUENCE DESCRIPTION: SEQ ID NO:5:

```
GATCCCGTGA CAAGGCCGAA GAGCCCGCGA CCGTGCGGTC GTCGACGACC GAGTGTGAGC       60

AGACCCCCTG GTGAAGGGTG AATCGACAGG TACACACAGC CGCCATACAC TTCGCTTCAT      120

GCCCTTACGG GGGGCGGCCA ACCCAGAAGG AGATTCTCAA TGACGTTG                   168
```

(2) INFORMATION FOR SEQ ID NO:6:

(i) SEQUENCE CHARACTERISTICS:
        (A) LENGTH: 159 base pairs
        (B) TYPE: nucleic acid
        (C) STRANDEDNESS: single
        (D) TOPOLOGY: linear (xi) SEQUENCE DESCRIPTION: SEQ ID NO:6:

```
GATCCCGTGA CAAGGCCGAA GAGCCCGCGA CCGTGCGGTC GTCGACGACC GAGTGTGAGC       60

AGACCCCCTG GTGAAGGGTG AATCGACAGG TACACACAGC CGCCATACAC TTCGCTTCAT      120

GCCCTTACGG GGGGCGGCCA ACCCAGAAGG AGATTCTCA                             159
```

(2) INFORMATION FOR SEQ ID NO:7:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:7:

```
TCGACAGGTA CACACAGCCG CCATACACTT CGCTTCA                                37
```

(2) INFORMATION FOR SEQ ID NO:8:

(i) SEQUENCE CHARACTERISTICS:
(A) LENGTH: 1608 base pairs
(B) TYPE: nucleic acid
(C) STRANDEDNESS: single
(D) TOPOLOGY: linear (ix) FEATURE:
(A) NAME/KEY: CDS
(B) LOCATION: 160..1308

(xi) SEQUENCE DESCRIPTION: SEQ ID NO:8:

```
GATCCCGTGA CAAGGCCGAA GAGCCCGCGA CCGTGCGGTC GTCGACGACC GAGTGTGAGC      60

AGACCCCCTG GTGAAGGGTG AATCGACAGG TACACACAGC CGCCATACAC TTCGCTTCAT     120

GCCCTTACGG GGGGCGGCCA ACCCAGAAGG AGATTCTCA ATG ACG TTG TCA AGC        174
                                           Met Thr Leu Ser Ser
                                                           190

CGC CGC GGT AGT GGT TGC GGG GTG GTA GAC AGC GTG GTC GCG CAG CAT      222
Arg Arg Gly Ser Gly Cys Gly Val Val Asp Ser Val Val Ala Gln His
                195                 200                 205

GGC CCA CAG GAC GTT GAG GCG GCG GCG GGC CAG GGC GAG GAC GGC TTG      270
Gly Pro Gln Asp Val Glu Ala Ala Ala Gly Gln Gly Glu Asp Gly Leu
            210                 215                 220

GGT GTG GCG TTT TCC TTC GGT GCG TTT TCG GTC GTA GTA GGT GCG CGA      318
Gly Val Ala Phe Ser Phe Gly Ala Phe Ser Val Val Val Gly Ala Arg
        225                 230                 235

GGA GGG GTC GGT GCG GAT GCT GAC CAA GGC CGA CAG GTA GCA GGC GCG      366
Gly Gly Val Gly Ala Asp Ala Asp Gln Gly Arg Gln Val Ala Gly Ala
    240                 245                 250

CAG CAG GCG CCG GTC GTA GCG TCG GGG GCG TTT GAG GTT TCC GCT GAT      414
Gln Gln Ala Pro Val Val Ala Ser Gly Ala Phe Glu Val Ser Ala Asp
255                 260                 265                 270

GCG GCC GGA ATC TCG TGG TAC CGG CGC CAG GCC GGC GAC GCC GGC GAG      462
Ala Ala Gly Ile Ser Trp Tyr Arg Arg Gln Ala Gly Asp Ala Gly Glu
                275                 280                 285

GCG GTC GGC GGA GGC GAA TGC GGC CAT GTC CCC GCC GGT GGC GGC GAG      510
Ala Val Gly Gly Gly Glu Cys Gly His Val Pro Ala Gly Gly Gly Glu
            290                 295                 300

GAA CTC AGC GCC CAG GAT GAC GCC GAA TCC GGG CAT GCT CAG GAT GAT      558
Glu Leu Ser Ala Gln Asp Asp Ala Glu Ser Gly His Ala Gln Asp Asp
        305                 310                 315

TTC GGC GTG GCG GTG GCG GCG AAA TCG CTC CTC GAT CAT CGC GTC GGT      606
Phe Gly Val Ala Val Ala Ala Lys Ser Leu Leu Asp His Arg Val Gly
    320                 325                 330

GTC GCC GAT TTC GGT GTC GAG GGC CAT CAC CTC CTT GGC CAG GCG GGC      654
Val Ala Asp Phe Gly Val Glu Gly His His Leu Leu Gly Gln Ala Gly
335                 340                 345                 350

CAC CAC AGT GGC CGC CAG TTG TTG GCC GGG CAC GAT GCT GTG TTG GGC      702
His His Ser Gly Arg Gln Leu Leu Ala Gly His Asp Ala Val Leu Gly
                355                 360                 365

GTT AGC GGC CTG CAG CGC GGT GGC TGC GAC GGT ATC GGC GTT GCG GGC      750
Val Ser Gly Leu Gln Arg Gly Gly Cys Asp Gly Ile Gly Val Ala Gly
            370                 375                 380

CTT GCG TTT ACG CAA GAA CGC GGC TAC TCG AGC GCC ACC GGC GCT GCG      798
Leu Ala Phe Thr Gln Glu Arg Gly Tyr Ser Ser Ala Thr Gly Ala Ala
        385                 390                 395

CAG CGC GTC GGG AGT TTG GTA GCC AGT AAG CAG GAT CAG CGC GGC ACG      846
Gln Arg Val Gly Ser Leu Val Ala Ser Lys Gln Asp Gln Arg Gly Thr
    400                 405                 410
```

```
GCT CTT GTT GTA GTC GAA GGC GCG TTC CAG CGC CGG AAA GTA TTC CAG      894
Ala Leu Val Val Val Glu Gly Ala Phe Gln Arg Arg Lys Val Phe Gln
415                 420                 425                 430

CAG CTG GGC GCG CAT TCG GTT GAT CGC CCG GGT CCG ATC AGC CAC CAG      942
Gln Leu Gly Ala His Ser Val Asp Arg Pro Gly Pro Ile Ser His Gln
            435                 440                 445

ATC GGA ACG TCG GCT GGT CAG GAT GCG CAG CTC GAC TGC GAT GTC ATC      990
Ile Gly Thr Ser Ala Gly Gln Asp Ala Gln Leu Asp Cys Asp Val Ile
                450                 455                 460

GCC GGC GCG CAG AGG CTG CAA GTC GTG GCG CAT CCG GGC CTG ATC GGC     1038
Ala Gly Ala Gln Arg Leu Gln Val Val Ala His Pro Gly Leu Ile Gly
            465                 470                 475

GAT GAT CGC AGC GTC TTT GGC GTC GGT CTT GCC TTC GCC GCG GTA ACT     1086
Asp Asp Arg Ser Val Phe Gly Val Gly Leu Ala Phe Ala Ala Val Thr
        480                 485                 490

ACC CGC GGC GTG ATG GAC CGT GCG CCC GGG AAT ATA AAG CAG CCG CTG     1134
Thr Arg Gly Val Met Asp Arg Ala Pro Gly Asn Ile Lys Gln Pro Leu
495                 500                 505                 510

CCC GGC AGC GAT GAG CAA GGC GAT CAG CAA CGC GGC GCC GCC GGC GTT     1182
Pro Gly Ser Asp Glu Gln Gly Asp Gln Gln Arg Gly Ala Ala Gly Val
            515                 520                 525

GAG GTC GAT CGC CCA CGT GAC CTC GCC TCC ATC GGC CAA CGT CGT CAC     1230
Glu Val Asp Arg Pro Arg Asp Leu Ala Ser Ile Gly Gln Arg Arg His
                530                 535                 540

CGC CGC AAA TCA ACT CCA GCA GCG CGG CCT CGT CGT TGG CCA CCC GCT     1278
Arg Arg Lys Ser Thr Pro Ala Ala Arg Pro Arg Arg Trp Pro Pro Ala
            545                 550                 555

GCG AGA GCA ATC GCT GCG CGT CGT CGT TAA TAACCATGCA GTAATGGTCG       1328
Ala Arg Ala Ile Ala Ala Arg Arg Arg *
560                 565

GCCTTACCGG CGTCCACGCC CGCCCAGACA GGTTGTGCCA CAACCACCTC CGTAACCGTC   1388

ATTGTCCAGA TCAACCCAGC AGACGACCAC GCCGACGTGT CCTTACACAG CGATCCAATC   1448

GCATCTCTCA ATTAGCGGTC GAGTCGTCGC GGGACGCCGG GCGGCCAATC TCCTTCGGCC   1508

ATCCAACACA GCAACCACAT GAAAGCCATA CCCGACGTCC CTGGGCAATT CGAAGCCTAA   1568

GCCGACGGCC CCGAACACCC TTCAAGAAAG GTAAGGAATT                         1608

(2) INFORMATION FOR SEQ ID NO:9:

(i) SEQUENCE CHARACTERISTICS:
        (A) LENGTH:   382 amino acids
        (B) TYPE: amino acid
        (D) TOPOLOGY: linear (ii) MOLECULE TYPE: protein (xi) SEQUENCE DESCRIPTION: SEQ ID NO:9:

Met Thr Leu Ser Ser Arg Arg Gly Ser Gly Cys Gly Val Val Asp Ser
1               5                   10                  15

Val Val Ala Gln His Gly Pro Gln Asp Val Glu Ala Ala Gly Gln
            20                  25                  30

Gly Glu Asp Gly Leu Gly Val Ala Phe Ser Phe Gly Ala Phe Ser Val
            35                  40                  45

Val Val Gly Ala Arg Gly Val Gly Ala Asp Ala Asp Gln Gly Arg
    50                  55                  60

Gln Val Ala Gly Ala Gln Gln Ala Pro Val Val Ala Ser Gly Ala Phe
65                  70                  75                  80

Glu Val Ser Ala Asp Ala Ala Gly Ile Ser Trp Tyr Arg Arg Gln Ala
                85                  90                  95
```

```
Gly Asp Ala Gly Glu Ala Val Gly Gly Glu Cys Gly His Val Pro
            100                 105                 110
Ala Gly Gly Gly Glu Glu Leu Ser Ala Gln Asp Asp Ala Glu Ser Gly
            115                 120                 125
His Ala Gln Asp Asp Phe Gly Val Ala Val Ala Ala Lys Ser Leu Leu
            130                 135                 140
Asp His Arg Val Gly Val Ala Asp Phe Gly Val Glu Gly His His Leu
145                 150                 155                 160
Leu Gly Gln Ala Gly His His Ser Gly Arg Gln Leu Leu Ala Gly His
                165                 170                 175
Asp Ala Val Leu Gly Val Ser Gly Leu Gln Arg Gly Gly Cys Asp Gly
                180                 185                 190
Ile Gly Val Ala Gly Leu Ala Phe Thr Gln Glu Arg Gly Tyr Ser Ser
            195                 200                 205
Ala Thr Gly Ala Ala Gln Arg Val Gly Ser Leu Val Ala Ser Lys Gln
            210                 215                 220
Asp Gln Arg Gly Thr Ala Leu Val Val Glu Gly Ala Phe Gln Arg
225                 230                 235                 240
Arg Lys Val Phe Gln Gln Leu Gly Ala His Ser Val Asp Arg Pro Gly
                245                 250                 255
Pro Ile Ser His Gln Ile Gly Thr Ser Ala Gly Gln Asp Ala Gln Leu
            260                 265                 270
Asp Cys Asp Val Ile Ala Gly Ala Gln Arg Leu Gln Val Val Ala His
        275                 280                 285
Pro Gly Leu Ile Gly Asp Asp Arg Ser Val Phe Gly Val Gly Leu Ala
        290                 295                 300
Phe Ala Ala Val Thr Thr Arg Gly Val Met Asp Arg Ala Pro Gly Asn
305                 310                 315                 320
Ile Lys Gln Pro Leu Pro Gly Ser Asp Glu Gln Gly Asp Gln Arg
                325                 330                 335
Gly Ala Ala Gly Val Glu Val Asp Arg Pro Arg Asp Leu Ala Ser Ile
            340                 345                 350
Gly Gln Arg Arg His Arg Arg Lys Ser Thr Pro Ala Ala Arg Pro Arg
            355                 360                 365
Arg Trp Pro Pro Ala Ala Arg Ala Ile Ala Ala Arg Arg Arg
370                 375                 380

(2) INFORMATION FOR SEQ ID NO:10:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:10:

CCCCTGCAGA GATCTATGGG TGGAGCTATT                              30

(2) INFORMATION FOR SEQ ID NO:11:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:11:

AAAAAGCTTT TAGCCTTCTT CTAACTT                                 27
```

(2) INFORMATION FOR SEQ ID NO:12:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:12:

CGACTGTAAA AATGTACTGA CGTCCCCC            28

(2) INFORMATION FOR SEQ ID NO:13:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:13:

TAAAAGCTTT TACTCGGTGT CGTTCGTGTC          30

(2) INFORMATION FOR SEQ ID NO:14:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:14:

GGGCGCGCTC TCGAGTATGA GAACTTTAAA TGCA      34

(2) INFORMATION FOR SEQ ID NO:15:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:15:

GTTCGAATTC TCACAAAACT CTTGC              25